US005767088A

United States Patent [19]

Horwell et al.

[11] Patent Number: 5,767,088

[45] Date of Patent: Jun. 16, 1998

[54] TACHYKININ ANTAGONISTS

[75] Inventors: David Christopher Horwell, Foxton; William Howson, Weston Colville; Martyn Clive Pritchard, St. Ives; Jennifer Raphy, Bishops Stortford, all of England

[73] Assignee: Warner-Lambert Company, Morris Plains, N.J.

[21] Appl. No.: 697,992

[22] Filed: Sep. 4, 1996

Related U.S. Application Data

[60] Division of Ser. No. 346,052, Nov. 29, 1994, Pat. No. 5,610,145, which is a continuation-in-part of Ser. No. 228,236, Apr. 15, 1994, abandoned.

[51] Int. Cl.$^6$ ............................................. A61K 38/05
[52] U.S. Cl. ..................... 514/19; 514/18; 562/445; 562/438; 562/439; 562/443; 560/13; 560/37; 564/305
[58] Field of Search ......................... 562/445, 438, 562/439, 443; 514/19, 18; 564/305; 560/13, 37

[56] References Cited

U.S. PATENT DOCUMENTS 5,610,145  3/1997  Horwell et al. ................ 514/19

FOREIGN PATENT DOCUMENTS

93/01160  1/1993  WIPO.
93/01165  1/1993  WIPO.
93/01169  1/1993  WIPO.

OTHER PUBLICATIONS

Goldstein et al, Scientific American, 255: 74–83, 1986.
Jackowski, British Journal of Neurosurgery, 9: 303–317, 1995.
Cecil Textbook of Medicine, contents, pp. XXIV–XXXVI), 1992.
S. Nakanishi, *Physiol Rev.* vol. 67:4, 1987, 1117–1142.
S. Guard, *Neurochem Int.*, vol. 18:2, 1991, 149–165.
S. Nakanishi, *Annual Rev Nuerosci*, 14, 1991, 123–136.
B.E. Tomczuk, et al, *Current Opinions in Therapeutic Patents*, vol. 1:2, 1991, 197–210.
R. M. Snider, et al., *Science*, 251, 1991, 435–437.
C. Garret, et al., *Proc Natl Acad Sci*, vol. 88, 1991, 10208–10212.
C. Advenier, et al., *Brit J Pharmacol*, vol. 105, 1992, 78.
A.M. MacLeod, et al., *J Med Chem*, 36, 1993, 2044–2045.
J. Fujii, et al., *Neuropeptides*, vol. 22, 1992, 24.
C.A. Maggi, et al., *J Auton Pharmacol*, 13, 1993, 23–93.
C. Polidori, et al., *Neurosci Lett*, 103, 1989 320–325.
M. Massi, et al., *Neurosci Lett*, 92, 1988, 341–346.
P. Elliott, et al., *Neuropeptides*, 19, 1991, 119–126.
A.J. Stoessl, et al., *Psychopharmacology*, 95, 1988, 502–506.
A.J. Stoessl, et al., *Neuroscience Letters*, 80, 1987, 321–326.

*Primary Examiner*—Stephen Walsh
*Assistant Examiner*—Eliane Lazar-Wesley
*Attorney, Agent, or Firm*—Elizabeth M. Anderson

[57] ABSTRACT

The small compounds of the instant invention are tachykinin antagonists. The compounds are highly selective and functional $NK_3$ antagonists expected to be useful in the treatment of pain, depression, anxiety, panic, schizophrenia, neuralgia, addiction disorders, inflammatory diseases, gastrointestinal disorders, vascular disorders, and neuropathological disorders.

8 Claims, No Drawings

TACHYKININ ANTAGONISTS

This is a divisional application of U.S. application Ser. No. 08/346,052 filed Nov. 29, 1994, now U.S. Pat. No. 5,610,145, which is a continuation-in-part of Ser. No. 08/228,236 filed Apr. 15, 1994, now abandoned.

BACKGROUND OF THE INVENTION

Over the last decade, major advances have been made in the understanding of the biology of the mammalian tachykinin neuropeptides. It is now well established that substance-P (1), neurokinin A (NKA) (2), and neurokinin B (NKB) (3), all of which share a common C-terminal sequence Phe-X-Gly-Leu-Met-$NH_2$, (Nakanishi S., *Physiol. Rev.*, 67:117 (1987)), are widely distributed throughout the periphery and central nervous system (CNS) where they appear to interact with at least three receptor types referred to as $NK_1$, $NK_2$, and $NK_3$, (Guard S., et al., *Neurosci. Int.*, 18:149 (1991)). Substance-P displays highest affinity for $NK_1$ receptors, whereas NKA and NKB bind preferentially to $NK_2$ and $NK_3$ receptors, respectively. Recently, all three receptors have been cloned and sequenced and shown to be members of the G-protein-linked "super family" of receptors (Nakanishi S., *Annu. Rev. Neurosci.*, 14:123 (1991)). A wealth of evidence supports the involvement of tachykinin neuropeptides in a variety of biological activities including pain transmission, vasodilation, smooth muscle contraction, bronchoconstriction, activation of the immune system (inflammatory pain), and neurogenic inflammation (Pernow B., *Pharmacol. Rev.*, 35:85 (1983)). However, to date, a detailed understanding of the physiological roles of tachykinin neuropeptides has been severely hampered by a lack of selective, high affinity, metabolically stable tachykinin receptor antagonists that possess both good bioavailability and CNS penetration. Although several tachykinin receptor antagonists have been described (Tomczuk B. E., et al., *Current Opinions in Therapeutic Patents*, 1:197 (1991)), most have been developed through the modification and/or deletion of one or more of the amino acids that comprise the endogenous mammalian tachykinins such that the resulting molecules are still peptides that possess poor pharmacokinetic properties and limited in vivo activities.

However, since 1991, a number of high-affinity nonpeptide antagonists have been reported. Snider R. M., et al., (*Science*, 251:435 (1991)), and Garret C., et al., (*Proc. Natl. Acad. Sci.*, 88:10208 (1991)), described CP-96,345 and RP 67580, respectively, as antagonists at the $NK_1$ receptor, while Advenier C., et al., (*Brit. J. Pharmacol.*, 105:78 (1992)), presented data on SR 48969 showing its high affinity and selectivity for $NK_2$ receptors. More recently Macleod, et al., (*J. Med. Chem.*, 36:2044 (1993)) have published on a novel series of tryptophan derivatives as $NK_1$ receptor antagonists. It is of interest that most of the non-peptide tachykinin receptor antagonists described to date arose, either directly or indirectly, out of the screening of large compound collections using a robust radioligand binding assay as the primary screen. Recently, FK 888, a "dipeptide" with high affinity for the $NK_1$ receptor was described (Fujii J., et al., *Neuropeptide*, 22:24 (1992)).

International Publication Numbers WO 93/01169, WO 93/01165, and WO 93/001160 cover certain nonpeptide tachykinin receptor antagonists.

NKB and also $NK_3$ receptors are distributed throughout the periphery and central nervous system (Maggi, et al., *J. Auton. Pharmacol.*, 13:23 (1993)). NKB is believed to mediate a variety of biological actions via the $NK_3$ receptor including gastric acid secretion; appetite regulation; modulation of serotonergic, cholinergic, and dopaminergic systems; smooth muscle contraction and neuronal excitation. Recent publications descriptive of this art include Polidor, et al., *Neuroscience Letts.*, 103:320 (1989); Massi, et al., *Neuroscience Letts.*, 92:341 (1988), and Improta, et al., *Peptides*, 12:1433 (1991). Due to its actions with dopaminergic (Elliott, et al., *Neuropeptides*, 19:119 (1991)), cholinergic (Stoessl, et al., *Psycho. Pharmacol.*, 95:502 (1988)), and serotonergic (Stoessl, et al., *Neuroscience Letts.*, 80:321 (1987)) systems, NKB may play a role in psychotic behavior, memory functions, and depression.

Accordingly, compounds capable of antagonizing the effects of NKB at $NK_3$ receptors will be useful in treating or preventing a variety of disorders including pain, depression, anxiety, panic, schizophrenia, neuralgia, addiction disorders, inflammatory diseases; gastrointestinal disorders including colitis, Crohn's disease, inflammatory bowel disorder, and satiety; vascular disorders such as angina and migraine and neuropathological disorders such as Parkinsonism and Alzheimer's.

SUMMARY OF THE INVENTION

The invention covers tachykinin antagonists. The compounds of the invention have been proved to be highly selective and functional $NK_3$ antagonists.

Compounds of the invention are those of formula

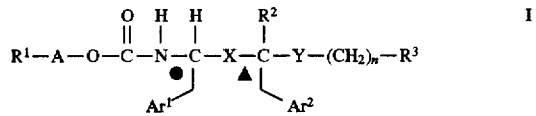

or a pharmaceutically acceptable salt thereof wherein:
$R^1$ is hydrogen,
  $OR^4$,
  $CO_2R^4$,
  cyclo- or polycycloalkyl of from 4 to 10 carbons with from 0 to 3 substituents selected from:
    alkyl,
    halogen,
    $(CH_2)_mCO_2R^4$,
    $(CH_2)_mOR^4$ wherein m is an integer of from 1 to 6 and $R^4$ is hydrogen or alkyl, or
  phenyl unsubstituted or substituted by from 1 to 3 groups selected from:
    alkyl,
    halogen,
    nitro,
    $CF_3$,
    $(CH_2)_pOR^6$,
    $(CH_2)_pCO_2R^6$,
    $(CH_2)_pNR^6R^7$ wherein p is an integer of from 0 to 6 and $R^6$ and $R^7$ are each independently hydrogen or alkyl;

A is —$(CH_2)_q(C(CH_3)_2)_r(CH_2)_s$— wherein q, r, and s are integers of from 0 to 6, 0 to 1, and 0 to 6, respectively;

$Ar^1$ and $Ar^2$ are each independently phenyl unsubstituted or substituted with from 1 to 3 substituents selected from:
  alkyl,
  halogen,
  nitro,
  $CF_3$,
  $(CH_2)_tOR^6$,
  $(CH_2)_tCO_2R^6$, or $(CH_2)_tNR^6R^7$ wherein t is an integer of from 0 to 6 and $R^6$ and $R^7$ are each independently hydrogen or alkyl;

X and Y are each independently
- —CONH—,
- —CONCH$_3$—,
- —COO—,
- —CH$_2$NH—,
- —NHCO—,
- —CH$_2$O—,
- —COCH$_2$—, or
- —CH$_2$CH—;

n is an integer of from 0 to 10; and $R^3$ is hydrogen,
straight or branched alkyl of from 3 to 10 carbons with from 0 to 3 substituents selected from:
- $(CH_2)_nOR^8$,
- $CO_2R^8$,
- —NHCOCH$_3$,
- —NR$^8$R$^9$,
- —SO$_2$Me,
- —SOMe,
- —SO$_2$NH$_2$,
- —CONR$^8$R$^9$,
- —NHCONR$^8$R$^9$,
- —COR$^4$ wherein n is an integer of from 0 to 6, $R^4$ is as above, $R^8$ and $R^9$ are each independently hydrogen or alkyl,
- -guanidine,
- -amidine, $R^3$ is also

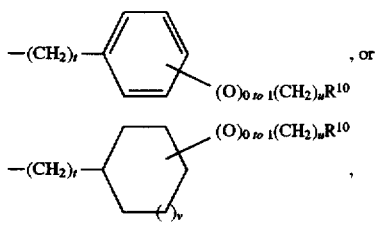

wherein t is an integer of from 0 to 5, v is an integer of from 0 to 2, u is an integer of from 0 to 4, and $R^{10}$ is hydrogen, hydroxy, alkoxy, COOH, CO$_2$alkyl, CONR$^8$R$^9$, NHCONR$^8$R$^9$ guanidine or amidine.

All stereoisomers are considered (●, ▲).

Preferred compounds of this invention are those of Formula I above wherein $R^1$ is hydrogen,
OR$^4$,
CO$_2$R$^4$ wherein $R^4$ is hydrogen, methyl, or ethyl, cycloalkyl of from 4 to 8 carbons,
bicycloalkyl of 10 carbons,
tricycloalkyl of 10 carbons, or
phenyl;

A is —$(CH_2)_q(C(CH_3)_2)_r(CH_2)_s$— wherein q, r, and s are integers of from 0 to 2, 0 to 1, and 0 to 4, respectively;

Ar$^1$ and Ar$^2$ are each independently phenyl unsubstituted or mono- or disubstituted by:
- alkyl,
- halogen,
- CF$_3$,
- NO$_2$, or
- NH$_2$;

X and Y are each independently
- —CONH—,
- —CONCH$_3$—,
- —CO$_2$—, or
- —CH$_2$NH—;

n is an integer of from 0 to 9; and $R^3$ is hydrogen,
straight, branched, or cyclic alkyl of from 3 to 10 carbons with from 0 to 3 substituents selected from:
- OH,
- OCH$_3$,
- CO$_2$R$^8$,
- NHCOCH$_3$,
- NR$^8$R$^9$,
- CONR$^8$R$^9$,
- NHCONR$^8$R$^9$ wherein $R^8$ and $R^9$ are each independently selected from hydrogen and methyl, or
- COCH$_3$,

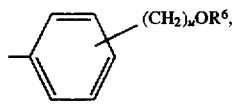

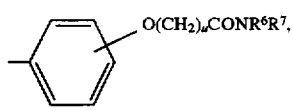

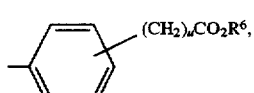

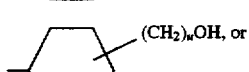

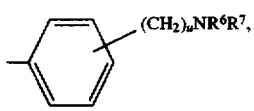

wherein u is an integer of from 0 to 4 and $R^6$ and $R^7$ are each independently selected from hydrogen and methyl.

Preferred stereoisomers are when ● is S and ▲ is R.

More preferred compounds of this invention are those of Formula I above wherein:

$R^1$ is hydrogen,
OR$^4$,
CO$_2$R$^4$ wherein $R^4$ is hydrogen or methyl, cycloalkyl of from 5 to 7 carbons;

A is —$(CH_2)_q(C(CH_3)_2)_r(CH_2)_s$— wherein q, r, and s are integers of from 0 to 3, 0 to 1, and zero, respectively;

Ar$^1$ and Ar$^2$ are each independently phenyl unsubstituted or mono- or disubstituted by:
- alkyl,
- chloro, or
- CF$_3$;

X and Y are each independently
- —CONH—,
- —CONCH$_3$—,
- —CO$_2$—, or
- —CH$_2$NH—;

n is an integer of from 0 to 9; and $R^3$ is hydrogen,
straight, branched, or cycloalkyl of from 3 to 10 carbons with from 0 to 3 substituents selected from:
- OH,
- OCH$_3$, $CO_2R^8$,
$CONR^8R^9$, or
$NHCONR^8R^9$,

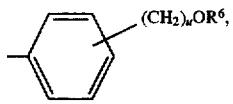

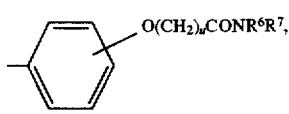

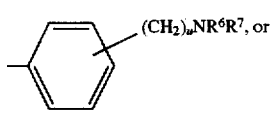

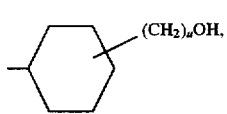

wherein u is an integer of from 0 to 3, $R^6$ and $R^7$ are each independently hydrogen and methyl, $R^8$ and $R^9$ are each independently hydrogen and methyl.
Preferred stereoisomers are when ● is S and ▲ is R.
Still more preferred compounds of the invention are when:

$R^1$ is cyclohexane,
 cyclopentane,
 methylcyclohexane,
 methylcyclopentane,
 phenylethyl,
 t-butyl,
 2,2-dimethylpropane, or
 2,2-dimethylpentane;
A when q, r and s are zero;
$Ar^1$ and $Ar^2$ are each phenyl;
X and Y are each independently selected from —CONH— and —$CH_2NH$—;
n is an integer of from 3 to 8;
$R^3$ is straight, branched, or cycloalkyl of from 3 to 9 carbons with 1 substituent selected from:
 OH,
 —$OCH_3$,
 —$CONR^8R^9$,
 —$NHCONR^8R^9$,

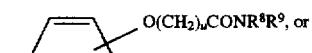

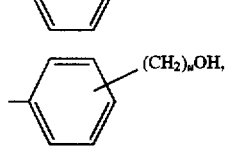

wherein u is an integer of from 0 to 3 and $R^8$ and $R^9$ are each independently selected from hydrogen and methyl.
Especially preferred examples of the invention are:
D-Phenylalaninamide, N-[(1,1-dimethylethoxy)-carbonyl]-L-phenylalanyl-N-(8-hydroxyoctyl)-α-methyl-;
D-Phenylalaninamide, N-[(1,1-dimethylethoxy)-carbonyl]-L-phenylalanyl-N-(9-amino-9-oxononyl)-α-methyl-, trifluroacetate (10:7) salt;
D-Phenylalaninamide, N-[(1,1-dimethylethoxy)-carbonyl]-L-phenylalanyl-N-[4-(4-methoxyphenyl)butyl-α-methyl-;
DL-Phenylalaninamide, N-[(1,1-dimethylethoxy)-carbonyl]-L-phenylalanyl-N-[3-(4-hydroxyphenyl)propyl]-α-methyl-;
DL-Phenylalaninamide, N-[(1,1-dimethylethoxy)-carbonyl]-L-phenylalanyl-α-methyl-N-3-methylbutyl-;
DL-Phenylalaninamide, N-[(1,1-dimethylethoxy)-carbonyl]-L-phenylalanyl-α-methyl-N-(5-phenylpentyl)-;
DL-Phenylalaninamide, N-[(1,1-dimethylethoxy)-carbonyl]-L-phenylalanyl-N-cyclopentyl-α-methyl-;
DL-Phenylalaninamide, N-[(1,1-dimethylethoxy)-carbonyl]-L-phenylalanyl-N-(8-methoxyoctyl)-α-methyl-;
DL-Phenylalaninamide, N-[(1,1-dimethylethoxy)-carbonyl]-L-phenylalanyl-N-(7-carboxyheptyl)-α-methyl-;
DL-Phenylalaninamide, N-[(1,1-dimethylethoxy)-carbonyl]-L-phenylalanyl-N-[2-(acetylamino)ethyl]-α-methyl-;
DL-Phenylalaninamide, N-[(1,1-dimethylethoxy)-carbonyl]-L-phenylalanyl-N-(2-cyclopentylethyl)-α-methyl-;
DL-Phenylalaninamide, N-[(1,1-dimethylethoxy)-carbonyl]-L-phenylalanyl-N-[2-(4-chlorophenyl)ethyl]-α-methyl-;
DL-Phenylalaninamide, N-[(1,1-dimethylethoxy)-carbonyl]-L-phenylalanyl-N-[(4-carboxycyclohexyl)-methyl]-α-methyl-, trans—;
DL-Phenylalaninamide, N-[(1,1-dimethylethoxy)-carbonyl]-L-phenylalanyl-α-methyl-;
DL-Phenylalaninamide, N-[(4-hydroxyphenyl)acetyl]-L-phenylalanyl-α-methyl-;
DL-Phenylalaninamide, N-[(cyclohexylmethoxy)-carbonyl]-L-phenylalanyl-α-methyl-;
DL-Phenylalaninamide, N-[(2-methylpropoxy)-carbonyl]-L-phenylalanyl-α-methyl-;
DL-Phenylalaninamide, N-[[(3,4-dichlorophenyl)-methoxy]carbonyl]-L-phenylalanyl-α-methyl-;
DL-Phenylalaninamide, N-[[(octahydro-2-naphthalenyl)oxy]carbonyl]-L-phenylalanyl-α-methyl-;
DL-Phenylalaninamide, N-[(1,1-dimethylethoxy)-carbonyl]-L-phenylalanyl-3-chloro-α-methyl-;
D-Phenylalaninamide, 3-chloro-N-[(1,1-dimethylethoxy)carbonyl]-DL-phenylalanyl-α-methyl-;
Carbamic acid, [2-[[2-amino-2-oxo-1-(phenylmethyl)ethyl]amino]-1-(phenylmethyl)ethyl]-, 1,1-dimethylethyl ester;
D-Phenylalaninamide, N-[(1,1-dimethylethoxy)-carbonyl]-L-phenylalanyl-N-[7-[(aminocarbonyl)-amino]heptyl]-α-methyl-;
D-Phenylalaninamide, N-[(1,1-dimethylethoxy)-carbonyl]-L-phenylalanyl-α-methyl-N-[8-(methylsulfonyl)octyl]-; and
D-Phenylalaninamide, N-[(1,1-dimethylethoxy)-carbonyl]-L-phenylalanyl-α-methyl-N-[9-(methylamino)-2-oxononyl]-.

Pharmaceutical compositions of therapeutically effective amounts of one or more compounds of Formula I and a pharmaceutically acceptable carrier as useful in treating central nervous system disorders such as but not limited to pain, anxiety, depression, and schizophrenia, panic, addiction disorders.

The compounds are also expected to be useful in treating gastrointestinal diseases including but not limited to colitis, Crohn's disease, inflammatory bowel disorder, and satiety.

The compounds are also expected to be useful in treating respiratory disorders such as but not limited to asthma.

The compounds are also expected to be useful in treating inflammation.

The compounds are also expected to be useful in treating circulatory insufficiencies.

DETAILED DESCRIPTION

The compounds of Formula I are further defined as follows.

The term "alkyl" means a straight or branched hydrocarbon having from 1 to 12 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, undecyl, dodecyl, and the like unless stated specifically otherwise.

The term "cycloalkyl" means a saturated hydrocarbon ring which contains from 3 to 12 carbon atoms, for example, cyclopropyl, cyclobutyl, cyclopentyl, cyclohexyl except as otherwise specifically stated.

The term "polycycloalkyl" means two or more rings as defined above for cycloalkyl such as adamantyl, norbornyl, and bornyl except as otherwise specifically stated.

The term "halogen" is chlorine, fluorine, bromine, or iodine.

The compounds of Formula I are capable of forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharma. Sci.*, 66:1 (1977)).

The acid addition salts of said basic compounds are prepared by contacting the free base form with a sufficient amount of the desired acid to produce the salt in the conventional manner. Preferably, a peptide of Formula I can be converted to an acidic salt by treating with an aqueous solution of the desired acid, such that the resulting pH is less than four. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S.M., et al., supra).

The base addition salts of said acidic compounds are prepared by contacting the free acid form with a sufficient amount of the desired base to produce the salt in the conventional manner. Preferably, a peptide of Formula I can be converted to a base salt by treating with an aqueous solution of the desired base, such that the resulting pH is greater than nine. The solution can be passed through a C18 cartridge to absorb the peptide, washed with copious amounts of water, the peptide eluted with a polar organic solvent such as, for example, methanol, acetonitrile, aqueous mixtures thereof, and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The compounds of the instant invention are highly selective and competitive antagonists of the $NK_3$ receptor.

Compounds have been tested in the in vitro peripheral guinea pig ileum assay and the central guinea pig medial habenula paradigm (see Table I).

TABLE I

| | $NK_3$ Antagonist Activity | |
|---|---|---|
| Example | Guinea Pig Medial Habenula (Ke, nM) | Guinea Pig Ileum ($K_B$, nM) |
| 1 | 54 | 40 |
| 2 | 25 | 10 |

The protocols for these two in vitro functional assays are described below. For the guinea pig medial habenula assay, extracellular recordings were made from guinea pig medial habenula neurones in a brain slice preparation in vitro. Compounds were tested for the ability to block senktide-induced increases in firing rate. Parallel shifts to the right of the senktide dose-response curve with no reduction in maximum were taken as an indication of competitive antagonism. Equilibrium constant (Ke) values for the antagonism were obtained from separate experiments and yielded the mean Ke values shown in the final column. None of the compounds tested had any effect on basal neuronal firing rates.

The experimental procedure for the guinea pig ileum assay is as follows.

Noncumulative concentration-response curves to the selective $NK_1$ agonist (Met-O-Me[11]) substance P (substance P-methyl ester, SPOMe) were constructed by addition of increasing doses ($\leq 10$ μL) to the organ bath. To assess the effect of putative antagonists, concentration-response curves to the agonist were obtained in the absence, and then the presence of known concentrations of the presumptive antagonist. Contractile responses to SPOMe were expressed as a percentage of the maximum response for the one preparation, and concentration-response data fitted by a least-squares iterative method in Inpolot (Graphpad Software, Inc.) to the logistic function $R=100.x^n/(EC_{50}{}^n+x^n)$, where R is the response, x is the agonist concentration, $EC_{50}$ is the "location parameter" for the curve (approximates to the value for $EC_{50}$, the concentration of agonist producing 50% of the maximum response), and n is the "slope factor" of the curve. The effect of the antagonist was observed as a rightward shift of the log(concentration)–response curve, and generally this was quantified in terms of the "dose ratio" (DR) between $[EC_{50}]_A$ and $[EC_{50}]_C$, these parameters being the measures made in the presence and absence of antagonist, respectively. By repeating estimates for DR using at least three observations at any one concentration of antagonist, and not less than three concentrations of antagonist, the affinity of the antagonist was derived by Schild analysis by plotting log(DR-1) agonist–log [antagonist]. The plots were analyzed by regression analysis, and if the slope of the line of best fit was not significantly different from unity, the intercept on the abscissa from the regression analysis with the slope constrained to unity was taken as the negative logarithm of $K_B$ ($pK_B$), the estimate of the antagonist dissociation constant.

The compounds of the invention were also evaluated in an $NK_3$ receptor binding assay which is described below.

Chinese hamster ovary cell membranes were prepared on day of use by thawing cells, diluting with culture medium, and centrifuging at 1000 g for 4 minutes. The resulting pellet was resuspended in assay buffer (50 mM Tris, pH 7.4 containing 3 mM $MnCl_2$, 0.02% BSA, 40 µg/L bacitracin, 2 µg/mL chymostatin, 2 µM phosphoramidon, and 4 µg/mL leupeptin), and washed by centrifugation as above. The cells were then resuspended in assay buffer, counted, and volume adjusted as appropriate. The cell suspension was homogenized using a Brinkman polytron (setting 6, 3×10 s) and the equivalent of 0.2–0.25 million cells added per tube. For competition studies, membranes were incubated with [$^{125}$I] -[MePhe$^7$]neurokinin B (40–100 pM) in the presence and absence of test compounds for 90 minutes at 22° C. Assays were terminated by filtration under vacuum using a Brandel harvester onto GF/C filters presoaked with 0.1% PEI for at least 2 hours, and cpm bound determined using a gamma counter. In all cases, specific binding was defined by 1 µM senktide.

TABLE II

| In Vitro $NK_3$ Receptor Binding Data | |
|---|---|
| Example | Binding $IC_{50}$ (nM) |
| 1 | 40 |
| 2 | 20 |
| 3 | 83 |
| 4 | 88 |
| 5 | 123 |
| 6 | 77 |
| 7 | 556 |
| 8 | 102 |
| 9 | 229 |
| 10 | 180 |
| 11 | 129 |
| 12 | 141 |
| 13 | 719 |
| 14 | 1520 |
| 15 | 5890 |
| 16 | 1220 |
| 17 | 1310 |

TABLE II-continued

| In Vitro $NK_3$ Receptor Binding Data | |
|---|---|
| Example | Binding $IC_{50}$ (nM) |
| 18 | 1530 |
| 19 | 3060 |
| 20 | 1350 |
| 21 | 904 |
| 22 | 4330 |
| 23 | 16 |
| 24 | 21 |
| 25 | 69 |
| 26 | 21 |

DESCRIPTION OF SYNTHETIC SCHEMES

Schemes 1 through 3 describe the synthesis of intermediates required for the preparation of the final compounds as found in the examples.

In Scheme 1 the BocPheαMePheOH intermediate is prepared by active ester coupling of the acid Boc(s)Phe to either R or S isomers of αMePheOMe followed by base catalyzed hydrolysis. The methyl ester αMePheOMe is synthesized from the readily available acid via the use of thionyl chloride and methanol.

The synthesis of the amine Intermediates III and IV are described in Scheme 2. Conversion of the readily available 9-bromo-1-nonanol to the corresponding amino acid was achieved via initial oxidation of the alcohol to the acid using concentrated nitric acid followed by displacement of the bromine by azide and subsequent conversion of the azide to the amine via catalytic hydrogenation. Protection of the amine with a Boc group followed by protection of the acid in the form of a methyl ester gave, after acid catalyzed deprotection of the Boc group, the required amino acid methyl ester Intermediate III. Intermediate IV was similarly prepared via azide displacement of the bromine atom in 8-bromo-1-octanol followed by catalytic reduction of the azide group to an amine.

Scheme 3 describes the synthesis of Intermediate V which is a 4-aryl butylamine derivative. Friedel-Crafts acylation of anisole with succinic anhydride yielded a γ-keto acid which was subsequently reduced to give an aryl alkyl acid derivative. This was converted to Intermediate V via the amide followed by reduction with borane methyl sulfide complex.

The synthesis of Examples 1 through 3 are described in Scheme 4. Active ester coupling of the acid Intermediate I with the amine Intermediates IV and V gave Examples 1 and 3, respectively. Example 2 was prepared starting from Intermediate I via initial active ester coupling with Intermediate III followed by base hydrolysis of the methyl ester to the corresponding acid and finally conversion to the target amide via active ester methodology.

Schemes 5 and 6 describe the synthesis of further intermediates listed as Intermediates VI to IX. Amine Intermediates VI and VII, 5-phenyl-1-pentylamine and cyclopentylethylamine, were prepared from their corresponding alcohols via conversion of the alcohol to the tosylate followed by displacement of the tosylate by azide and reduction of the azide to the target amines VI and VII. Intermediates VIII and IX were both prepared from N-Boc protected 8-amino-1-octanoic acid which in turn was prepared from readily available 8-amino-1-octanoic via a Schotten-Baumen acylation. Conversion of the acid of N-Boc-8-amino-1-octanoic acid to the alcohol followed by methylation using trimethylsilyl diazomethane yielded, after acid catalyzed removal of the Boc group, Intermediate VIII. Esterification of the acid group in N-Boc-8-amino-1- octanoic acid using active ester methodology followed by acid catalyzed removal of the Boc group gave Intermediate IX.

The synthesis of Examples 4 through 13 are described in Scheme 7. The central starting material for these syntheses was Boc(S)Phe(RS)αMePheOH. Examples 4 through 8 are prepared from the central intermediate by active ester coupling to 3-(4-hydroxyphenyl)propylamine, 3-methylbutylamine, 5-phenyl-1-pentylamine, cyclopentylamine, and Intermediate III, respectively. Example 9 is synthesized via active ester mediated coupling of Intermediate IX to the acid intermediate followed by base catalyzed hydrolysis to yield the desired acid. Finally, Examples 10 through 13 were prepared via active ester coupling of the acid intermediate to N-acetylethylenediamine, cyclopentylethylamine (VII), 2-(4-chlorophenyl)ethylamine, and trans-4-(aminomethyl) cyclohexane carboxylic acid, respectively.

In Scheme 8, Example 14 is prepared from αMePhe via initial N-Boc protection, preparation of the amide via active ester methodology, acid catalyzed removal of the N-Boc group, and finally coupling to Boc(S)PheOpfp. Removal of the N-Boc group with TFA gave an amine intermediate, (S)Phe(RS)αMePheNH$_2$, from which Examples 15 and 16 were prepared via active ester coupling to 4-hydroxyphenyl acetic acid and addition to cyclohexyl methyl chloroformate, respectively.

In Scheme 9, Examples 17 and 18 were prepared by the addition of isobutyl chloroformate and 3,4-dichlorobenzylchloroformate, respectively, to the amine intermediate (XII). Intermediate XII was, in turn, prepared from TFA(RS)αMePheNH$_2$ via coupling to Fmoc(S)PheOpfp followed by piperidine catalyzed deprotection of the Fmoc group.

The synthesis of Example 19 is described in Scheme 10. Base promoted coupling of the p-nitrophenyl carbonate of decahydro-2-naphthol to the amine Intermediate XII yielded the desired carbamate derivative Example 19.

Scheme 11 describes the synthesis of Examples 20 and 21. Example 20 is derived from m-chlorophenylalanine methyl ester and is synthesized via initial N-Boc protection, hydrolysis of the methyl ester to the corresponding carboxylic acid followed by active ester coupling of the acid group to Intermediate XI, TFA(R)αMePheNH$_2$. Example 21 is synthesized starting from α-methyl-m-chlorophenyl alanine which is then coupled, using to active ester methodology, to Boc(S)Phe and the methyl ester converted to the amide in Example 21 via base catalyzed hydrolysis to the acid followed by active ester ammonolysis.

The synthesis of the aminomethylene amide bond isostere derivative, Example 22, is described in Scheme 12. The starting material for this synthesis N-Boc protected phenylalaninol. This is then oxidized using Sweun conditions to the aldehyde which is consequently reductively coupled to (S)phenylalaninamide to yield Example 22.

The synthesis of the compound of Example 23 is described in Scheme 13.

Reduction of the in situ generated unsymmetrical anhydride of the carboxylic acid derivative (1) with LiBH$_4$ in THF gave the alcohol (2). Removal of the nitrogen protecting Boc group of this compound with TFA gave the TFA salt (3). This was subsequently coupled to Boc(S)Phe(R)αMePhe using active ester methodology to give the amide (4). The C-terminal alcohol moiety of this compound was converted to its corresponding azide (6) via preparation of the tosylate using TsCC and base in dichloromethane followed by subsequent displacement with NaN$_3$. The azide was catalytically reduced over Lindlar catalyst to give the amide (7), which was then converted to the target urea (8) by reaction with trimethylisocyanate in THF.

The synthesis of the compound of Example 24 is described in Scheme 14.

Conversion of the alcohol moiety of (1) into its corresponding tosylate (2) was achieved by reaction with TsCC in dichloromethane and triethylamine/DMAP. Subsequent reaction of the tosylate with methanethiol and K$_2$CO$_3$ in DMF gave the thioether (3). This was oxidized by using MCPBA in dichloromethane to yield the target sulphane (4).

The synthesis of the compound of Example 25 is described in Scheme 15.

Phenol O-alkylation of (1) with bromoacetamide and K$_2$CO$_3$ in butan-2-one gave the ether (2). The alkyl alcohol moiety of (2) was then converted to its chloro analogue (3) by reaction with TsCC and pyridine in dichloromethane. Subsequent reaction with NaN$_3$ in DMF gave the azide (4), which was catalytically reduced over Lindlar catalyst to give the amine (5). This was then coupled to Boc(S)Phe(R)αMePhe using active ester methodology to yield the target amide (6).

INTERMEDIATES

SCHEME 1

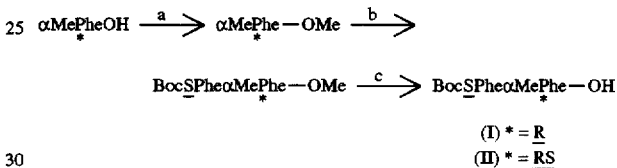

BocSPheαMePhe—OMe $\xrightarrow{c}$ BocSPheαMePhe—OH (I) * = R
(II) * = RS a) SOCl$_2$, MeOH;
b) BocSPhe, HBTU, DIPEA, DMF;
c) 1M LiOH, dioxan.

SCHEME 2

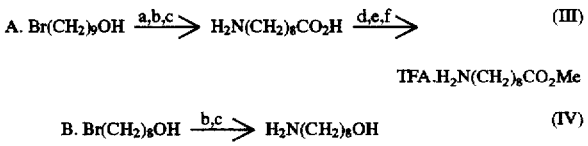

a) Concentrated HNO$_3$;
b) NaN$_3$, DMF, 80–90° C.;
c) Lindlar catalyst, H$_2$, 30° C., 50 psi;
d) Boc$_2$O, 1M NaOH, Na$_2$CO$_3$, dioxan;
e) DCC, MeOH;
f) TFA, DCM;

SCHEME 3

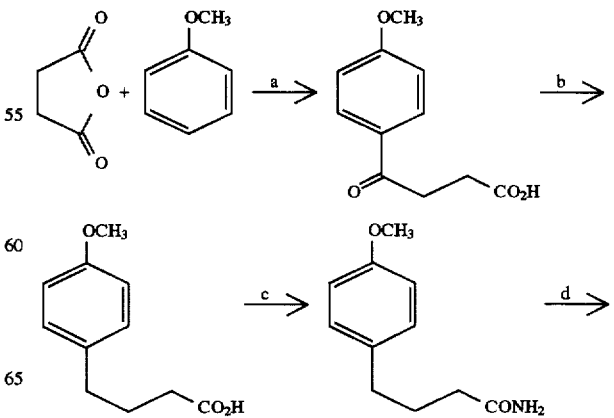

-continued
SCHEME 3

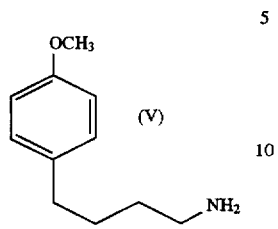

a) AlCl₃, EtNO₂;
b) KOH, N₂H₄, DEG;
c) i) EtOCOCl, Et₃N, EtOAc; ii) NH₃ (g), DMF
d) BMS, THF.

SCHEME 4
BocSPheRαMePheOH  (I)

Example 1

Example 2

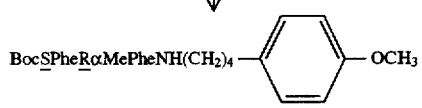
Example 3

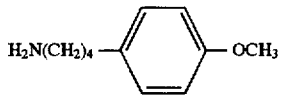

a) i) DCC, HOBt, DMAP, DMF; ii) H₂N(CH₂)₆OH (IV);
b) i) HBTU, DIPEA, DMF; ii) H₂N(CH₂)₄ (V);
c) i) HBTU, DiPEA, DMF; ii) H₂N(CH₂)₈CO₂Me (III);
d) 1M LiOH, dioxan;
e) i) DCC, pentafluorophenol, DCM; ii) NH₃(g), DCM.

SCHEME 5

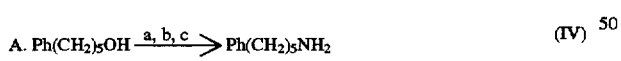

a) Tosyl chloride chloride, pyridine;
b) NaN₃, DMF;
c) Lindlar catalyst, H₂, 30° C., 40 psi.

SCHEME 6

H₂N(CH₂)₇CO₂H —a→

-continued
SCHEME 6

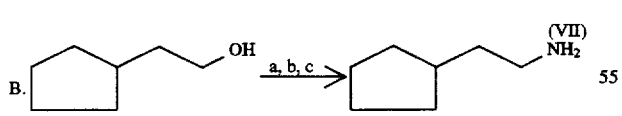

a) Boc₂O, 1 M NaOH, dioxan, Na₂CO₃;
b) 1) EtOCOCl, NMM; ii) LiBH₄, THF;
c) Fluoroboric acid, DCM, TMSCHN₂;
d) TFA, DCM;
e) DCC, MeOH, DMF;
f) TFA, DCM.

SCHEME 7

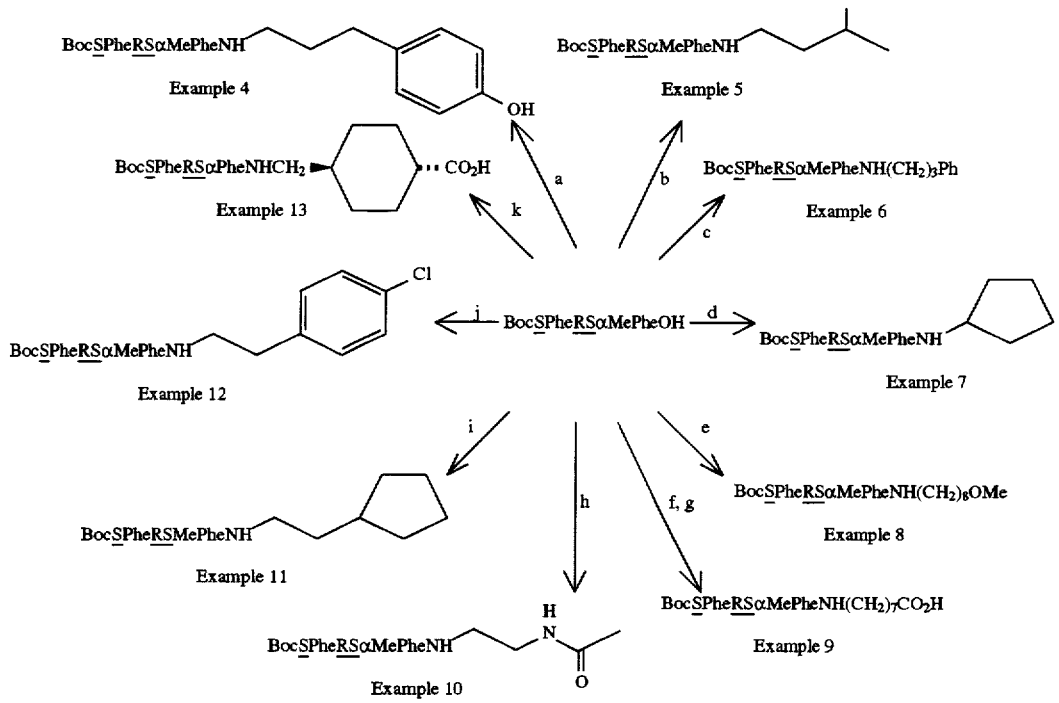

a) i) HBTU, DIPEA, DMF; ii) 3-(4-hydroxyphenyl)-
   propylamine;
b) i) DCC, HOBt, EtOAc; ii) 3-methylbutylamine;
c) i) DCC HOBt, EtOAc; ii) NH$_2$(CH$_2$)$_5$Ph (VI)
d) i) DCC, HOBt, EtOAc; ii) cyclopentylamine;
e) i) HBTU, DIPEA, DMF; ii) TFA.H$_2$N(CH$_2$)$_8$OMe (III);
f) i) HBTU, DIPEA, DMF; ii) TFA.H$_2$N(CH$_2$)$_7$CO$_2$Me (IX);
g) 1 M LiOH, dioxan;
h) i) HBTU, DIPEA, DMF; ii) N-actylethylenediamine;
i) i) HBTU, DIPEA, DMF; ii) cyclopentylethylamine
   (VII);
j) i) HBTU, DIPEA, DMF; ii) 2-(4-chlorophenyl)-
   ethylamine
k) i) HBTU, DIPEA, DMF; ii) trans-4-(aminomethyl)-
   cyclohexane carboxylic acid.

SCHEME 8

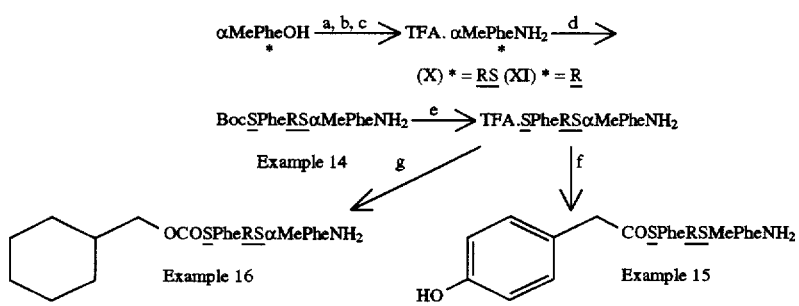

a) Boc$_2$O, 10% Na$_2$CO$_3$, dioxan;
b) i) HOBt, DCC, DMF, ii) NH$_3$(g);
c) TFA;
d) BocPheOpfp, Et$_3$N, EtOAc;
e) TFA;
f) i)HTBU, DIPEA, DMF; ii) 4-hydroxyphenylacetic
   acid;
g) i) cyclohexyl methanol, triphosgene, pyridine, DCM;
   ii) Et$_3$N, DMF.

SCHEME 9

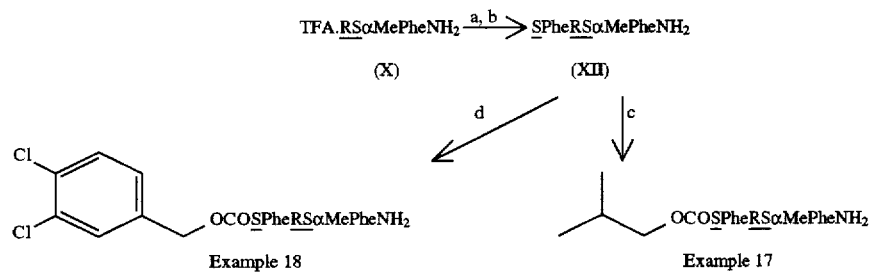

a) Fmoc PheOpfp, Et₃N, DMF;
b) 20% piperidine, DMF;
c) Isobutyl chloroformate, Et₃N, EtOAc;
d) i) 3,4-dichlorobenzylalcohol, triphosgene, pyridine, DCM; ii) Et₃N, EtOAc.

SCHEME 10

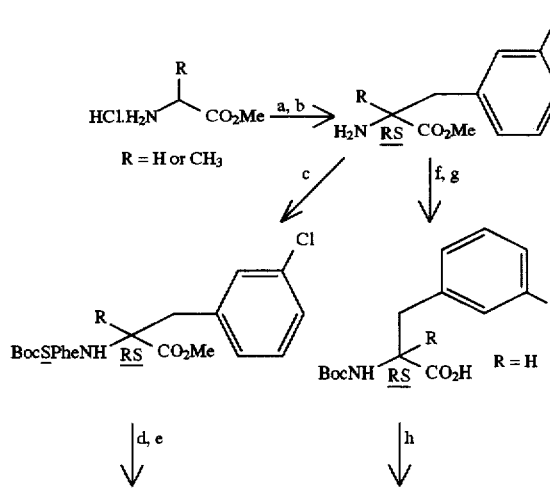

a) 4-nitrophenylchloroformate, DCM, pyridine;
b) TFA.SPheRSαMePheNH₂ (XII), Et₃N, DMF.

SCHEME 11

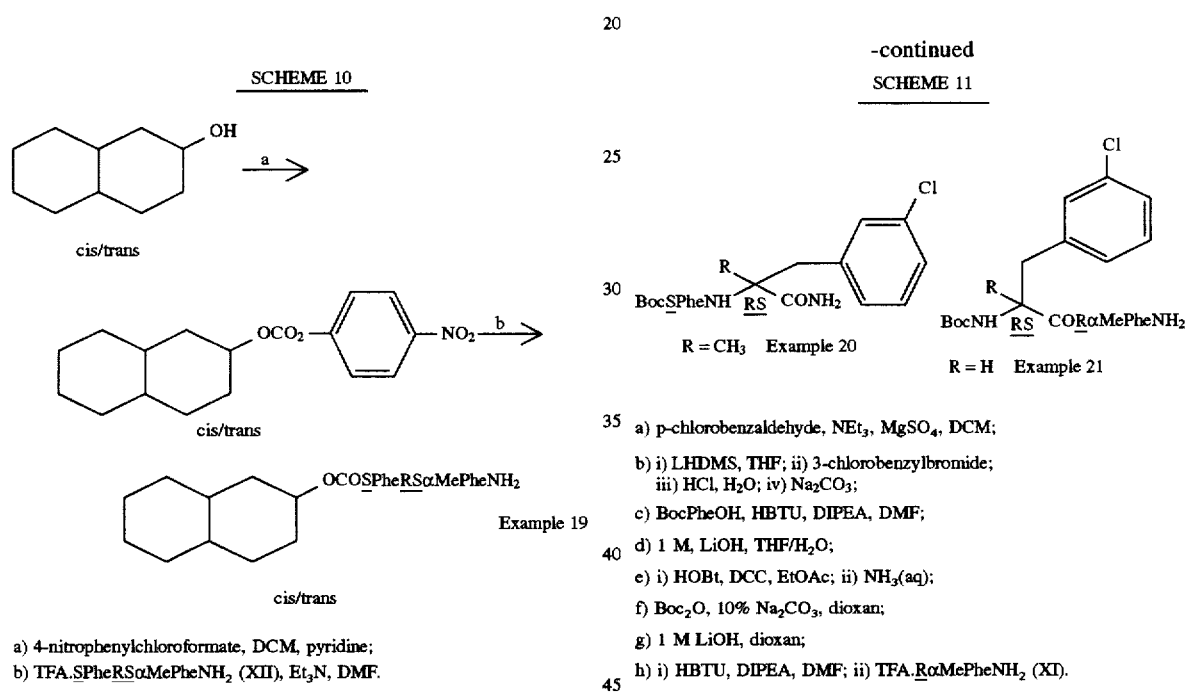

a) p-chlorobenzaldehyde, NEt₃, MgSO₄, DCM;
b) i) LHDMS, THF; ii) 3-chlorobenzylbromide; iii) HCl, H₂O; iv) Na₂CO₃;
c) BocPheOH, HBTU, DIPEA, DMF;
d) 1 M, LiOH, THF/H₂O;
e) i) HOBt, DCC, EtOAc; ii) NH₃(aq);
f) Boc₂O, 10% Na₂CO₃, dioxan;
g) 1 M LiOH, dioxan;
h) i) HBTU, DIPEA, DMF; ii) TFA.RαMePheNH₂ (XI).

SCHEME 12

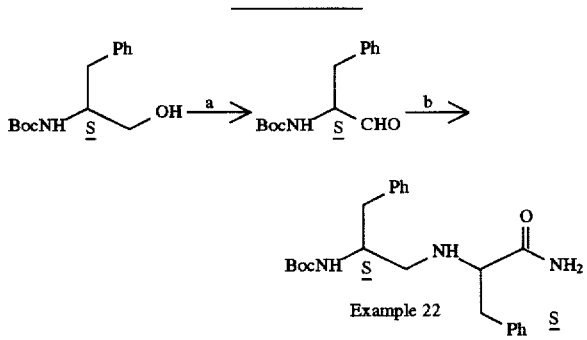

a) i) DMSO, DCM, oxalyl chloride; ii) Et₃N, DCM;
b) NaCNBH₃, SPheNH₂, MeOH/AcOH (99:1).

SCHEME 13

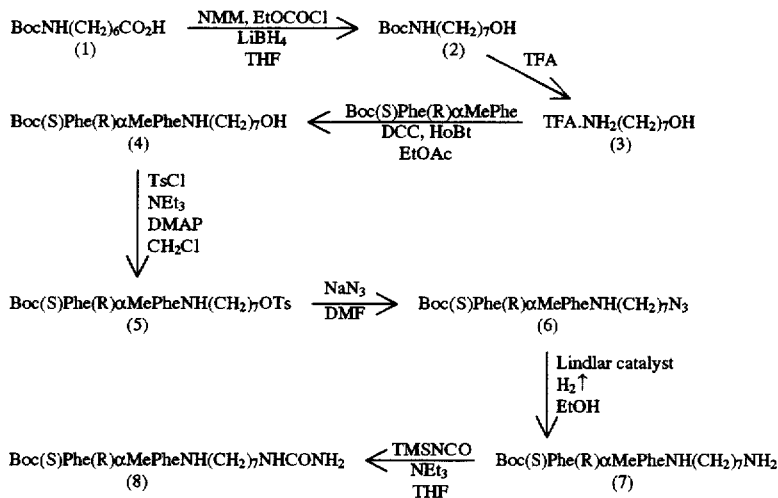

SCHEME 14

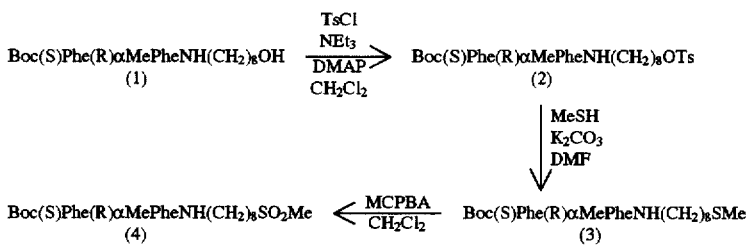

SCHEME 15

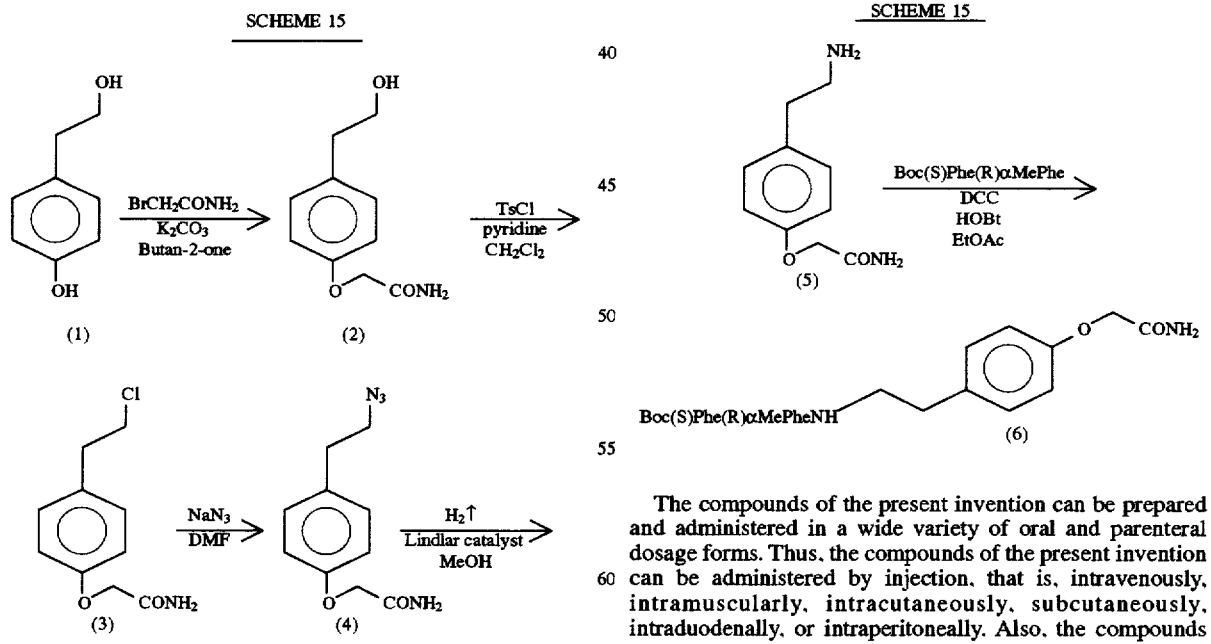

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 50 or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 200 mg preferably 0.5 mg to 100 mg according to the particular application and the potency of the active component. The composition can, if desired, also contain other compatible therapeutic agents.

In therapeutic use the highly selective and competitive antagonists of the NK$_3$ receptor, the compounds utilized in the pharmaceutical method of this invention are administered at the initial dosage of about 0.01 mg to about 500 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The following nonlimiting examples illustrate the methods for preparing the compounds of the invention.

EXAMPLE 1

D-Phenylalaninamide, N-[(1,1-dimethylethoxy) carbonyl]-L-phenylalanyl-N-(8-hydroxyoctyl)-α-methyl-

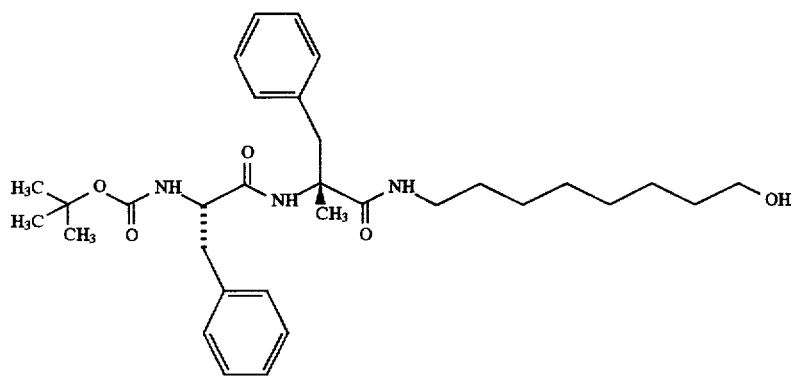

Step 1

RαMePhe→RαMePheOMe

H-α-methyl-[R]-phenylalanine methyl ester

Thionyl chloride (16.2 mL, 225 mmol) was added dropwise over 20 minutes to stirred cooled methanol (120 mL) at −10° C. Following the addition of α-methyl-[R]-phenylalanine (8.08 g, 45 mmol), the mixture was allowed to reach room temperature and stirred for 16 hours. The reaction was then refluxed for 3 hours, cooled, and the methanol removed in vacuo. The residue was taken up in ethyl acetate (300 mL)/saturated aqueous sodium bicarbonate (300 mL). The sodium bicarbonate layer was washed with ethyl acetate and the organic layers combined, washed with water, and dried over magnesium sulphate. The ethyl acetate was removed in vacuo to give 6.72 g (78%) of product as an oil;

IR (film): 3376 (NH), 3030, 2951 (CH), 1732 (C=O); NMR (CDCl$_3$): 1.41 (3H, s, αCH$_3$), 2.71–3.23 (2H, m, βCH$_2$), 3.70 (3H, s, OCH$_3$), 7.13–7.35 (5H, m, aromatics).

Step 2

RαMePheOMe→BocSPheRαMePheOMe t-Butoxycarbonyl-[S]-phenylalanine-α-methyl-[R]-phenylalaninemethyl ester

To a stirred solution of t-butoxycarbonyl-[S]-phenylalanine (8.24 g, 31 mmol) in dimethylformamide (20 mL) was added diisopropylamine (10.74 mL, 62 mmol) and HBTU (11.77 g, 31 mmol). After stirring for 20 minutes at room temperature, α-methyl-[R]-phenylalaninemethyl ester (6 g, 31 mmol) in dimethylformamide was added dropwise over 10 minutes. The reaction was stirred for 5 days. The dimethylformamide removed in vacuo and the residue taken up in ethyl acetate. The ethyl acetate was washed with 2N hydrochloric acid, 10% aqueous sodium bicarbonate, water and brine, dried over magnesium sulphate, and the solvent removed in vacuo. Purification on a flash column using 30% ethyl acetate/hexane increasing to 60% ethyl acetate/hexane gave a white foam, 12.91 g (94%);

NMR (CDCl$_3$): 1.28–1.54 (12H, m, (CH$_3$)$_3$C and αCH$_3$), 2.97–3.37 (4H, m, βCH$_2$×2), 3.72 (3H, s, OCH$_3$), 4.16–4.30 (1H, m, αCH), 5.00 (1H, m, urethane NH), 6.34 (1H, s, amide), 6.93–7.30 (10H, m, aromatics).

Step 3

BocSPheRαMePheOMe→BocSPheRαMePheOH  (I)

t-Butoxycarbonyl-[S]-phenylalanine-α-methyl-[R]-phenylalanine

To a stirred solution of t-butoxycarbonyl-[S]-phenylalanine-α-methyl-[R]-phenylalanine methyl ester (12.91 g, 29 mmol) in 1,4-dioxan was added, dropwise over 45 minutes, a 1M aqueous lithium hydroxide solution (58.5 mL, 58 mmol). The mixture was stirred overnight and the solvents removed in vacuo. The residue was partitioned between ethyl acetate (200 mL) and water (500 mL). The aqueous layer was acidified to pH 3 with 2M hydrochloric acid (~29 mL) and extracted with ethyl acetate (3×200 mL). The organic layers were washed with water, dried over magnesium sulphate, and evaporated to give a white solid, 10.35 g (83%), mp 123°–128° C.; [α]$_D^{21}$=+6.0° C. (C=0.68 in MeOH);

NMR (CDCl$_3$): 1.34 (9H, s, (CH$_3$)$_3$C), 1.58 (3H, s, αCH$_3$), 2.91–2.94 (2H, m, βCH$_2$), 3.24, 3.37 (2H, 2×d, J=13.6 Hz, βCH$_2$), 4.45–4.55 (1H, m, αCH), 5.18–5.28 (1H, m, urethane), 6.70 (1H, s, amide), 7.06–7.29 (10H, m, aromatics) IR (film) 3322 (NH), 2925 (CH), 1709 (urethane, C=O), 1660 (amide I).

Step 4

Br(CH$_2$)$_8$OH→N$_3$(CH$_2$)$_8$OH

8-Azido-octan-1-ol

8-Bromo-octan-1-ol (2.61 g, 12.5 mmol) was dissolved in Dmf (30 mL) and sodium azide (0.89 g, 13.75 mmol) was added. The reaction was heated to 90° C. and stirred overnight. The solution was then cooled to room temperature and poured onto ice. The aqueous was extracted with DCM (3×200 mL) and the combined extracts were washed with brine (2×200 mL), then dried over MgSO$_4$. The solution was filtered and the solvent was removed in vacuo to give a yellow oil, 1.99 g (93% yield);

IR (film): 3355, 2932, 2858, and 2096 cm$^{-1}$; NMR (CDCl$_3$): δ 1.34–1.59 (8H, m, CH$_2$×4), 3.25 (2H, t, J=7 Hz, CH$_2$N$_3$), 3.64 (2H, t, J=6.6 Hz, CH$_2$OH).

Step 5

N$_3$(CH$_2$)$_8$OH→H$_2$N(CH$_2$)$_8$OH  (IV)

8-amino-octan-1-ol

8-Azido-octan-1-ol (1.99 g, 11.6 mmol) was dissolved in ethanol (25 mL) and Lindlar catalyst (200 mg) was added. The solution was hydrogenated at 50 psi, 30° C. for 2 hours. The catalyst was removed by filtration through Kieselguhr and the solvent was removed in vacuo to give a white solid 1.33 g (79% yield), mp 48°–53° C.;

IR (film): 3346, 2927, 2855, 1610, 1597, and 1485 cm$^{-1}$; NMR (CDCl$_3$): δ 1.32–1.58 (13H, m, CH$_2$×6, OH), 2.68 (2H, t, J=6.9 Hz, CH$_2$NH$_2$), 3.62 (2H, t, J=6.6 Hz, CH$_2$OH).

Step 6

BocSPheRαMePheOH→BocSPheRαMePheNH(CH$_2$)$_8$OH

Boc-SPheRαMePheNH(CH$_2$)$_8$OH

BocSPheRαMePheOH (1.71 g, 4 mmol) was dissolved in DMF (10 mL) and DCC (0.83 g, 4 mmol) added. 1-Hydroxybenzotriazole (0.54 g, 4 mmol) was added and the solution was stirred for 5 minutes. 8-Amino-octan-1-ol (0.64 g, 4.4 mmol) and a catalytic amount of DMAP was added and the reaction was stirred for 24 hours. The precipitate was removed by filtration and the filtrate concentrated in vacuo. The residue was redissolved in EtOAc (100 mL) and washed with dilute HCl (3×100 mL), 10% NaHCO$_3$ (3×100 mL), water (3×100 mL), and brine (100 mL). The organic was dried over MgSO$_4$, filtered, and the solvent then removed in vacuo. The product was purified by medium pressure, reverse phase chromatography 0% to 100% MeOH in water over 30 minutes, to give a white solid 1.51 g (68%), mp 43°–45° C.;

[α]$_D^{19.8}$=+9.9° C. (C=1.1 in MeOH); IR (film): 3339, 2931, 2856, 1686, 1652, and 1524 cm$^{-1}$; NMR (CDCl$_3$): δ 1.29–1.57 (24H, m, BocCH$_3$×3, αCH$_3$, CH$_2$×6), 2.70–3.45 (6H, m, βCH$_2$×2, CONHCH$_2$), 3.65 (2H, m, CH$_2$OH), 4.00 (1H, m, αCH), 4.95 (1H, br.d, urethane NH), 5.85 (1H, s, amide NH), 6.65 (1H, s, amide NH), 6.95–7.34 (10H, m, aromatics); MS (CI): 554 (M$^+$), 454, 134; Analysis calculated for C$_{32}$H$_{47}$N$_3$O$_5$: C, 69.41; H, 8.55; N, 7.59. Found: C, 69.25; H, 8.23; N, 7.52.

EXAMPLE 2

D-Phenylalaninamide, N-[(1,1-dimethylethoxy)carbonyl]-L-phenylalanyl-N-(9-amino-9-oxononyl)-α-methyl-

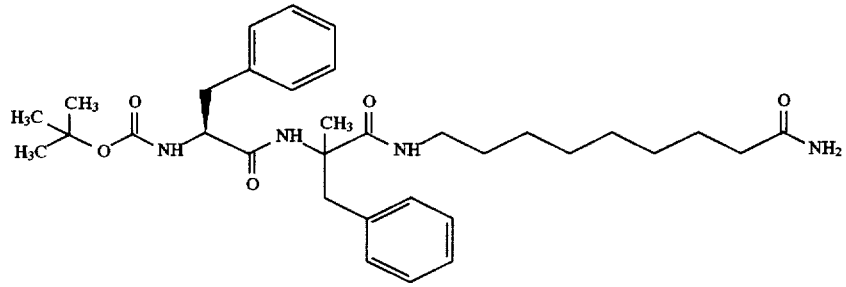

Step 1

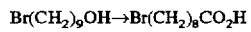

9-Bromo-nonanoic acid

9-Bromo-1-nonanol (4 g, 18 mmol) was placed in a flask, cooled on an ice bath, and concentrated nitric acid (40 mL) was slowly added. The solution was stirred at 0° C. for 30 minutes then allowed to warm to room temperature and stirring continued overnight. The solution was poured onto ice and extracted with DCM (3×150 mL). The combined extracts were washed with water (3×150 mL) and the solvent then removed in vacuo to give an oil 3.82 g (94%);

IR (film): 2932, 2857, 1709 cm$^{-1}$; NMR (CDCl$_3$): 1.25–1.48 (8H, m, CH$_2$×4), 1.62 (2H, m, CH$_2$), 1.83 (2H, m, CH$_2$), 2.35 (2H, t, C$\underline{H}_2$CO$_2$H), 3.39 (2H, t, C$\underline{H}_2$Br).

Step 2

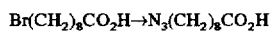

9-Azido-nonanoic acid

9-Bromo-nonanoic acid (3.82 g, 17 mmol) was dissolved in DMF (30 mL) and sodium azide (1.11 g, 17 mmol) was added. The solution was heated to 80° C. and stirred overnight. The reaction was poured onto ice and extracted with DCM (3×200 mL). The combined extracts were washed with water (3×200 mL), brine (200 mL), and dried over MgSO$_4$. The solvent was removed in vacuo to give a clear oil 2.83 g (84% yield);

IR (film): 2934, 2858, 2098, and 1706 cm$^{-1}$.

Step 3

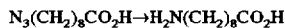

9-Amino-nonanoic acid

9-Azido-nonanoic acid (2.83 g, 14.2 mmol) was dissolved in ethanol (30 mL) and Lindlar catalyst (300 mg) added. The solution was hydrogenated at 50 psi, 30° C. for 4 hours, after which the catalyst was removed by filtration through Kieselguhr, washing with methanol. The solvent was removed in vacuo to give a pale yellow solid, 1.7 g (70%);

IR (film): 2925, 2854, and 1558 cm$^{-1}$; NMR (CD$_3$OD): δ 1.31–1.45 (8H, m, CH$_2$×4), 1.55–1.70 (4H, m, CH$_2$×2), 2.35 (2H, t, C$\underline{H}_2$CO$_2$H), 2.88 (2H, t, C$\underline{H}_2$NH$_2$).

Step 4

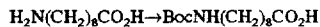

9-Amino-nonanoic acid (1 g, 5.8 mmol) was dissolved in 1M NaOH (6.4 mL) and di-tert-butyldicarbonate (1.4 g, 6.4 mmol) in dioxan (7 mL) was added. Na$_2$CO$_3$ (1.83 g, 6.4 mmol) was added and the solution was stirred overnight. The reaction was concentrated in vacuo and the residue was redissolved in water. The aqueous was washed with ether, the pH was then adjusted to four with dilute HCl. The aqueous was then extracted with EtOAc (3×200 mL). The combined extracts were washed with water (3×200 mL), brine (200 mL), and dried over MgSO$_4$. After filtration, the solvent was removed in vacuo to give a yellow oil 1.14 g (72%);

IR (film): 3339, 2932, 2858, and 1714 cm$^{-1}$; NMR (CDCl$_3$): δ 1.20–1.65 (21H, m, BocCH$_3$×3, CH$_2$×6), 2.33 (2H, m, C$\underline{H}_2$CO$_2$H), 3.11 (2H, m, NHC$\underline{H}_2$), 4.60 (1H, s, NH).

Step 5

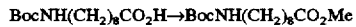 (III)

BocNH(CH$_2$)$_8$CO$_2$H (1.02 g, 3.7 mmol) was dissolved in methanol (20 mL) and DCC (0.75 g, 3.7 mmol) added. A catalytic amount of DMAP was added and the reaction was stirred for 48 hours. The precipitate was removed by filtration and the solvent was removed in vacuo to give an oil 1.33 g. The crude product was used without purification.

Step 6

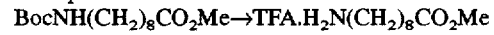

BocNH(CH$_2$)$_8$CO$_2$Me (1.33 g, 4.6 mmol) was dissolved in a 50:50 mixture of DCM/TFA (20 mL). The solution was stirred for 1 hour after which the solvent was removed in vacuo. A partial purification was carried out using medium pressure reverse phase chromatography 0–100% MeOH in H$_2$O, yield 0.78 g (56%);

IR (film): 2934, 2858, 1736, and 1682 cm$^{-1}$.

Step 7

BocSPheRαMePheOH (I, prepared Example 1, Step 3) (0.85 g, 2 mmol) was dissolved in DMF (10 mL) and HBTU (0.76 g, 2 mmol) and DIPEA (348 µL, 2 mmol) were added. The solution was stirred for 10 minutes, after which the trifluoroacetate salt of H₂N(CH₂)₈CO₂Me (0.78 g, 2.5 mmol) was added. DIPEA (790 µL, 4.5 mmol) was added and the reaction was stirred overnight. The solution was concentrated in vacuo and the residue was redissolved in EtOAc (100 mL). The organic was washed with dilute HCl (3×100 mL), saturated NaHCO₃ (3×100 mL), water (3×100 mL), and brine (100 mL) then dried over MgSO₄. After filtration the solvent was removed in vacuo and the residue was purified by chromatography. Sorbsil 60, 2% MeOH/DCM. A white solid was isolated 350 mg, which was shown to be a mixture of the required product and the BocSPhe RαMePheNH(CH₂)₇CO₂Me analog;

IR (film): 3343, 2978, 2932, 2857, 1735, 1689, 1650; and 1520 cm⁻¹; NMR (CDCl₃): δ 1.27–1.62 (24H, m, BocCH₃× 3, αCH₃, CH₂×6), 2.29 (2H, t, CH₂CO₂R), 2.68–3.43 (6H, m, CONHCH₂, βCH₂×2), 3.65 (3H, s, OCH₃), 4.01 (1H, m, αCH), 5.00 (1H, s, urethane NH), 5.95 (1H, s, NH), 6.70 (1H, s, NH), 6.96–7.36 (10H, m, aromatics); HPLC: 40–100% B over 20 minutes, A=H₂O, B=CH₃CN, 0.1% TFA, R$_t$=16.8 and 17.8 minutes.

Step 8

The methyl esters (Step 7) (370 mg, 0.6 mmol) were dissolved in dioxan (3.6 mL) and 1M LiOH (1.2 mL), the solution was stirred for 2 hours. The solvent was removed in vacuo and the residue was redissolved in water, then washed with ether. The pH of the aqueous was adjusted to four with dilute HCl and then extracted with DCM (3×100 mL). The combined extracts were washed with water (3×100 mL) and brine (100 mL), dried over MgSO₄, filtered, and the solvent removed in vacuo. The crude product was purified by medium pressure reverse phase chromatography 80% MeOH in H₂O to give a white solid 290 mg, again a mixture of the C₈ and C₉ chains;

NMR (CDCl₃): δ 1.22–1.70 (24H, m, BocCH₃×3, αCH₃, CH₂×6), 2.35 (2H, t, CH₂CO₂H), 2.75–3.48 (6H, m, βCH₂× 2, CONHCH₂), 4.02–4.15 (1H, m, αCH), 4.95, 5.08 (1H, 2×br S, urethane NH), 5.90, 5.95 (1H, 2×S, amide NH's), 6.60 (1H, br S, amide NH), 6.95–7.38 (10H, m, aromatics); HPLC: 40–100% B over 20 minutes, A=H₂O, B=CH₃CN, 0.1% TFA, R$_t$=13.6 and 14.5 minutes.

Step 9

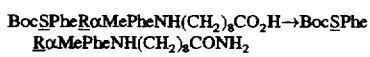

The mixture of acids (Step 8) (290 mg, 0.5 mmol) was dissolved in DCM (3 mL) and DCC (103 mg, 0.5 mmol) followed by pentafluorophenol (92 mg, 0.5 mmol) added. The reaction was stirred overnight, then the precipitate removed by filtration. The solvent was removed in vacuo and the ester redissolved in DCM (3 mL). Ammonia was bubbled through the solution for 5 minutes and the solvent then removed in vacuo, to give a crude product 210 mg. Purification was carried out by reverse phase HPLC 57–67% B over 40 minutes, A=H₂O, B=CH₃CN, 0.1% TFA to give a white solid 93 mg (32%), mp 45°–47° C.;

IR (film): 3340, 2932, 1698, 1656, and 1528 cm⁻¹; MS (FAB) 603 (M+Na), 581 (M+H), 481, 334, 173, 134; NMR (CDCl₃) δ 1.29–1.48 (22H, m, BocCH₃×3, αCH₃, CH₂×5), 1.65 (2H, m, CH₂), 2.26 (2H, t, CH₂CONH₂), 2.70–3.45 (6H, m, βCH₂×2, CONHCH₂), 4.0 (1H, m, αCH), 4.95 (1H, m, urethane NH), 5.90 (1H, s, amide NH), 6.05, 6.35 (2H, 2×S, CONH₂), 6.75 (1H, s, amide NH), 6.96–7.37 (10H, m, aromatics); HPLC: 40–100% B over 20 minutes, A=H₂O, B=CH₃CN, 0.1% TFA, R$_t$=12.0 minutes; Analysis calculated for C₃₃H₄₈N₄O₅·0.7 TFA: C, 62.54; H, 7.43; N, 8.48. Found: C, 62.24; H, 7.50; N, 8.48.

EXAMPLE 3

D-Phenylalaninamide, N-[(1,1-dimethylethoxy) carbonyl]-L-phenylalanyl-N-[4-(4-methoxyphenyl) butyl-α-methyl-

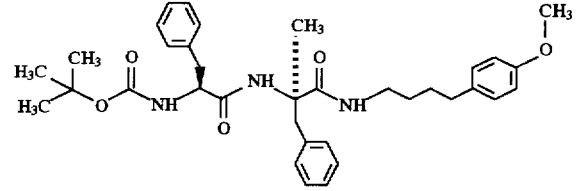

Step 1

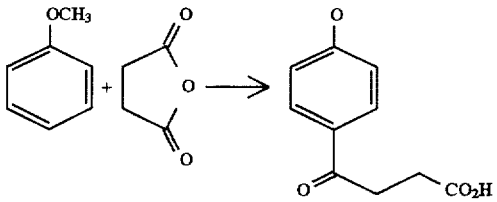

Anhydrous aluminium chloride (8.00 g, 60 mmol) and succinic anhydride (3.00 g, 30 mmol) in nitroethane (80 mL) were stirred under N₂ at 0° C. for 1 hour. Anisole (3.26 mL, 30 mmol) was added dropwise over 5 minutes. The resulting mixture was stirred below 15° C. for 6 hours and then at room temperature for 15 hours.

The deep red solution was poured onto 200 mL crushed ice containing 100 mL 2M HCl and 10 mL concentrated HCl, and stirred vigorously for 1.5 hours. Extraction with DCM, drying (MgSO₄), and purification by flash chromatography using ethyl acetate:hexane (1:1) gave a white solid (3.48 g, 56%);

M/e (CI): 191 (100%), 209 (M+1); NMR (CDCl₃): δ 2.80 (2H, t, —CH₂—), 3.26 (2H, t, —CH₂—), 3.87 (3H, s, —OCH₃), 6.93 (2H, d, Ar), 7.95 (2H, d, Ar).

Step 2

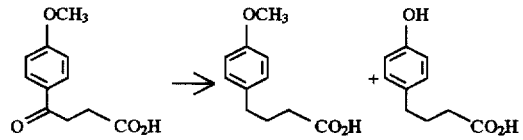

Hydrazine monohydrate (1.61 mL, 33.2 mmol), the ketone (3.46 g, 16.6 mmol) and potassium hydroxide pellets (3.77 g, 66.4 mmol) were heated under reflux in diethylene glycol (20 mL) for 1.5 hours. The temperature was then increased to 180° C. for 2 hours during which time the hydrazine and water distilled over. On cooling, an additional 1.61 mL hydrazine hydrate was added and the process was repeated.

On completion, 10% citric acid solution (130 mL) was added and the mixture was extracted with ether. The ether layer was washed with water and dried (MgSO$_4$) and further purified by column chromatography in ether:hexane (2:3) yielding a white solid (2.30 g, 71%);

IR (film): 1707 and 2936 cm$^{-1}$; M/e (CI): 177 (100%), 194 (M); NMR (CDCl$_3$): δ 1.93 (2H, quint, —CH$_2$—), 2.35 (2H, t, —CH$_2$—), 2.61 (2H, t, —CH$_2$—), 3.78 (3H, s, —OCH$_3$), 6.82 (2H, d, Ar), 7.08 (2H, d, Ar);

Step 3

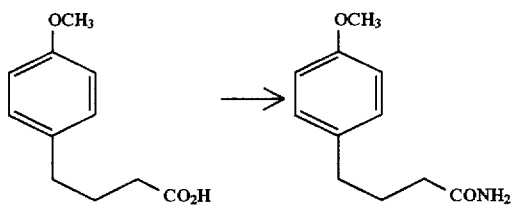

4-(4-Methoxyphenyl)butanoic acid (1.18 g, 6.07 mmol) and triethylamine (0.847 mL, 6.07 mmol) were dissolved in DCM (40 mL) at 0° C. Ethyl chloroformate (0.581 mL, 6.07 mmol) was added dropwise and the resulting solution was stirred at 0° C. for 45 minutes. DMF (10 mL) was added and a slow stream of ammonia gas was bubbled through the solution for 45 minutes. The resulting mixture was stirred for 18 hours at room temperature.

On removal of the solvents, the residue was taken up in ethyl acetate and washed with water, 2M HCl, and 10% Na$_2$CO$_3$ solution. Drying (MgSO$_4$) and evaporation gave an off-white solid (0.86 g, 73%);

IR (film): 3363, 1659, and 1629 cm$^{-1}$; M/e (CI): 194 (M+1); NMR (DMSO-d$_6$): δ 1.72 (2H, quint, —CH$_2$—), 2.03 (2H, t, —CH$_2$—), 2.48–2.51 (2H, obs by DMSO, —CH$_2$—), 3.71 (3H, s, —OCH$_3$), 6.71 (1/2×2H, bs), 7.24 (1/2×2H, bs, —CONH$_2$), 6.80–7.12 (4H, m, Ar).

Step 4

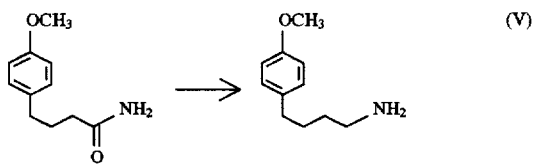

(V)

2M BMS in THF (4.8 mL, 9.66 mmol) was added dropwise over 15 minutes to a solution of 4-(4-methoxyphenyl)butanamide (0.80 g, 4.14 mmol) in THF (30 mL) at room temperature under N$_2$. The resulting mixture was stirred at room temperature for 1.5 hours and heated at reflux for 5 hours. On cooling to 0° C., methanol (2 mL) was added dropwise, the temperature was not allowed to rise above 15° C. The mixture was allowed to stir for 2 days. HCl (g) was bubbled through the solution for ~3 minutes and the resulting solution was heated at reflux for 1 hour.

On cooling, the mixture was evaporated to dryness and the residue was partitioned between water and ethyl acetate. The aqueous layer was adjusted to pH 10 with NaOH and extracted with ethyl acetate. Drying (MgSO$_4$) and further purification by flash chromatography using 10% MeOH/DCM gave a white solid (0.230 g, 31%);

NMR (DMSO-d$_6$): 1.28–1.44 (2H, m, —CH$_2$—), 1.43–1.62 (2H, m, —CH$_2$—), 2.44–2.60 (4H, obs, by DMSO, 2×—CH$_2$—), 3.71 (3H, s, —OCH$_3$), 6.80–7.11 (4H, m, Ar).

Step 5

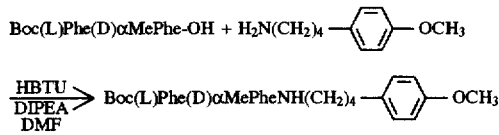

Boc(L)Phe(D)αMePhe-OH (I, from Example 1, Step 3) (0.247 g, 0.58 mmol), HBTU (0.220 g, 0.58 mmol), and diisopropylethylamine (0.280 mL, 1.16 mmol) were stirred together in DMF (5 mL) at room temperature for 20 minutes. 4-(4-Methoxyphenyl)butyl amine (0.104 g, 0.58 mmol) in DMF (2 mL) was then added. The mixture was stirred for 24 hours at room temperature.

On removal of the DMF, the residue was taken up in ethyl acetate and washed with 2M HCl, 1M NaOH, and water. Drying (MgSO$_4$) and further purification by flash chromatography using 2.5% MeOH/DCM gave a white solid (0.223 g, 65%). mp 44°–48° C.;

[α]$_D^{T=26.4}$=+4.26 (C=1.01, MeOH); IR (film): 3334, 2932, 1683, and 1652 cm$^{-1}$; M/e (CI): 588 (M+1), 134 (100%); NMR (DMSO-d$_6$): δ 1.10–1.50 (16H, m, Boc, αMe, —CH$_2$—×2), 2.40–2.50 (2H, obs by DMSO, —CH$_2$—), 2.60–3.20 (6H, m, 4×β-CH$_2$—, —CH$_2$—), 3.65 (3H, s, —OCH$_3$), 4.12 (1H, m, αH), 6.75–7.25 (15H, m, Ar, —OCONH—), 7.51 (1H, t, —CONH—CH$_2$—), 7.71 (1H, s, —CONH—); Analysis calculated for C$_{35}$H$_{45}$N$_3$O$_5$: C, 71.52; H, 7.72; N, 7.15. Found: C, 71.19; H, 7.82; N, 7.09.

EXAMPLE 4

DL-Phenylalaninamide, N-[(1,1-dimethylethoxy) carbonyl]-L-phenylalanyl-N-[3-(4-hydroxyphenyl) propyl]-α-methyl-

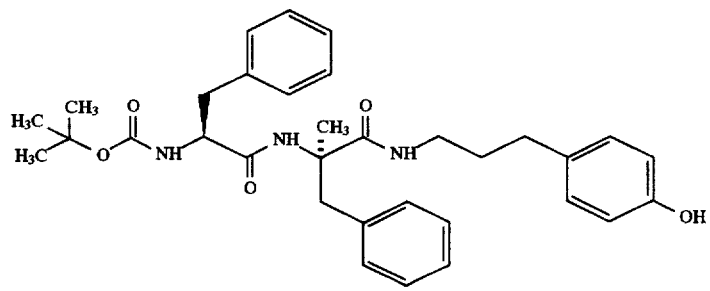

Step 1

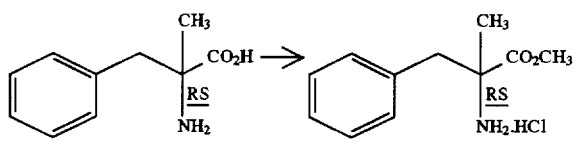

Thionyl chloride (10.1 mL, 140 mmol) was added dropwise over 5 minutes to MeOH (100 mL) stirred in a cooling bath at −10° C. RS-α-MePheOH (5.0 g, 27.9 mmol) was added at −10° C. and the solution stirred overnight with slow rewarming to room temperature. The solution was heated at reflux for 1 hour, allowed to cool, and the solvent removed in vacuo to give the product as an off-white amorphous solid (6.49 g, 100%);

NMR (DMSO-$d_6$): δ 1.53 (3H, s, C$\underline{H}_3$), 3.13 (1H, d, J=13.7 Hz, PhC$\underline{H}$H), 3.22 (1H, d, J=13.7 Hz, PhCH$\underline{H}$), 3.71 (3H, s, COOC$\underline{H}_3$), 7.16–7.36 (5H, m, C$_6\underline{H}_5$), 8.80 (3H, b, N$^+$H$_3$).

Step 2

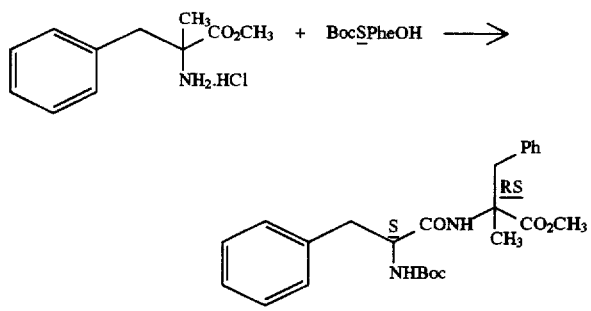

N,N'-dicyclohexylcarbodiimide (2.27 g, 11.0 mmol) was added to a stirred solution of N-tert-butyloxycarbonyl-S-phenylalanine (2.65 g, 10 mmol) and 1-hydroxybenzotriazole monohydrate (1.91 g, 12.5 mmol) in EtOAc (100 mL). The mixture was stirred at room temperature for 2 hours and the N,N'-dicyclohexylurea filtered off. Et$_3$N (1.53 mL, 11 mmol) was added followed by a solution of the amino ester hydrochloride (2.30 g, 10 mmol) in EtOAc (25 mL) added dropwise over 10 minutes and the mixture stirred at room temperature for 18 hours. The solution was washed with 5% citric acid solution (2×25 mL), saturated NaHCO$_3$ solution (2×25 mL), 5% citric acid solution (25 mL), and once with brine (25 mL). The EtOAc solution was dried over MgSO$_4$, filtered, and the solvent removed in vacuo. The residue was purified by chromatography on silica using 67% n-hexane/33% EtOAc as eluant giving the product as a white solid (1.99 g, 45%), mp 40°–46° C.;

IR (film): 3332, 1741, and 1664 cm$^{-1}$; NMR (CDCl$_3$): δ 1.37, 1.40 (9H, 2s, C(C$\underline{H}_3$)$_3$), 1.54 (3H, s, C$\underline{H}_3$), 2.93–3.16 (3H, m, PhC$\underline{H}_2$, PhC$\underline{H}$H), 3.32–3.44 (1H, m, PhCH$\underline{H}$), 3.71, 3.72 (3H, 2s, CO$_2$C$\underline{H}_3$), 4.20–4.35 (1H, m, CH$_2$C$\underline{H}$), 5.00 (1H, b, N$\underline{H}$COO), 6.38 (1H, d, J=9.0 Hz, CON$\underline{H}$), 6.88–6.96 (2H, m, Ph), 7.15–7.32 (8H, m, Ph); Analysis calculated for C$_{25}$H$_{32}$N$_2$O$_5$·0.25H$_2$O.

Step 3

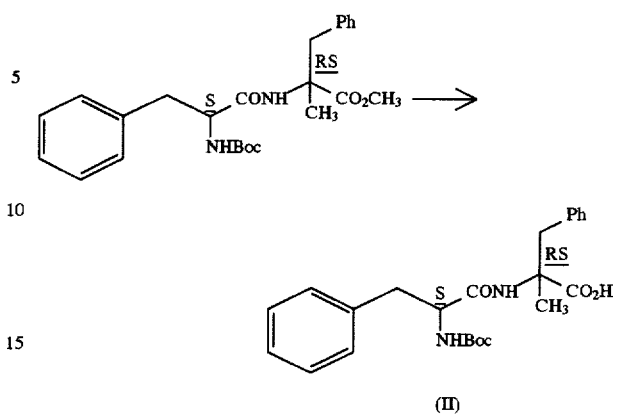

(II)

1N LiOH solution (4.34 mL, 4.34 mmol) was added dropwise over 30 minutes to a stirred solution of the methylester (1.74 g, 3.95 mmol) in THF:H$_2$O (50 mL, 4:1 mixture) cooled to 0° C. The mixture was stirred with slow rewarming to room temperature for 4 days and then the THF removed in vacuo. The residue was diluted with water (25 mL) and extracted once with EtOAc (25 mL). The remaining aqueous solution was acidified with 5% citric acid solution and the product extracted into EtOAc (2×25 mL). The combined EtOAc extracts were dried over MgSO$_4$, filtered, and the solvent removed in vacuo giving the product as a white solid (1.04 g, 62%), mp 106.8°–107.7° C.;

IR (film): 1719 and 1662 cm$^{-1}$; NMR (DMSO-d$^6$): δ 1.20–1.36 (12H, m, C(C$\underline{H}_3$)$_3$, C$\underline{H}_3$), 2.66–2.74 (1H, m, PhC$\underline{H}$H), 2.93–3.35 (3H, m, PhC$\underline{H}_2$, PhCH$\underline{H}$), 4.10–4.22 (1H, m, CH$_2$C$\underline{H}$), 6.93–7.01 (1H, m, N$\underline{H}$COO), 7.07–7.27 (10H, m, 2C$_6\underline{H}_5$), 7.63, 7.90 (1H, 2s, CON$\underline{H}$), 12.65 (1H, b, COO$\underline{H}$); Analysis calculated for C$_{24}$H$_{30}$N$_2$O$_5$·0.25H$_2$O:

Step 4

BocSPheRSαMePheOH ⟶

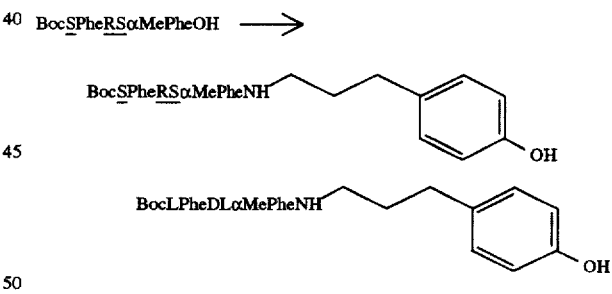

To a stirred solution of Boc-L-Phe-DL-αMePhe (II) (0.20 g, 0.47 mmol) in dimethylformamide (5 mL) was added HBTU (0.18 g, 0.47 mmol), diisopropylethylamine (0.12 g, 0.94 mmol), and 3-(4-hydroxyphenyl)propylamine (0.07 g, 0.47 mmol). The reaction was stirred at room temperature for 20 hours and then concentrated under reduced pressure. The residue was taken up in ethyl acetate and the organic layer washed with 0.1N hydrochloric acid, dried over magnesium sulphate, and the solvent removed in vacuo. Purification by column chromatography gave the product as a white amorphous solid, 0.04 g (15%), mp 57°–60° C.;

IR (film): 3338 (NH), 2933 (CH), 1689 (urethane, C=O), 1652 (amide I), 1516 (amide II); NMR (CDCl$_3$): 1.30, 1.35 (9H, 2×s, (C$\underline{H}_3$)$_3$C), 1.47, 1.57 (3H, 2×s, αC$\underline{H}_3$), 1.69–1.79 (2H, m, CH$_2$C$\underline{H}_2$CH$_2$), 2.47–2.54 (2H, m, C$\underline{H}_2$-Ph), 2.69–3.38 (6H, m, βCH$_2$×2, NHC$\underline{H}_2$), 3.97–4.15 (1H, m, αCH), 4.90, 5.04 (1H, 2×d, J=5.5 and 5.7 Hz, urethane NH), 5.82, 6.18 (1H, 2×s, amide), 6.55–6.70 (1H, m, amide), 6.71–6.77 (2H, m, aromatics), 6.91–6.97 (4H, m, aromatics), 7.13–7.35 (8H, m, aromatics); Analysis calculated for $C_{33}H_{41}N_3O_5 \cdot 0.25H_2O$.

EXAMPLE 5

DL-Phenylalaninamide, N-[(1,1-dimethylethoxy) carbonyl]-L-phenylalanyl-α-methyl-N-3-methylbutyl-

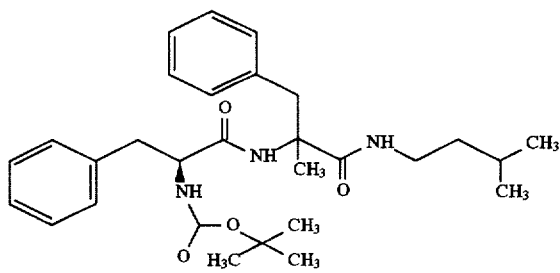

Step 1

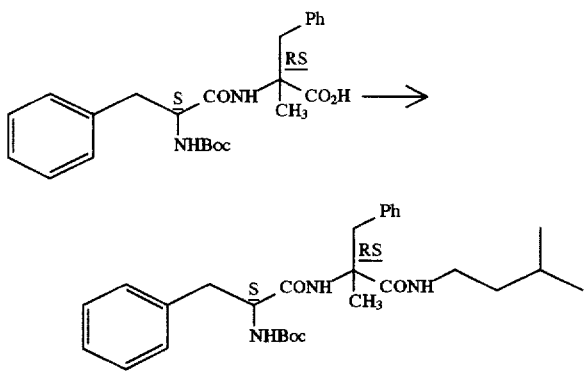

N,N'-dicyclohexylcarbodiimide (0.129 g, 0.63 mmol) was added to a stirred solution of the acid (II, from Example 4, Step 3) (0.242 g, 0.57 mmol) and 1-hydroxybenzotriazole monohydrate (0.105 g, 0.68 mmol) in EtOAc (25 mL). The mixture was stirred at room temperature for 2 hours and the N,N'-dicyclohexylurea filtered off. Isoamylamine (0.075 g, 0.86 mmol) in EtOAc (2 mL) was added dropwise over 2 minutes and the mixture stirred at room temperature for 18 hours. The solution was washed with 5% citric acid solution (2×25 mL), saturated NaHCO₃ (2×25 mL), 5% citric acid (25 mL), and once with brine (25 mL). The EtOAc solution was dried over MgSO₄, filtered, and the solvent removed in vacuo. The residue was purified by chromatography on silica using 67% n-hexane 33% EtOAc and then 50% n-hexane/ 50% EtOAc as eluant to give the product as a white solid (0.123 g, 44%); mp 80°–93° C.;

IR (film): 3332, 2958, 1689, and 1651 cm⁻¹; NMR (CDCl₃): δ 0.89 (6H, d, J=6.6 Hz, (CH₃)₂CH), 1.33, 1.37 (9H, 2s, NHCOOC(CH₃)₃), 1.25–1.44 (2H, m, CC H₂CH(CH₃)₂), 1.49, 1.58 (3H, 2s, CH₃), 1.52–1.64 (1H, m, CH₂CH₂CH(CH₃)₂), 2.77–3.44 (6H, m, 3CH₂), 4.00–4.13 (1H, m, CH₂ CHNCO), 4.87–4.98 (1H, m, N HCOOC(CH₃)3), 5.92, 6.26 (1H, 2s, CONH), 6.54, 6.67 (1H, 2s, CONH), 6.96–6.98 (2H, m, Ph), 7.16–7.36 (8H, m, Ph); Analysis calculated for $C_{29}H_{41}N_3O_4$: C, 70.27; H, 8.34; N, 8.48. Found: C, 70.37; H, 8.56; N, 8.19.

EXAMPLE 6

DL-Phenylalaninamide, N-[(1,1-dimethylethoxy) carbonyl]-L-phenylalanyl-α-methyl-N-(5-phenylpentyl)-

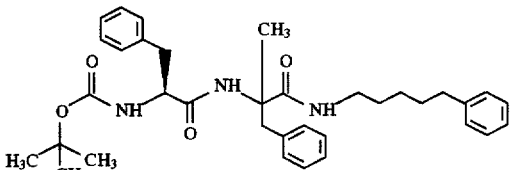

Step 1

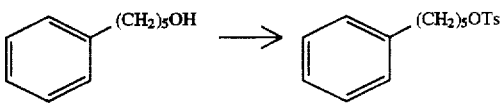

Triethylamine (0.354 g, 3.50 mmol) was added to a stirred solution of the alcohol (0.500 g, 3.04 mmol) and p-toluene sulfonyl chloride (0.608 g, 3.19 mmol) in CH₂Cl₂ (5 mL). The mixture was stirred overnight at room temperature and then washed with 0.1M HCl solution and saturated NaHCO₃ solution. The CH₂Cl₂ layer was dried (MgSO₄), filtered, and the solvent removed in vacuo. Purification of the residue by chromatography on silica using 25% EtOAc/75% n-hexane as eluant gave the product as a colorless gum (0.538 g, 56%);

IR (film): 2993, 2859, 1359, and 1176 cm⁻¹; NMR (CDCl₃): δ 1.30 (2H, m, CH₂), 1.65 (4H, m, CH₂CH₂), 2.45 (3H, s, CH₃), 2.55 (2H, t, J=7.0 Hz, CH₂CH₂), 4.05 (2H, t, J=7.0 Hz, CH₂CH₂), 7.10–7.40 (7H, m, C₆H₅, tosyl), 7.77 (2H, s, J=7.0 Hz, tosyl).

Step 2

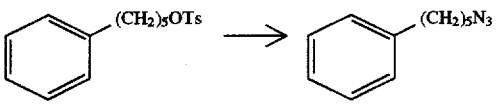

Sodium azide (0.090 g, 1.38 mmol) was added to a solution of the tosylate (0.420 g, 1.32 mmol) in DMF (5.0 mL) and the mixture stirred overnight at room temperature. The mixture was poured into water (25 mL), extracted into Et₂O (2×25 mL) the combined Et₂O extracts dried over MgSO₄, filtered, and the solvent removed in vacuo. This gave the product as a colorless oil (0.229 g, 92%);

IR (film): 3027, 2936, 2859, 2095, and 1495 cm⁻¹; NMR (CDCl₃): δ 1.45 (2H, mM, CH₂), 1.60 (4H, m, CH₂CH), 2.62 (2H, t, J=8.0 Hz, CH₂CH₂), 3.25 (2H, t, J=8.0 Hz, CH₂CH₂), 7.15 (3H, m, Ph), 7.25 (2H, m, Ph).

Step 3

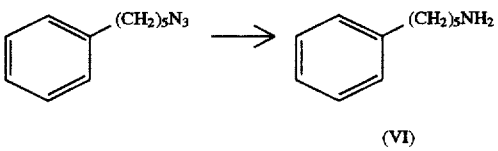

(VI)

A solution of the azide (0.220 g, 1.16 mmol) in 95% EtOAc (70 mL) was hydrogenated overnight at room temperature over Lindlar catalyst (0.110 g) at 30 psi of H₂. The catalyst was filtered and the solvent removed in vacuo to give the crude product as a syrup which was used without purification in Step 4.

Step 4

N,N'-dicyclohexylcarbodiimide (0.073 g, 0.35 mmol) was added to a stirred solution of the acid (II, prepared, Example 4, Step 3) (0.150 g, 0.35 mmol) and 1-hydroxybenzotriazole monohydrate (0.054 g, 0.35 mmol) in EtOAc (7 mL). The mixture was stirred at room temperature for 2 hours and the N,N'-dicyclohexylurea filtered off. The amine (0.057 g, 0.35 mmol) was added and the reaction mixture stirred overnight at room temperature. The solvent was removed in vacuo and the residue purified by chromatography on silica using 40% EtOAc/60% n-hexane as eluant to give the product as a white solid (0.165 g, 83%), mp 85°–90° C.;

IR (film): 3326, 2932, 1687, 1665, 1650, 1497, and 1454 cm$^{-1}$; NMR (CDCl$_3$): δ 1.32, 1.36 (9H, 2s, C(CH$_3$)$_3$), 1.50–1.65 (9H, m, CH$_3$, 3 CH$_2$), 2.59 (2H, t, J=7.0 Hz, CH$_2$CH$_2$Ph), 2.80–3.40 (6H, m, 3CH$_2$), 4.05 (1H, m, CH$_2$CH), 4.80, 4.90 (1H, 2 brs, CHNHCOO), 5.85, 6.20 (1H, 2 brs, CONH), 6.50, 6.65 (1H, 2 brs, CONH), 6.95 (2H, brs, Ph), 7.10–7.40 (13H, m, Phs); Analysis calculated for C$_{35}$H$_{45}$N$_3$O$_4$.

EXAMPLE 7

DL-Phenylalaninamide, N-[(1,1-dimethylethoxy) carbonyl]-L-phenylalanyl-N-cyclopentyl-α-methyl-

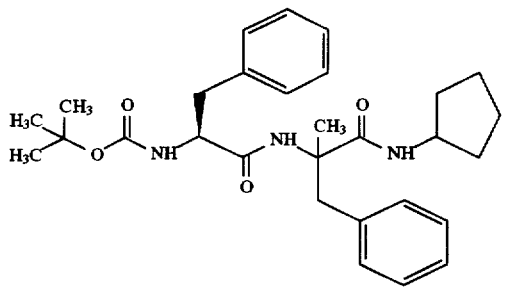

Step 4

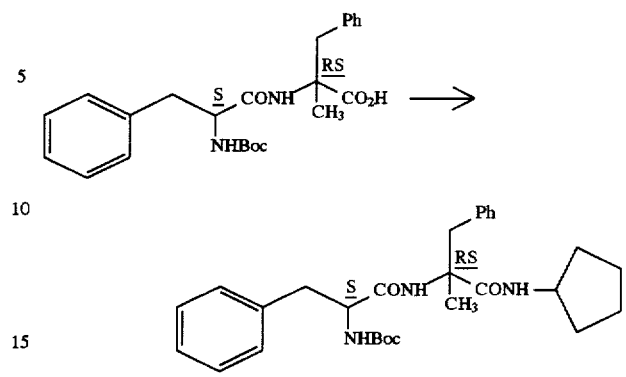

N,N'-dicyclohexylcarbodiimide (0.107 g, 0.52 mmol) was added to a stirred solution of the acid (II, prepared, Example 4, Step 3) (0.200 g, 0.47 mmol) and 1-hydroxybenzotriazole monohydrate (0.086 g, 0.56 mmol) in EtOAc (20 mL). The mixture was stirred at room temperature for 2 hours and the N,N'-dicyclohexylurea filtered off. Cyclopentylamine (0.060 g, 0.71 mmol) in EtOAc (2 mL) was added dropwise over 2 minutes and the mixture stirred at room temperature for 72 hours. The solution was washed with 5% citric acid solution (2×25 mL), saturated NaHCO$_3$ (2×25 mL), 5% citric acid (25 mL), and once with brine (25 mL). The EtOAc solution was dried over MgSO$_4$, filtered, and the solvent removed in vacuo. The residue was purified by chromatography on silica using 67% n-hexane/33% EtOAc as eluant giving the product as a white solid (0.208 g, 90%), mp 148°–155° C.;

IR (film): 3329, 2935, 1691, and 1644 cm$^{-1}$; NMR (CDCl$_3$): δ 1.33, 1.37 (9H, 2s, NHCOOC(CH$_3$)$_3$), 1.46, 1.57 (3H, 2s, CH$_3$), 1.50–1.70 (6H, m, cyclopentyl), 1.88–1.99 (2H, m, cyclopentyl), 2.79–3.47 (4H, m, 2CH$_2$Ph), 4.03–4.20 (2H, m, 2CH$_2$CHN), 4.81–4.86 (1H, m, N HCOOC(CH$_3$)$_3$), 6.01, 6.32 (1H, 2 bs, CONH), 6.44, 6.58 (1H, 2 bs, CONH), 6.95–7.02 (2H, m, Ph), 7.16–7.36 (8H, m, Ph); Analysis calculated for C$_{29}$H$_{39}$N$_3$O$_4$·0.25H$_2$O: C, 69.92; H, 7.99; N, 8.44. Found: C, 69.98; H, 8.09; N, 8.56.

EXAMPLE 8

DL-Phenylalaninamide, N-[(1,1-dimethylethoxy) carbonyl]-L-phenylalanyl-N-(8-methoxyoctyl)-α-methyl-

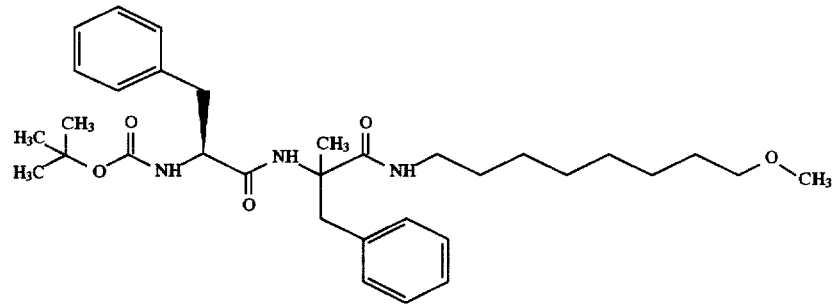

Step 1

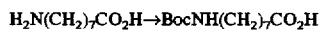

BocNH(CH$_2$)$_7$CO$_2$H

Di-tert-butyl dicarbonate (1.7 g, 7.85 mmol) in dioxan (7 mL) was added dropwise over 5 minutes to a stirred solution of 8-aminocaprylic acid (1 g, 6.28 mmol) in 1N NaOH (7 mL) and dioxan (7 mL) containing $Na_2CO_3$ (0.83 g, 7.85 mmol). The resulting mixture was stirred overnight at room temperature. The mixture was diluted with water (25 mL) and the dioxan was removed in vacuo. The solution was extracted once with ether (25 mL) and the pH of the aqueous solution was then adjusted to four with 5% citric acid. The product was then extracted into ether (3×50 mL). The combined ether extracts were dried over $MgSO_4$, filtered, and the solvent was removed in vacuo to give a white solid, 1.61 g (99% yield), mp 56° C.;

IR (film): 3366, 2974, 2939, 2857, 2689, 1698, and 1524 $cm^{-1}$; NMR ($CDCl_3$): δ 1.28–1.33 (7H, m, $3CH_2$, $CHH$), 1.45 (10H, s, $CHH$, $C(CH_3)_3$), 1.58–1.65 (2H, m, $CH_2$), 2.34 (2H, t, J=7.4 Hz, $CH_2COOH$), 3.05–3.15 (2H, m, C $H_2NHCOO$), 4.60 (0.5H, b, 0.5 $NHCOO$), 5.80 (0.5H, b, $0.5NHCOO$); Analysis calculated for $C_{13}H_{25}NO_4$: C, 60.21; H, 9.72; N, 5.40. Found: C, 60.19; H, 9.59; N, 5.32.

Step 2

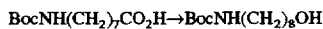

BocNH(CH$_2$)$_7$CO$_2$H→BocNH(CH$_2$)$_8$OH

BocNH(CH$_2$)$_8$OH

Ethyl chloroformate (0.72 mL, 7.5 mmol) in anhydrous THF (22 mL) was added dropwise over 20 minutes to a stirred solution of $BocNH(CH_2)_7CO_2H$ (1.74 g, 6.71 mmol) and N-methyl morpholine (0.84 mL, 7.5 mmol) in anhydrous THF (50 mL cooled in an ice bath). After 1 hour, the N-methyl morpholine salt was filtered off and 2.0M $LiBH_4$ (10.3 mL, 20.6 mmol) was added dropwise over 10 minutes. The resulting mixture was stirred with a slow rewarming to room temperature for 3 hours. The solvent was removed in vacuo and the mixture was redissolved in EtOAc. This was then washed with water and brine. The organic phase was dried over $MgSO_4$ and the solvent removed in vacuo to give a white solid 0.158 g (62% yield), mp 54.5°–55.3° C.;

IR (film): 3367, 2931, 2854, 1687, 1524, and 1171 $cm^{-1}$; NMR ($CDCl_3$): δ 1.31–1.63 (2H, m, $BocCH_3×3$, $6×CH_2OH$), 3.09 (1H, m, $CH_2NCOO$), 3.63 (1H, t, J=6.6 Hz, $CH_2$, OH), 4.51 (1H, s, urethane).

Step 3

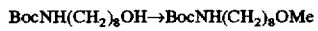

BocNH(CH$_2$)$_8$OH→BocNH(CH$_2$)$_8$OMe

BocNH(CH$_2$)$_8$OMe

To a vigorously stirred mixture of $BocNH(CH_2)_8OH$ (392 mg, 1.6 mmol) and fluoroboric acid (210 μL, 1.6 mmol) in DCM (8 mL), the TMS $CHN_2$ (800 μL, 1.6 mmol) was added dropwise at 0° C. The solution was stirred at 0° C. and three further additions of TMS $CHN_2$ (400 μL, 0.8 mmol and 200 μL×2, 0.4 mmol) were added at 15-minute intervals. The mixture was stirred for a further 4 hours after which starting material was still visible by t.l.c. but no further evolution of the reaction was however apparent.

The reaction was diluted with water and extracted with DCM (×3). The combined extracts were washed with water (×3), then dried over $MgSO_4$, and solvent removed in vacuo. The product was purified by flash chromatography 1% to 5% MeOH/DCM, 212 mg (54% yield);

NMR ($CDCl_3$): δ 1.25–1.58 (21H, m, $BocCH_3×3$, $CH_2×6$), 3.04–3.18 (2H, m, $CH_2N$), 3.30–3.39 (5H, m, $CH_2$ OC $H_3$), 4.52 (1H, brs, urethane NH).

Step 4

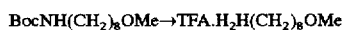

BocNH(CH$_2$)$_8$OMe→TFA.H$_2$H(CH$_2$)$_8$OMe

TFA.H$_2$N(CH$_2$)$_8$OMe $BocNH(CH_2)_8OMe$ (212 mg, 0.86 mmol) was dissolved in TFA (1 mL) and DCM (1 mL) and the solution was stirred at room temperature for 1 hour. The solvent was removed in vacuo, washing with DCM×3, removing in vacuo to give 299 mg containing 1.6 equivalent of TFA;

NMR ($CDCl_3$): δ 1.31 (8H, s, $CH_2×4$), 1.57–1.75 (4H, m, $CH_2×2$), 2.98–3.15 (2H, m, $CH_2NH$), 3.37 (3H, 2×s, OMe), 3.44 (2H, t, $CH_2OMe$), 7.46 (2H, s, amine salt), 10.4 (2H, s, acid).

Step 5

Boc$S$PheR$S$αMePheOH→Boc$S$PheR$S$αMePheNH(CH$_2$)$_8$OMe

BocSPheRSαMePheNH(CH$_2$)$_8$OMe

BocSPheRSαMePheOH (II, prepared, Example 4, Step 3) (200 mg, 0.5 mmol) and HBTU (190 mg, 0.5 mmol) were dissolved in DMF (3 mL) and DIPEA (99 μL, 0.57 mmol) was added. The solution was stirred at room temperature for 10 minutes. The TFA.H$_2$N(CH$_2$)$_8$OMe (164 mg, 0.48 mmoL) and the remaining DIPEA (199 μL, 1.1 mmol) was then added and the solution was stirred for a further 17 hours at room temperature. The solvent was removed in vacuo and the residue was redissolved in EtOAc. The organic was washed with dilute HCl, $NaHCO_3$, water, and then dried over $MgSO_4$, the solvent was removed in vacuo, and the residue was purified by flash chromatography 1% MeOH/ DCM to give a white solid 101 mg (36% yield), mp 76°–81° C.;

IR (film): 3312, 2977, 2931, 2857, 1686, 1649, and 1528 $cm^{-1}$; MS FAB: $MH^+$ 568; NMR ($CDCl_3$): δ 1.28–1.60 (24H, m, $BocCH_3×3$, $αCH_3$, $CH_2×6$), 3.32–3.38 (11H, m, $βCH_2×2$, $OCH_3$, $CH_2OCH_3$, $CONHCH_2$), 3.94–4.12 (1H, m, αCH), 4.82–4.91 (1H, m, urethane NH), 5.86, 6.18 (1H, 2×s, amide NH), 6.49, 6.65 (1H, 2×s, amide NH), 6.94–6.98 (2H, m, aromatics), 7.21–7.26 (8H, m, aromatics); HPLC: 40–100% B over 20 minutes, A=$H_2O$, B=$CH_3CN$, 0.1% TFA, R$_f$=18.11 minutes, >95% purity; Analysis calculated for $C_{33}H_{49}N_3O_5$·0.25$H_2O$: C, 69.26; H, 8.72; N, 7.34. Found: C, 69.27; H, 8.81; N, 7.31.

EXAMPLE 9

DL-Phenylalaninamide, N-[(1,1-dimethylethoxy) carbonyl]-L-phenylalanyl-N-(7-carboxyheptyl)-α-methyl-

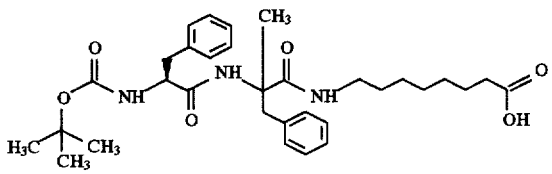

Step 1

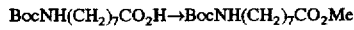

BocNH(CH$_2$)$_7$CO$_2$H→BocNH(CH$_2$)$_7$CO$_2$Me

BocNH(CH$_2$)$_7$CO$_2$Me $BocNH(CH_2)_7CO_2H$ (prepared, Example 8, Step 1) (300 mg, 1.2 mmol) was dissolved in methanol (5 mL) and DCC (239 mg, 1.2 mmol) was then added. The solution was stirred at room temperature overnight. The DCU was removed by filtration and the solvent was removed in vacuo. The residue was then taken up in EtoAc and washed with dilute HCl (200 mL×3), water (200 mL×3), and then dried over MgSO₄, filtered, and the solvent was removed in vacuo to yield an oil, 0.259 g (79% yield);

IR (film): 3368, 2932, 2858, 1739, 1715, and 1520 cm⁻¹; NMR (CDCl₃): δ 1.31 (6H, s, CH₃×3), 1.44 (11H, s, BocCH₃×3, CH₂), 1.43 (2H, br t, CH₂), 2.30 (2H, t, J=7.5 Hz, C$\underline{H}$₂CO₂R), 3.09 (2H, m, C$\underline{H}$₂NCO), 3.67 (3H, s, OCH₃), 4.57 (1H, br s, NH).

Step 2

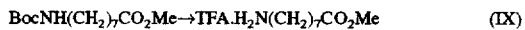

TFA.H₂N(CH₂)₇CO₂Me

BocNH(CH₂)₇CO₂Me (200 mg, 0.73 mmol) was dissolved in TFA (2 mL) and DCM (2 mL) and the mixture was stirred at room temperature for 1 hour. The solvent was then removed in vacuo and the residue was dried to give an oil, 192 mg (91% yield);

IR (film): 3436, 2939, and 1682 cm⁻¹; NMR (CDCl₃): δ 1.32 (6H, br s, CH₂×3), 1.60 (4H, m, CH₂×2), 2.30 (2H, t, J=7.4 Hz, C$\underline{H}$₂CO₂CH₃), 2.93 (2H, br, C$\underline{H}$₂NHCO), 3.66 (3H, s, OC$\underline{H}$₃), 5.38 (1H, br s, NH).

Step 3

BocSPheRSαMePheNH (CH₂)₇CO₂Me

BocSPheRSαMePheOH (II, prepared, Example 4, Step 3) (200 mg, 0.5 mmol) was dissolved in DCM (3 mL) and HBTU (190 mg, 0.5 mmol) and DIPEA (87.6 μL, 0.5 mmol) were added. The solution was stirred for 10 minutes at room temperature. TFA.H₂N(CH₂)₇CO₂Me (80 mg, 0.5 mmol) and the remaining DIPEA (175.4 μL, 1.0 mmol) were added and the solution was stirred overnight at room temperature. The solvent was removed in vacuo and the residue was redissolved in EtoAc. The organic phase was washed with 10% NaHCO₃, dilute HCl, water, and dried over MgSO₄. The solvent was removed in vacuo and the residue was purified by reverse phase chromatography 80% MeOH/H₂O to give a white solid, 211 mg (73% yield), mp 120°–123° C.;

IR (film): 3339, 3030, 2933, 2857, 1738, 1690, 1651, and 1524 cm⁻¹; MS (CI): 583 (MH⁺), 582, (M⁺), 482, 174, and 134); NMR (CDCl₃): δ 1.11–1.62 (22H, m, BocCH₃×3, αCH₃, CH₂×5), 2.29 (2H, t, J=7.5 Hz, C$\underline{H}$₂CO₂Me), 2.78–3.44 (6H, m, βCH₂×2, C$\underline{H}$₂NCO), 3.65 (3H, s, OCH₃), 4.01–4.13 (1H, m, αCH), 5.00, 5.12 (1H, 2×br d, urethane NH), 5.99, 6.35 (1H, 2×s, amide NH), 6.71, 6.81 (1H, 2×br s, amide NH), 6.96 (2H, m, aromatics), 7.17–7.36 (8H, m, aromatics); HPLC: 40–100% B over 20 minutes, A=H₂O, 0.1% TFA, B=CH₃CN, 0.1 TFA; R$_t$=17.27 minutes, 97% purity. Analysis calculated for C₃₃H₄₇N₃O₆.0.3H₂O: C, 67.50; H, 8.17; N, 7.16. Found: C, 67.53; H, 8.25; N, 7.21.

Step 4

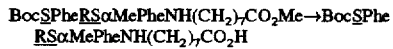

BocSPheRSαMePheNH(CH₂)₇CO₂H

BocSPheRSαMePheNH(CH₂)₇CO₂Me (91 mg, 0.16 mmol) was dissolved in dioxan (1 mL) and LiOH (320 μL, 0.32 mmol) was added. The reaction was stirred at room temperature for 3.5 hours. The solvent was removed in vacuo and the residue was dissolved in water. The aqueous was washed once with ether and the pH was adjusted to three with dilute HCl. The product was then extracted into ether and the organic layer was dried over MgSO₄, filtered, and the solvent was removed in vacuo to give a white solid 79 mg (87% yield), mp 52°–53.5° C.;

IR (film): 3326, 2932, 2858, 1709, 1651, and 1520 cm⁻¹; NMR (CDCl₃): δ 1.25–1.58 (22H, m, CH₃×3, αCH₃, CH₂×5), 2.34 (2H, t, J=7.3 Hz, C$\underline{H}$₂NHCO), 2.89–3.38 (6H, m, βCH₂×2, C$\underline{H}$₂CO₂H), 4.00–4.19 (1H, m, αCH), 4.92–5.10 (1H, 2×br d, urethane NH), 5.92, 6.22 (1H, 2×s, amide NH), 6.55, 6.68 (1H, 2×br s, amide NH), 6.96 (2H, m, aromatics), 7.19–7.33 (8H, m, aromatics); MS (CI): 569 MH⁺, 568 (M⁺), 468, 160, and 134; HPLC: 40–100% B over 20 minutes, A=H₂O, 0.1% TFA, B=CH₃CN, 0.1% TFA; R$_t$=13.7 minutes, 95% purity; Analysis calculated for C₃₂H₄₅N₃O₆.0.6H₂O: C, 66.44; H, 7.94; N, 7.26. Found: C, 66.37; H, 8.05; N, 7.19.

EXAMPLE 10

DL-Phenylalaninamide, N-[(1,1-dimethylethoxy)carbonyl]-L-phenylalanyl-N-[2-(acetylamino)ethyl]-α-methyl-

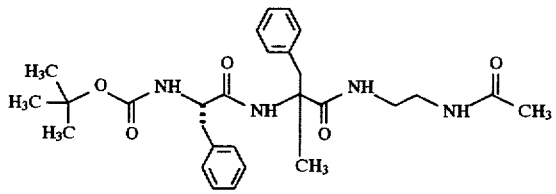

BocSPheRαMePheOH (II, prepared Example 4, Step 3) (0.20 g, 0.5 mmol), HBTU (0.19 g, 0.5 mmol) and DIPEA (88 μL, 0.5 mmol) were dissolved in DMF (5 mL) and the solution was stirred for 10 minutes. The N-acetylethylenediamine (0.62 g, 0.6 mmol) and the remaining DIPEA (88 μL, 0.5 mmol) were added and the solution was stirred overnight. The solution was concentrated in vacuo and the residue was redissolved in EtOAc (50 mL). The solution was washed sequentially with dilute HCl (3×50 mL), saturated NaHCO₃ (3×50 mL), water (3×50 mL), and brine (2×50 mL). The organic phase was dried over MgSO₄, filtered, and concentrated in vacuo. The residue was purified by medium pressure silica chromatography, eluting with 1% MeOH in DCM to give 240 mg (96% yield) as a white foam, mp 72°–74° C.;

IR (film): 3307, 2979, 1685, 1654, and 1533 cm⁻¹; MS (CI): 511 (MH⁺); [α]$_D^{24}$=−24.9° (C=0.5 MeOH); NMR (CDCl₃): δ 1.32, 1.36 (9H, 2×s, BocCH₃), 1.47, 1.54 (3H, 2×s, αCH₃), 1.96, 1.99 (3H, 2×s, NCOC$\underline{H}$₃), 2.13–3.38 (8H, m, βCH₂×2, CH₂×2), 4.00 (1H, m, αCH), 4.93, 5.04 (1H, 2×br d, urethane NH), 6.06, 6.20 (1H, 2×s, amide NH), 6.50 (1H, 2×br s, amide NH), 6.95 (3H, m, 2×aromatics, amide NH), 7.16–7.34 (8H, m, aromatics); Analysis calculated for C₂₈H₃₈N₄O₅.0.5H₂O: C, 64.72; H, 7.56; N, 10.78. Found: C, 64.75; H, 7.44; N, 10.73.

EXAMPLE 11

DL-Phenylalaninamide, N-[(1,1-dimethylethoxy)carbonyl]-L-phenylalanyl-N-(2-cyclopentylethyl)-α-methyl-

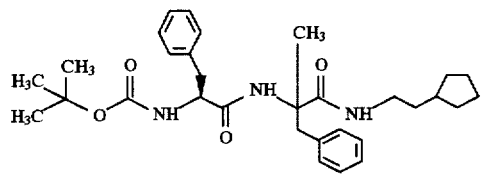

Step 1

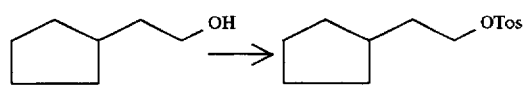

2-Cyclopentyl ethanol (1.0 g, 8.76 mmol) was dissolved in pyridine (10 mL) and tosyl chloride (1.90 g, 10 mmol) was added. The reaction was stirred at room temperature overnight. The reaction mixture was diluted with EtOAc and washed with dilute HCl, NaHCO₃, and H₂O. The organic phase was dried over MgSO₄ and the solvent was removed in vacuo to give an oil. The product was purified by medium pressure chromatography 0–100% EtoAc/Hexane to give an oil, 1.02 g (43% yield);

IR (film): 2950, 1599, 1335, and 1179 cm$^{-1}$; MS (CI): 269 (MH$^+$) and 537 (M$^{2+}$); NMR (CDCl₃): δ 0.96–1.07 (2H, m, CH₂), 1.45–1.83 (9H, m, CH₂×4, CH), 2.45 (3H, s, CH₃), 4.04 (2H, t, J=6.6 Hz, C$\underline{H}$₂Otos), 7.34 (2H, d, J=8.3 Hz, aromatics, H$_{3,5}$), 7.79 (2H, d, J=8.3 Hz, aromatics, H$_{2,6}$); HPLC: 40–100% B over 30 minutes; A=H₂O, 0.1% TFA; B=CH₃CN, 0.1% TFA; R$_t$=18.91 minutes >98% purity; Analysis calculated for C₁₄H₂₀O₃S: C, 62.66; H, 7.51. Found: C, 62.52; H, 7.56.

Step 2

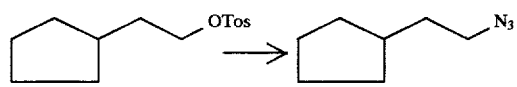

The tosylate (Step 1) (0.803 g, 3 mmol) was dissolved in DMF (10 mL) and sodium azide (0.251 g, 3.3 mmol) was added. The solution was stirred at room temperature overnight and then poured onto ice. The ice was then extracted with EtOAc and the combined extracts washed with brine. The solvent was then removed in vacuo to give a clear oil, 0.255 g (61% yield);

IR (film): 2950, 2869, and 2096 cm$^{-1}$; NMR (CDCl₃): δ 1.08–1.14 (2H, m, CH₂), 1.52–1.86 (9H, m, CH₂×4, CH), 3.27 (2H, t, J=7.2 Hz, C$\underline{H}$₂N₃).

Step 3

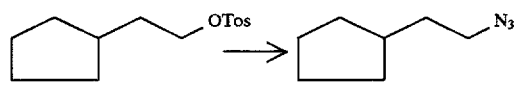

The azide (Step 2) (0.255 g, 1.8 mmol) was dissolved in ethanol (20 mL) and Lindlar catalyst (50 mg) was added. The solution was hydrogenated at 40 psi, 30° C. for 2.5 hours The catalyst was removed by filtration through celite and the solvent was removed in vacuo to give a residue (44 mg). The residue was used without purification.

Step 4

BocSPheRSαMePheOH ⟶

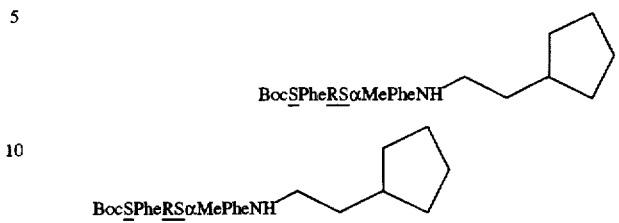

BocSPheRSαMePheOH (II, prepared, Example 4, Step 3) (166 mg, 0.39 mmol) and HBTU (148 mg, 0.39 mmol) were dissolved in DMF (3 mL). DIPEA (68 μL; 0.39 mmol) was added and the solution was stirred for 10 minutes. The amine (Step 3) (44 mg, 0.39 mmol) and the remaining DIPEA (69 μL, 0.39 mmol) were added and the reaction was stirred over the weekend. The solvent was removed in vacuo and the residue was redissolved in EtoAc. The organic phase was then washed with dilute HCl, 10% NaHCO₃, water, and then dried over MgSO₄. The solvent was then removed in vacuo to give a brown oil which was purified by medium pressure chromatography 20% MeOH/DCM to give a white solid 85 mg (42% yield), mp 119°–123° C.;

IR (film): 3887, 3826, 3344, 2949, 1672, 1688, 1640, and 1523 cm$^{-1}$; [α]$_D^{21.0}$=−20.4° (C=0.265 in MeOH); MS (CI): 522 (M$^+$), 422, and 134; HPLC: 40–100% B over 20 minutes, A=H₂O 0.1% TFA, B=CH₃CN, 0.1% TFA, R$_t$=19.0 minutes >95% purity; NMR (CDCl₃): δ 1.07 (2H, m, CH₂), 1.33, 1.37 (9H, 2×s, BocCH₃×3), 0.92–1.74 (12H, m, αCH₃, CH₂×4, CH), 2.75–3.43 (6H, m, βCH₂×2, C$\underline{H}$₂NCO), 4.00–4.11 (1H, m, αCH), 4.82–4.90 (1H, 2×br d, urethane NH), 5.87, 6.20 (1H, 2×s, amide NH), 6.47, 6.60 (1H, 2×s, amide NH), 6.95 (2H, m, aromatics), 7.16–7.36 (8H, m, aromatics); Analysis calculated for C₃₁H₄₃N₃O₄: C, 71.37; H, 8.31; N, 8.05. Found: C, 71.40; H, 8.29; N, 8.01.

EXAMPLE 12

DL-Phenylalaninamide, N-[(1,1-dimethylethoxy)carbonyl]-L-phenylalanyl-N-[2-(4-chlorophenyl)ethyl]-α-methyl-

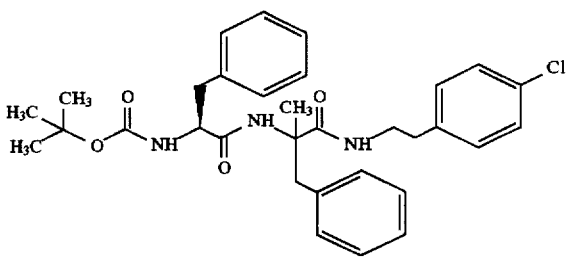

To a stirred solution of Boc(L)Phe(DL)αMePhe (II, prepared, Example 4, Step 3) (0.20 g, 0.47 mmol) in dimethylformamide (5 mL) was added HBTU (0.18 g, 0.47 mmol), diisopropylamine (0.12 g, 0.94 mmol) and 2-(4-chlorophenyl)ethylamine (0.073 g, 0.47 mmol). The reaction was stirred at room temperature for 20 hours. The dimethylformamide was removed in vacuo and the residue taken up in ethyl acetate. The organic layer was washed with 0.1N hydrochloric acid, dried over magnesium sulphate, and the solvent removed in vacuo. Purification by column chromatography gave the product, 0.175 g (66%), mp 161°–164° C.;

IR (film): 3325 (NH), 2979 (CH), 1684 (C=O urethane), 1653 (amide I), and 1494 (amide II); NMR (CDCl$_3$): 1.33, 1.36 (9H, 2×s, (C$\underline{H}_3$)$_3$C), 1.45, 1.53 (3H, 2×s, αCH$_3$), 2.73–3.44 (8H, m, CH$_2$×4), 3.90–4.15 (1H, m, αCH), 4.75–4.90 (1H, m, urethane NH), 5.81, 6.10 (1H, 2×s, amide NH), 6.60–6.70, 6.70–6.80 (1H, 2×m, amide NH), 6.90–6.98 (2H, m, aromatics), 7.06–7.33 (12H, m, aromatics); Analysis calculated for C$_{32}$H$_{38}$ClN$_3$O$_4$: C, 68.13; H, 6.79; N, 7.45. Found: C, 67.85; H, 6.80; N, 7.38.

EXAMPLE 13

DL-Phenylalaninamide, N-[(1,1-dimethylethoxy) carbonyl]-L-phenylalanyl-N-[(4-carboxycyclohexyl) methyl]-α-methyl-, trans-

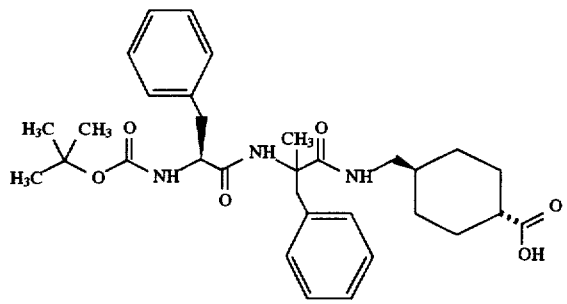

Boc(L)Phe(DL)αMePheOH (II, prepared, Example 4, Step 3) (0.200 g; 0.47 mmol), HBTU (0.178 g, 0.47 mmol) and diisopropylethylamine (0.388 mL, 1.41 mmol) were stirred together in DMF (5 mL) at room temperature for 20 minutes. Trans-4-(aminomethyl)cyclohexane carboxylic acid was then added and the resulting suspension was stirred for 18 hours. On removal of DMF, the residue was partitioned between water and ethyl acetate. The organic layer was washed with 2M HCl and further purified by reverse phase column chromatography using 50% to 90% MeOH/ H$_2$O to give a white solid (0.080 g, 30%), mp 100°–116° C.;

IR (film): 3335, 1705, 1670, and 1644 cm$^{-1}$; MS: (CI) 134 (100%), 566 (M+1); NMR (DMSO-d$_6$): δ 0.75–2.10 (21H, m, Boc, αCH$_3$, cyclohexyl), 2.65–3.35 (6H, m, 2×β-CH$_2$—, —CONHCH$_2$—), 4.00–4.15 (1H, m, αH) 6.90–7.85 (13H, m, Ar, —OCCNH—, 2×—CONH—); Analysis calculated for C$_{32}$H$_{43}$N$_3$O$_6$: C, 67.94; H, 7.66; N, 7.43. Found: C, 67.66; H, 7.60; N, 7.23.

EXAMPLE 14

DL-Phenylalaninamide, N-[(1,1-dimethylethoxy) carbonyl]-L-phenylalanyl-α-methyl-

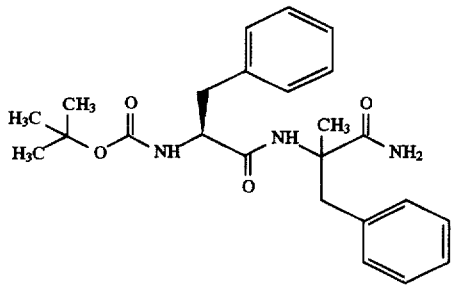

Step 1

αMePheOH ⟶ BocαMePheOH
RS         RS

The acid (1.0 g, 5.58 mmol) was stirred and dissolved in 1,4-dioxan (10 mL). To this was added H$_2$O (10 mL) followed by Na$_2$CO$_3$ (1.18 g, 11.16 mmol) and di-tert-butyldicarbonate (1.46 g, 6.70 mmol) in 1,4-dioxan (3 mL). The mixture was stirred vigorously at room temperature overnight and then the 1,4-dioxan removed in vacuo. The residue was diluted with water (50 mL) and extracted with Et$_2$O (2×25 mL). The aqueous solution was made pH 3 with citric acid solution and extracted with EtOAc (3×25 mL). The combined EtOAc extracts were washed with water (3×25 mL), dried over MgSO$_4$, filtered, and the solvent removed in vacuo giving the product as a white solid (1.06 g, 68%);

IR (film): 2982, 1713, 1498, 1453, and 1369 cm$^{-1}$; NMR (DMSO-d$_6$): δ 1.19 (3H, s, CH$_3$), 1.41 (9H, s, C(C$\underline{H}_3$)$_3$), 2.93 (1H, d, J=13.3 Hz, PhC$\underline{H}$H), 3.30 (1H, d, obscured by H$_2$O, PhC$\underline{H}$H), 6.66 (1H, bs, OCON$\underline{H}$), 7.10 (2H, d, J=7.2 Hz, Ph), 7.18–7.29 (3H, m, Ph), 12.5 (1H, bs, COO$\underline{H}$).

Step 2

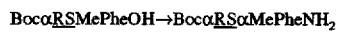
BocαRSMePheOH→BocαRSαMePheNH$_2$

Et$_3$N (0.598 g, 5.9 mmol) was added to a stirred solution of the acid (1.50 g, 5.37 mmol) in EtOAc (25 mL) and the mixture cooled to −10° C. Isobutylchloroformate (0.807 g, 5.91 mmol) in EtOAc (5.0 mL) was added dropwise over 5 minutes and the mixture stirred at room temperature for 30 minutes. The mixture was filtered and ammonia gas bubbled through the stirred solution for 35 minutes. The solid precipitate was filtered off giving the product as a white solid (0.794 g, 53%);

NMR (DMSO-d$_6$): δ 1.33 (3H, s, CH$_3$), 1.41 (9H, s, (C$\underline{H}_3$)$_3$C), 3.18 (2H, s, CH$_2$), 6.25 (1H, bs, CON$\underline{H}$N), 7.07–7.26 (6H, m, C$_6$H$_5$,

OCN$\underline{H}$), 7.42 (1H, bs, CON$\underline{H}$H).

Step 3

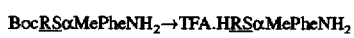
BocRSαMePheNH$_2$→TFA.H$\underline{R}$SαMePheNH$_2$    (X)

The amide (0.60 g, 2.16 mmol) was stirred and suspended in anhydrous CH$_2$Cl$_2$ (4 mL) and trifluoroacetic acid (5 mL) added. The mixture was stirred for 50 minutes and then the solvent removed in vacuo. The residue was triturated with Et$_2$O, filtered, and the solid dried under vacuum to give the product as a white powder (0.601 g, 95%);

IR (film): 3401, 3313, 1659, and 1525 cm$^{-1}$; NMR (DMSO-d$_6$): δ 1.48 (3H, s, CH$_3$), 3.02 (1H, d, J=14.0 Hz, PhC$\underline{H}$H), 3.16 (1H, d, J=14.0 Hz, PhC$\underline{H}$H), 7.21–7.34 (5H, m, C$_6$H$_5$), 7.70 (1H, s, CON$\underline{H}$H), 7.89 (1H, s, CON$\underline{H}$H), 8.00 (3H, bs, N$^+$H$_3$).

TFA.RαMePheNH$_2$ (XI) was prepared by an analogous procedure;

NMR (DMSO-d$_6$): δ 1.48 (3H, s, αCH$_3$), 3.02 (1H, d, J=14.0 Hz, βCH), 3.16 (1H, d, J=14.0 Hz, βCH), 7.20–7.35 (5H, m, aromatics), 7.69, 7.89 (1H, 2×s, CONH$_2$), 8.02 (3H, bs, NH$_3$$^+$).

Step 4

BocSPheOH+TFA.HRSαMePheNH₂→BocSPheRSαMePheNH₂ 

Diisopropylethylamine (0.362 g, 2.80 mmol) in DMF (1 mL) was added to a stirred solution of the acid (0.248 g, 0.93 mmol) and HBTU (0.354 g, 0.94 mmol) in DMF (5 mL) and the mixture stirred for 15 minutes at room temperature. The TFA salt (0.30 g, 1.03 mmol) in DMF (5 mL) was then added dropwise over 5 minutes and the reaction stirred at room temperature for 30 minutes. The solvent was removed in vacuo and the residue purified by chromatography on silica using EtOAc as eluant. This gave the product as a white amorphous solid (0.188 g, 47%), mp 141°–143° C.;

IR (film): 3300, 2981, 1666, and 1497 cm⁻¹; NMR (DMSO-d₆): δ 1.30 (9H, s, C(CH₃)₃), 1.42 (3H, s, CH₃), 2.72–2.80 (1H, m, PhCHH), 2.96–3.07 (1H, m, PhCHH), 3.15–3.40 (2H, m, PhCH₂), 4.04–4.20 (1H, m, CH₂CH), 6.80–7.27 (3H, m, 2C₆H₅, CONH₂, OCONH), 7.57 (1H, s, CONH); Analysis calculated for C₂₄H₃₁N₃O₄.0.1H₂O.

EXAMPLE 15

DL-Phenylalaninamide, N-[(4-hydroxyphenyl)acetyl]-L-phenylalanyl-α-methyl-

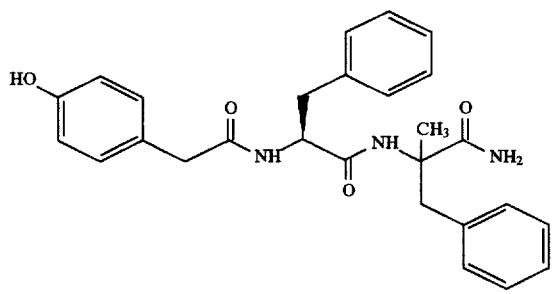

Step 1

BocSPheRSαMePheNH₂→TFA.SPheRSαMePheNH₂ 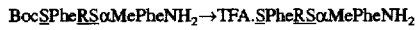

TFA.(L)Phe(D,L)αMePheNH₂

Boc(L)Phe(D,L)αMePheNH₂ (Example 14, Step 4) (8.90 g, 0.032 mol) was stirred in cold trifluoroacetic acid for 10 minutes. The solution was evaporated down to an oil and then triturated with diethyl ether to give a white solid (9.26 g, 99%), mp 272°–276° C.;

υmax (film)/cm⁻¹: 3223br (NH), 3032 (NH of +NH₃), 2926 (Ali-H), 1679 (CO amide), 1670 (CO amide), and 1530 (CO amide); δ_H(DMSO): 1.28, 1.36 (3H, 2s, CH₂CCH₃), 3.0 (2H, m, PhCH₂CH), 3.20 (2H, m, PhCH₂C), 4.13 (1H, m, PhCH₂CH), 7.2 (13H, m, H_arom, NH, NH₂), 8.14 (3H, d, J=13 Hz, +NH₃).

Step 2

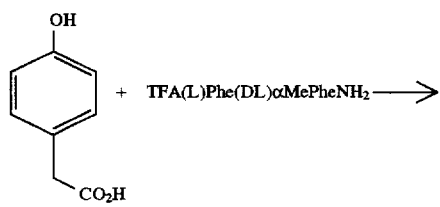

+ TFA(L)Phe(DL)αMePheNH₂ ⟶

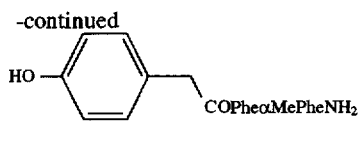

L    DL

4-Hydroxyphenylacetic acid (69 mg, 0.45 mmol) and HBTU (172 mg, 0.45 mmol) were stirred together in DMF (5 mL) for 20 minutes. TFA.(L)Phe(DL)αMePheNH₂ (200 mg, 0.45 mmol) and diisopropylethylamine (0.257 mL, 1.48 mmol) in DMF (5 mL) were added and the solution was stirred for 18 hours at room temperature. On removal of the DMF, the residue was dissolved in ethyl acetate and washed with 10% citric acid solution, 10% Na₂CO₃ solution, and water. Purification by prepared HPLC using 20% to 80% CH₃CN/H₂O+0.1% TFA, gave a white solid (50 mg, 24%), 30:70 mixture of diastereoisomers by HPLC (95% pure);

IR (film): 3261, 1680, and 1645 cm⁻¹; NMR (DMSO-d₆): δ 1.28 (1/2×3H, s) and 1.35 (1/2×3H, s, αCH₃), 2.70–3.45 (6H, m, 4×β-CH₂— and benzyl CH₂), 4.33 (1/2×1H, m) and 4.48 (1/2×1H, m, αH), 6.56–7.29 (16H, m, Ar, —CONH₂), 7.69 (1H, s, —CONH—), 8.26 (1/2×1H, d, J=8.4 Hz) and 8.33 (1/2×1H, d, J=7.4 Hz, —CONH—), 9.13 (1H, s, —OH).

EXAMPLE 16

DL-Phenylalaninamide, N-[(cyclohexylmethoxy)carbonyl]-L-phenylalanyl-α-methyl-

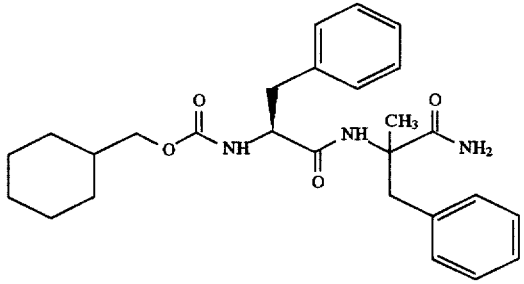

Pyridine (0.069 mL, 0.85 mmol) in DCM (1 mL) was added dropwise to a solution of triphosgene (0.092 g, 0.31 mmol) and cyclohexylmethanol (0.105 mL, 0.85 mmol) in DCM (4 mL) at 0° C. The solution was stirred for 5 minutes. The mixture was evaporated down to a white solid, taken up in ethyl acetate (~10 mL), and filtered. The filtrate was added to a solution of TFA(L)Phe(DL)αMePheNH₂ (0.150 g, 0.34 mmol) and triethylamine (0.094 mL, 0.68 mmol) in DMF (3 mL) and allowed to stir for 18 hours at room temperature. On removal of the solvents, the residue was partitioned between water and ethyl acetate. The organic layer was washed with 10% citric acid solution, 10% Na₂CO₃ solution, and water. Further purification by reverse phase chromatography using 60% to 90% MeOH/H₂O gave a white solid (0.120 g, 76%);

IR (film): 3305 cm⁻¹ and 1665 cm⁻¹; M/e (CI): 466 (M+1) and 134 (100%); NMR (DMSO-d₆): δ 0.83–1.60 (14H, m, cyclohexyl, αCH₃), 2.47–3.37 (4H, m, β-CH₂—'s), 3.67 (2H, m,

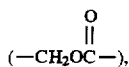

(—CH₂OC—), 4.09 (1/2×1H, m), and 4.19 (1/2×1, m, αH), 7.05-7.73 (14H, m, Ar, —CONH₂, —CONH—, —OCONH—); Analysis calculated for $C_{27}H_{35}N_3O_4$: C, 69.65; H, 7.58; N, 9.03. Found: C, 69.35; H, 7.62; N, 8.84.

EXAMPLE 17

DL-Phenylalaninamide, N-[(2-methylpropoxy)carbonyl]-L-phenylalanyl-α-methyl-

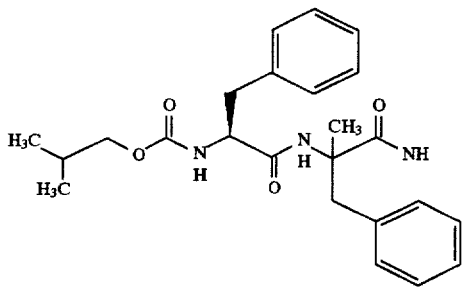

Step 1

TFA.RSαMePheNH₂→FmocSPheRSαMePheNH₂

Fmoc(L)Phe(D,L)αMePheNH₂

Fmoc(L)PheOpfp (8.60 g, 0.0155 mol), TFA.(DL)αMePheNH₂ (X) (4.80 g, 0.0162 mol), and triethylamine (2.27 mL, 0.0162 mol) in N,N-dimethylformamide (200 mL) were stirred together over a weekend. The solvent was evaporated off under pressure and the resulting thick yellow oil diluted in H₂O (250 mL). This was extracted into ethyl acetate and the resulting organic solution washed with H₂O, 10% citric acid, 10% sodium carbonate, brine and H₂O in turn, dried over magnesium sulphate, and evaporated down to a yellow foam. The product was purified by flash chromatography (2% methanol in CH₂Cl₂), followed by washing with petroleum ether to give a pale yellow solid (6.70 g, 79%), mp 83°–85° C.;

υmax (film)/cm⁻¹: 3306 (NH), 3031 (ar-H), 2931 (Ali-H), 1667 (CO amide), 1604 (C=C Ar), and 1533 (CO amide); $δ_H$(DMSO): 1.37, 1.39 (3H, 2s, Ch₂CCH₃), 2.80 (1H, m, 1 of PhCH₂CH), 3.00 (1H, m, 1 of PhCH₂CH), 3.20 (2H, m, PhCH₂C), 4.11 (1H, m, PhCH₂CH), 7.2 (22H, m, $H_{arom}$, N H₂, NH).

Step 2

FmocSPheRSαMePheNH₂→SPheRSαMePheNH₂  (XII)

(L)Phe(DL)αMePheNH₂

Fmoc(L)Phe(DL)αMePheNH₂ (6.70 g, 0.0122 mol) was stirred in 20% piperidine in N,N-dimethylformamide (40 mL) for 20 minutes. The solvent was evaporated off under pressure and the resulting solid washed with 1:1 hexane:diethyl ether and dissolved in 10% citric acid. This was neutralized with 10% sodium carbonate solution and the product extracted into ethyl acetate. The organic solution was washed with brine and H₂O in turn, dried over magnesium sulphate, and evaporated down to a pale yellow foam. This was washed with more 1:1 hexane:diethyl ether, mp 69°–72° C.;

υmax (film)/cm⁻¹: 3308 (NH), 3029 (Ar—H), 2926 (Ali-H), and 1661 (CO amide); $δ_H$(DMSO): 1.45, 1.47 (3H, 2s, Ch₂CCH₃), 2.64 (1H, m, 1 of PhCH₂CH), 2.85 (1H, m, 1 of PhCH₂CH), 3.33 (2H, m, PhCH₂C), 4.42 (1H, m, PhCH₂C H), 7.2 (12H, m, HH$_{arom}$, NH₂), 7.31, 7.41 (1H, 2s, amide NH), 8.16 (2H, s, NH₂CH).

Step 3

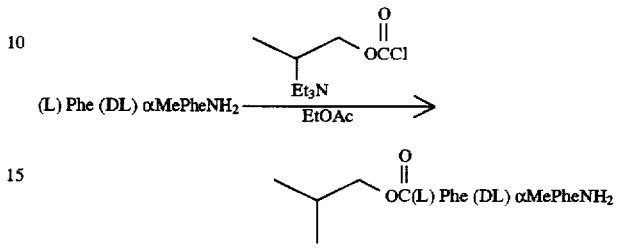

Isobutyl chloroformate (0.066 mL, 0.50 mmol) was added dropwise to a solution of (L)Phe(DL)αMePheNH₂ (150 mg, 0.46 mmol) and triethylamine (0.064 mL, 0.46 mmol) in ethyl acetate (8 mL) at 0° C. The mixture was allowed to warm to room temperature and stirred for 18 hours. The resulting solution was washed with 10% citric acid solution and water. Drying (MgSO₄) and evaporation yielded a yellow oil. Further purification by flash chromatography using 2.5% MeOH/DCM and the reverse phase chromatography using 60% to 90% MeOH/H₂O gave a white solid (90 mg, 46%);

IR (film): 3308, 2960, and 1669 cm⁻¹; M/e (FAB): 448 (M+Na); NMR (DMSO-d₆): δ 0.81 (6H, m, 2×CH₃), 1.37 (1/2×3H, s) and 1.38 (1/2×3H, s, αCH₃), 1.74 (1H, m, Me₂C H—), 2.70–3.36 (4H, m, 4×β H's), 3.63 (2H, m, —CH₂OCO—), 4.13 (1H, m, αH), 7.05–7.27 (12H, m, Ar, —CONH₂), 7.42 (1/2×1H, d, J=8.6 Hz), 7.54 (1/2×1H, d, J=7.9 Hz, —CONH—), 7.75 (1H, d, J=4.8 Hz, —OCONH—); Analysis calculated for $C_{24}H_{31}N_3O_4$: C, 67.74; H, 7.34; N, 9.87. Found C, 67.46; H, 7.34; N, 9.81.

EXAMPLE 18

DL-Phenylalaninamide, N-[[(3,4-dichlorophenyl)-methoxy]carbonyl]-L-phenylalanyl-α-methyl-

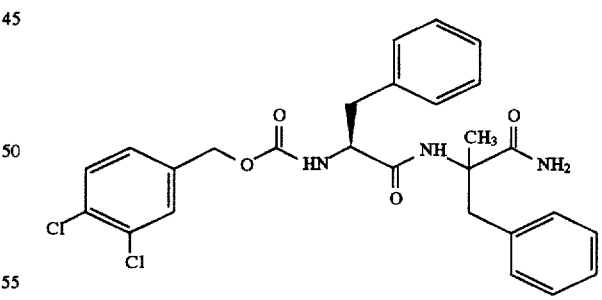

Pyridine (0.097 mL, 1.2 mmol) in DCM (0.5 mL) was added dropwise to a solution of 3,4-dichlorobenzyl alcohol (212 mg, 1.2 mmol) and triphosgene (130 mg, 0.44 mmol) in DCM (2 mL) at 0° C. The mixture was stirred for 10 minutes and evaporated down to a white solid which was taken up in ethyl acetate and filtered. The filtrate was added to a solution of (L)Phe(DL)αMePheNH₂ (XII) (150 mg, 0.46 mmol) and triethylamine (0.064 mL, 0.46 mmol) in ethyl acetate and allowed to stir for 18 hours. The resulting suspension was washed with 10% citric acid solution, 10%

Na₂CO₃, and water. Further purification by flash chromatography using 2% MeOH/DCM and then reverse phase chromatography using 60% to 90% MeOH/H₂O gave a white solid (120 mg, 49%);

IR (film): 3309, 1714, and 1664 cm⁻¹; M/e (FAB): 511 (100%), 528 (M+1), and 532 (M+5); NMR (DMSO-d₆): δ 1.35 (1/2×3H, s) and 1.39 (1/2×3H, s, αCH₃), 2.67–3.38 (4H, m, 4×β H's), 4.10–4.27 (1H, m, αH), 4.95 (2H, m, —C H₂—OCO—), 7.05–7.85 (17H, m, Ar, —CONH₂, —CONH—, —OCONH—); Analysis calculated for C₂₇H₂₇N₃O₄Cl₂: C, 61.37; H, 5.15; N, 7.95. Found: C, 61.37; H, 5.12; N, 7.91.

EXAMPLE 19

DL-Phenylalaninamide, N-[[(octahydro-2-naphthalenyl)-oxy]carbonyl]-L-phenylalanyl-α-methyl-

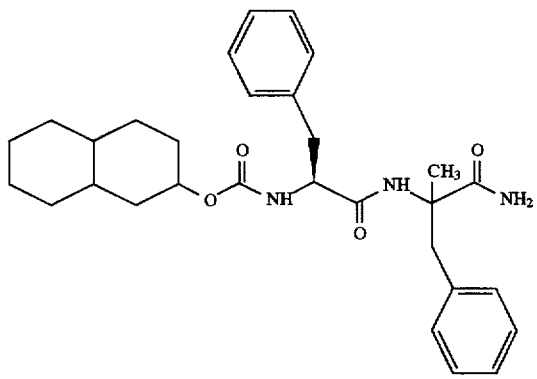

Step 1

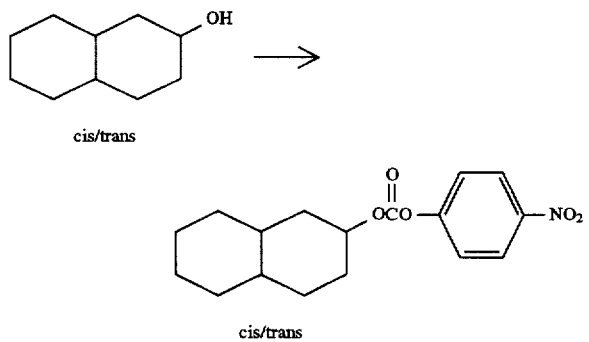

To a stirred solution of Cis/trans decahydro-2-naphthol (1.54 g, 10 mmol) and 4-nitrophenylchloroformate (2.01 g, 10 mmol) in dichloromethane (50 mL) cooled to 0° C. was added dropwise a solution of pyridine (0.79 g, 10 mmol) in dichloromethane (10 mL). The reaction was stirred overnight at room temperature. The solvent was removed in vacuo and the residue was taken up in ethyl acetate (100 mL) and 10% aqueous citric acid (10 mL). The ethyl acetate was washed with 10% citric acid, saturated aqueous sodium bicarbonate, water, and brine, dried over magnesium sulphate, and the solvent removed in vacuo. Purification by flash chromatography gave a white solid, 2.28 g (71%), mp 48°–52° C.;

IR (film): 2925, 1762, 1525, and 1346 cm⁻¹; NMR (CDCl₃): 0.90–2.20 (16H, m, aliphatics), 4.71, 4.93 (1H, 2×m CHO (cis and trans)), 7.38 (2H, d, J=9.1 Hz aromatics adjacent to

O
‖
OC), 8.27 (2H, d, J=9.1 Hz, aromatics adjacent to NO₂). Analysis calculated for C₁₇H₂₁NO₅: C, 63.94; H, 6.63; N, 4.39. Found: C, 64.01; H, 6.65; N, 4.39.

Step 2

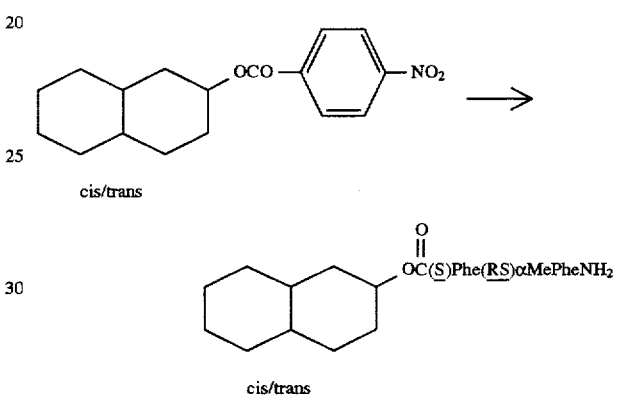

To a stirred solution of TFA.(L)Phe(DL)αMePheNH₂ (0.2 g, 0.45 mol) and decahydronaphthyl-p-nitrophenyl carbonate (prepared, Example 15, Step 1) (0.16 g, 0.5 mmol) in dimethylformamide (10 mL) was added dropwise triethylamine (0.101 g, 10 mmol) in dimethylformamide (5 mL). The reaction was stirred for 8 days. The dimethylformamide was removed in vacuo and the residue taken up in ethyl acetate. The ethyl acetate was washed with 2N hydrochloric acid, saturated aqueous sodium bicarbonate, water and brine, and dried over magnesium sulphate. The solvent was removed in vacuo. Purification by flash chromatography in 10% ethyl acetate/hexane increase to 100% ethyl acetate gave a white foam, 0.155 g (67%), mp 88°–92° C.;

IR (film): 3307 (NH), 2924 (CH), 1690 (shoulder, urethane C=0), 1668 (amide I), and 1512 (amide II); [α]_D²⁵= –21.1° (C=0.53 in MeOH); NMR (CDCl₃): 1.18–1.90 (19H, m, αCH₃ and decahydronaphthyl×16), 2.88–3.42 (4H, m, 2×CH₂), 4.05–4.20 (1H, m, αCH), 4.45–4.55 and 4.65–4.80 (1H, 2×m, CHO), 4.96, 5.04 (1H, 2×broad s, urethane), 5.29, 6.45 (2H, 2×broad s, NH₂), 5.95, 6.21 (1H, 2×s amide NH), 7.01 (2H, m, aromatics), 7.16–7.33 (8H, m, aromatics); Analysis calculated for C₃₀H₃₉N₃O₄: C, 71.26; H, 7.77; N, 8.31. Found: C, 71.16; H, 7.78; N, 8.23.

EXAMPLE 20

DL-Phenylalaninamide, N-[(1,1-dimethylethoxy)carbonyl]-L-phenylalanyl-3-chloro-α-methyl-

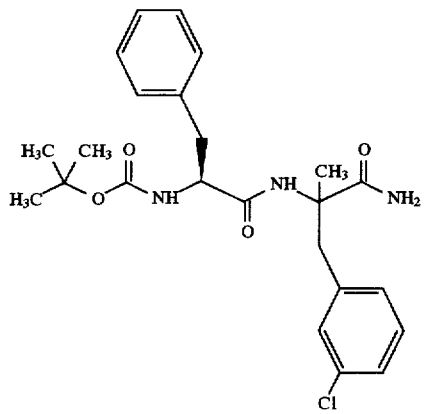

Step 1

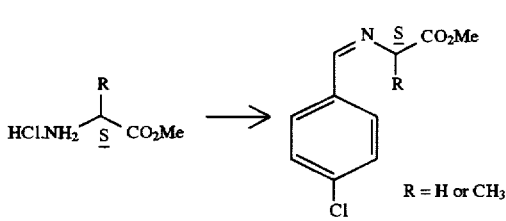

R = H or CH₃

R=Me

To a suspension of S-alanine methyl ester hydrochloride (5 g, 35.8 mmol), magnesium sulphate (0.75 g) and 4-chlorobenzaldehyde (5.035 g, 35.8 mmol) in dichloromethane (50 mL) was added triethylamine (3.64 g, 36.0 mmol). The reaction mixture was stirred overnight, filtered, and concentrated under reduced pressure. The residue was taken up in diethyl ether and the suspension filtered. The filtrate was concentrated under reduced pressure to yield the desired product (8.0 g, 99%) as a colorless oil;

NMR 1.52 (3H, d, J=6.8 Hz >CH—C$\underline{H}_3$), 3.75 (3H, s, OC$\underline{H}_3$), 4.16 (1H, q, J=6.8 Hz >C$\underline{H}$—CH₃), 7.38 (2H, d, J=8.5 Hz, aromatics), 7.71 (2H, d, J=8.5 Hz, aromatics), 8.26 (1H, s, Ar—C$\underline{H}$=N).

R=H

The R=H analog was prepared by the same method. NMR: 3.78 (3H, s, OCH₃), 4.41 (2H, s, NC$\underline{H}_2$CO), 7.40 (2H, d, J=8.4 Hz, aromatics), 7.72 (2H, d, J=8.4 Hz, aromatics), 8.26 (1H, s, Ar C$\underline{H}$=N).

Step 2

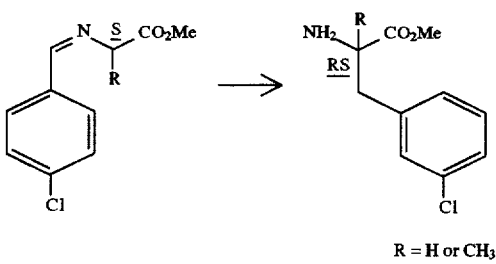

R = H or CH₃

To a solution of the Schiff base (prepared, Example 20, Step 1) (0.5 g, 2.2 mmol) in tetrahydrofuran (10 mL) at −78° C. was added LHMDS (2.43 mL of 1M, 2.4 mmol). The mixture was stirred at −78° C. for 0.5 hour and the 3-chlorobenzyl bromide (0.455 g, 2.2 mmol) added. The reaction was allowed to slowly warm to room temperature over 4 hours. 1M HCl solution (10 mL) was added and the reaction stirred at room temperature for 20 hours. The reaction mixture was partitioned between ethyl acetate and water. The aqueous layer was made basic with sodium bicarbonate and extracted with ethyl acetate. The organic extracts were dried over magnesium sulphate and evaporated to yield the product, 0.24 g (48%) as a yellow oil.

IR (film): 2951 (CH) and 1735 (ester C=O); NMR (CDCl₃): 1.37 (3H, s, αCH₃), 2.76, 3.07 (2H, 2×d, J=14 Hz, CH₂), 3.74 (3H, s, OCH₃), 6.98–7.08 (1H, m, aromatics), 7.15–7.25 (3H, m, aromatics).

The analog in which R=H was prepared by the same procedure, 368 mg, 41% yield;

IR (film): 2951 and 1737 cm⁻¹; M/e (CI): 214 (M+1) and 154 (100%); NMR DMSO-d₆: δ 1.87 (2H, bs, —NH₂), 2.75 (1/2×2H, 1/2×ABX, J=13.4 Hz, 7.7 Hz) and 2.88 (1/2×2H, 1/2×ABX, J=13.4 Hz, 5.9 Hz, benzyl CH₂—), 3.58 (4H, m, —CO₂CH₃, αH), 7.13–7.33 (4H, m, Ar).

Step 3

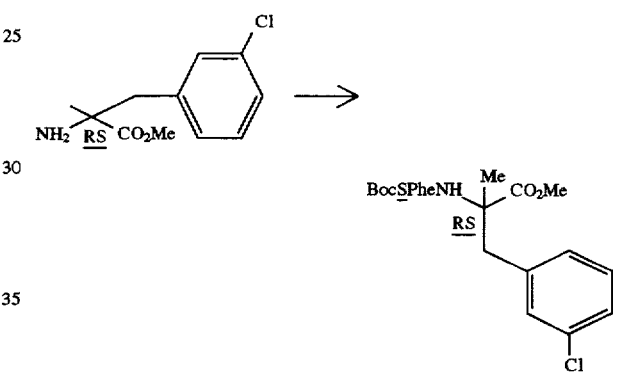

To a stirred solution of Boc-S-phenylalanine (0.29 g, 1.1 mmol) in dimethylformamide (5 mL) was added HBTU (0.42 g, 1.1 mmol), diisopropylamine (0.28 g, 2.2 mmol) and

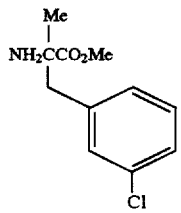

(0.25 g, 1.1 mmol).

The reaction was stirred at room temperature for 20 hours. The dimethylformamide was removed in vacuo and the residue taken up in ethyl acetate, washed with 0.1 hydrochloric acid, dried over magnesium sulphate and the solvent removed in vacuo. Purification by column chromatography gave a white amorphous solid, 0.34 g (65%), mp 38°–42° C.;

IR (film): 3308 (NH), 2980 (CH), 1738 (C=O, ester), 1661 (amide I, overlapping urethane, C=O), and 1519 (amide II); NMR (CDCl₃): 1.36, 1.39 (9H, 2×s, (CH₃)₃C), 1.54, 1.57 (3H, 2×s, αCH₃), 2.90–3.52 (4H, m, 2×βCH₂), 3.73, 3.74 (3H, 2×s, OC$\underline{H}_3$), 4.20–4.32 (1H, m, αCH), 4.85–4.95 (1H, m, urethane NH), 6.41, 6.50 (1H, 2×s, amide NH), 6.75–6.85 (1H, m, aromatic), 6.96–6.99 (1H, m, aromatic) 7.08–7.30 (7H, m, aromatics); Analysis calculated for $C_{25}H_{31}ClN_2O_5$: C, 63.22; H, 6.58; N, 5.90. Found: C, 63.05; H, 6.53; N, 5.84.

Step 4

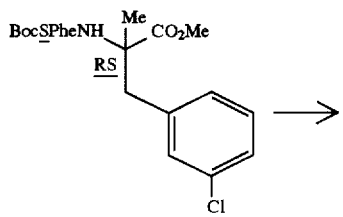

To a stirred solution of the ester (0.30 g, 0.63 mmol) in tetrahydrofuran (8 mL)/water (2 mL) was added lithium hydroxide (0.02 g, 0.83 mmol). The reaction mixture was stirred at room temperature overnight and concentrated under reduced pressure. The residue was partitioned between ethyl acetate and 0.1M hydrochloric acid. The organic layer was dried over magnesium sulphate and evaporated to yield the desired acid as a crude sample (0.14 g, 48%);

IR (film): 3340 (NH), 2980 (CH), 1713 (C=O acid), 1662 (amide I), and 1514 (amide II); NMR (CDCl$_3$): 1.32, 1.39 (9H, 2×s, (C$\underline{H}_3$)$_3$C), 1.53 (3H, s, αCH$_3$), 2.85–3.55 (4H, m, 2×βCH$_2$), 4.60–4.75 (1H, m, αCH), 5.15–5.45 (1H, m, urethane NH), 6.80–7.29 (10H, m, 9×aromatics, amide NH).

Step 5

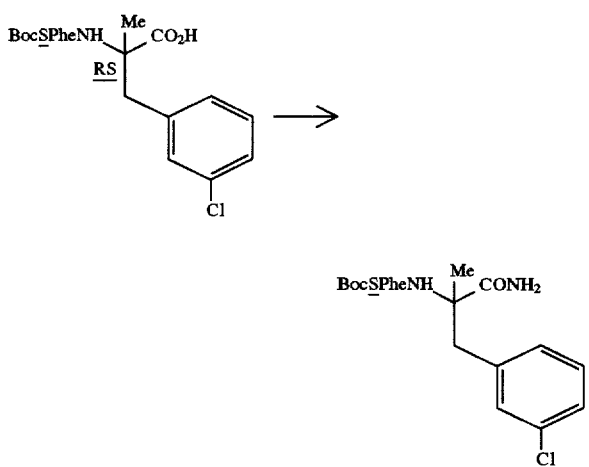

To a stirred solution of the acid (0.221 g, 0.48 mmol) in ethyl acetate (10 mL) was added HOBt (0.078 g, 0.48 mmol) and DCC (0.099 g, 0.48 mmol). The reaction mixture was filtered after 3 hours and aqueous ammonia (0.205 g) added to the filtrate. After stirring for 3 days, the reaction mixture was concentrated under reduced pressure. The crude residue was purified by column chromatography to yield the product, 0.16 g (73%) as a white crystalline solid, mp 142°–148° C.;

IR (film): 3308 (NH), 2980 (CH), 1667 (amide I), and 1498 (amide II); NMR (CDCl$_3$): 1.34, 1.36 (9H, 2×s, (C$\underline{H}_3$)$_3$C), 1.54, 1.61 (3H, 2×s, αCH$_3$), 2.79–3.52 (4H, m, βCH$_2$×2), 4.04–4.15 (1H, m, αH), 4.89–4.94 (1H, m, urethane NH), 5.18–5.32 (1H, m, NH$_2$), 6.01, 6.17 (1H, 2×s, NH), 6.55–6.80 (1H, m, NH$_2$), 6.89–7.34 (9H, m, aromatics); Analysis calculated for $C_{24}H_{30}ClN_3O_4$: C, 62.67; H, 6.60; N, 9.14. Found: C, 62.81; H, 6.57; N, 9.11.

EXAMPLE 21

D-Phenylalaninamide, 3-chloro-N-[(1,1-dimethylethoxy)-carbonyl]-DL-phenylalanyl-α-methyl-

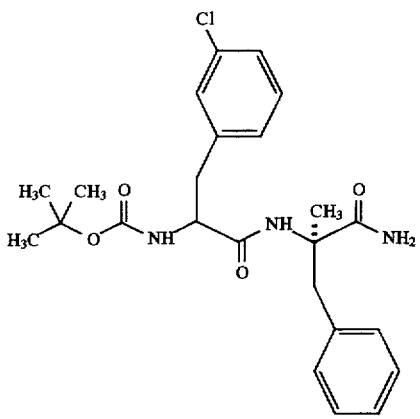

Step 1

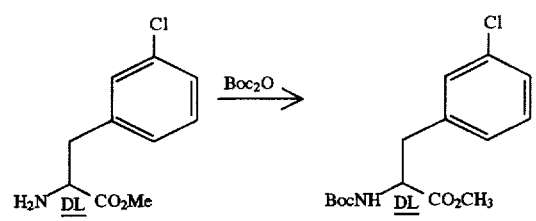

3-Chlorophenylalanine (0.350 g, 1.64 mmol), di-tert-butyl dicarbonate (0.395 g, 1.80 mmol), 10% Na$_2$CO$_3$ (aqueous) solution (5 mL), and dioxan (15 mL) were stirred together at room temperature for 6.5 hours. The mixture was then evaporated to dryness and the residue was partitioned between ethyl acetate and water. The organic phase was washed with 10% citric acid solution and water. Drying (MgSO$_4$) and evaporation gave a yellow oil (0.390 g, 76%);

IR (film): 3362, 2978, 1744, and 1716 cm$^{-1}$; M/e (CI): 314 (M+1) and 214 (100%); NMR (DMSO-d$_6$): δ 1.31 (9H, s, Boc), 2.78–3.08 (2H, m, benzyl-CH$_2$—), 3.62 (3H, s, —CO$_2$CH$_3$), 4.19 (1H, m, αH), 7.18–7.38 (5H, m, Ar, —OCONH—).

Step 2

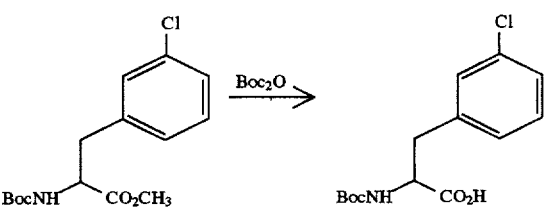

Boc-3-chlorophenylalaninemethyl ester (379 mg, 1.2 mmol) was dissolved in dioxan (10 mL). 1M LiOH (aqueous) (2.4 mL, 2.4 mmol) was added dropwise and the mixture was stirred at room temperature for 2 days. On evaporation of the solvents, the residue was partitioned between water and ethyl acetate. The aqueous layer was acidified to ~pH 4 with citric acid and extracted with ethyl acetate. Drying (MgSO₄) and evaporation gave a yellow oil (294 mg, 82%);

NMR (DMSO-d₆): δ 1.31 (9H, s, Boc), 2.75–3.10 (2H, m, benzyl-CH₂—), 4.10 (1H, m, αH), 7.10–7.38 (5H, m, Ar, —OCONH—), 12.60 (1H, bs, —CO₂H).

Step 3

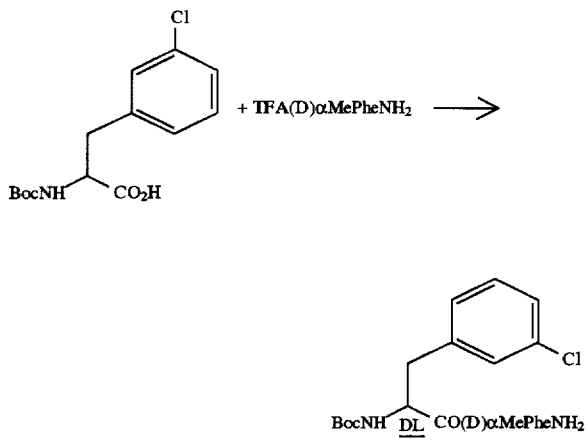

Boc(DL)-3-chlorophenylalanine (0.180 g, 0.6 mmol), HBTU (0.227 g, 0.6 mmol), and diisopropylethylamine (0.311 mL, 0.6 mmol) were stirred in DMF (5 mL) for 20 minutes. TFA.(D)αMePheNH₂ (0.175 g, 0.6 mmol) in DMF (3 mL) was added and the resulting solution was stirred for 15 hours at room temperature. On removal of the DMF, the residue was partitioned between water and ethyl acetate. The organic phase was washed with 10% citric acid solution, 10% Na₂CO₃ solution, and water. Drying (MgSO₄) gave a white solid which was further purified by reverse phase column chromatography using 60% to 90% MeOH/H₂O over 40 minutes, yielding a white solid (0.145 g, 52%);

IR (film): 3306 and 1667 cm⁻¹; MS (CI): 460 (M+1) and 134 (100%); NMR (DMSO-d₆): δ 1.28 (1/2×9H, s) and δ 1.29 (1/2×9H, s, Boc), 1.35 (1/2×3H, s) and 1.38 (1/2×3H, s, αCH₃), 2.65–3.37 (4H, m, β-CH₂—'s), 4.04 (1/2×1H, m) and 4.13 (1/2×1H, m, αH), 7.05–7.37 (12H, m, Ar, —CONH₂, —OCONH—), 7.78 (1/2×1H, s) and 7.80 (1/2× 1H, s, —CONH—); Analysis calculated for C₂₄H₃₀N₃O₄Cl: C, 62.67; H, 6.57; N, 9.14. Found: C, 62.50; H, 6.61; N, 8.96.

EXAMPLE 22

Carbamic acid, [2-[[2-amino-2-oxo-1-(phenylmethyl)-ethyl]amino]-1-(phenylmethyl)ethyl]-, 1,1-dimethylethyl ester

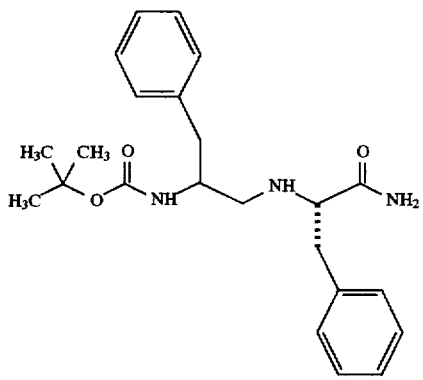

Step 1

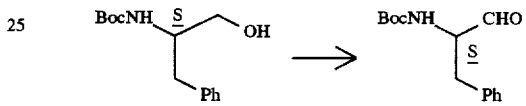

DMSO (0.340 g, 4.35 mmol) in CH₂Cl₂ (3 mL) was added to a solution of oxalyl chloride (0.275 g, 2.17 mmol) in CH₂Cl₂ (10 mL) cooled to –60° C. The cold mixture was stirred for 20 minutes and then the alcohol (0.500 g, 2.00 mmol) in CH₂Cl₂ (3 mL) was added. The reaction was again stirred at –60° C. for 20 minutes followed by addition of Et₃N (0.611 g, 6.04 mmol) in CH₂CL₂ (3 mL). The reaction was allowed to warm to room temperature overnight and then the solvent removed in vacuo. The residue was dissolved in EtOAc and washed with 0.5M HCl, the EtOAc layer dried over MgSO₄, filtered, and the solvent removed in vacuo. The residual product was purified by chromatography on silica using 25% EtOAc/75% n-hexane as eluant to give the aldehyde as a white solid (0.158 g, 32%);

IR (film): 3365, 2969, 1732, 1688, and 1520 cm⁻¹; NMR (CDCl₃): δ 1.40 (9H, s, C(CH₃)₃), 3.11 (2H, d, J=6.0 Hz, PhCH₂), 4.41 (1H, m, CH₂CHCHO), 5.02 (1H, brs,

NHCO), 7.16 (2H, d, J=7.0 Hz, Ph), 7.25 (3H, m, Ph), 9.65 (1H, s, CHO).

Step 2

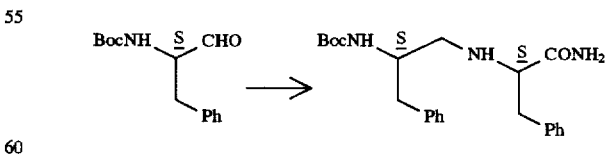

Sodium cyanoborohydride (0.6 mL of 1M solution in THF, 0.60 mmol) was added to a solution of the aldehyde (0.150 g, 0.60 mmol) and S-phenylalaninamide (0.098 g, 0.60 mmol) in MeOH/AcOH (5 mL, 99:1 mixture). The reaction mixture was stirred at room temperature for 6 hours and then saturated NaHCO$_3$ solution added and the mixture extracted into EtOAc. The EtOAc solution was dried over MGSO$_4$, filtered, and the solvent removed in vacuo. The crude product was purified by chromatography on silica using 75% EtOAc/25% n-hexane as eluant giving the aminomethylene compound as an off-white solid (0.075 g, 31%), mp 97°–100° C.;

IR (film): 3358, 2980, 1683, 1660, 1604, 1525, and 1170 cm$^{-1}$; NMR (CDCl$_3$): δ 1.39 (9H, s, C(CH$_3$)$_3$), 2.40–2.80 (6H, m, PhCH$_2$, CH$_2$NH, CH$_2$NHCH$_2$, CH$_2$CHNHCOO), 3.20 (2H, m, PhCH$_2$CHCONH$_2$), 3.80 (1H, m, HNCHCONH$_2$), 4.55 (1H, m, NHCOO), 6.25 (1H, bs, CONHH), 6.90–7.30 (11H, m, CONHH, 2C$_6$H$_5$); Analysis calculated for C$_{23}$H$_{31}$N$_3$O$_3$0.20CHCl$_3$.

EXAMPLE 23

D-Phenylalaninamide, N-[(1,1-dimethylethoxy) carbonyl]-L-phenylalanyl-N-[7-[(aminocarbonyl) amino]heptyl]-α-methyl- Step 1

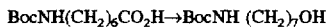

BocNH(CH$_2$)$_6$CO$_2$H (0.45 g, 1.8 mmol) and N-methylmorpholine (0.22 mL, 2 mmol) were dissolved in THF (10 mL). The solution was cooled to 0° C. and ethylchloroformate (0.19 mL, 2 mmol) in THF (10 mL) was added dropwise over 10 minutes. The solution was stirred for 1 hour, and the precipitate was removed by filtration. The filtrate was cooled on an ice bath and LiBH$_4$ (3 mL, 2M in THF, 6 mmol) was added dropwise over 5 minutes. The mixture was stirred with slow warming to room temperature over 3 hours. The solvent was removed in vacuo, and the residue was redissolved in EtOAc (50 mL). The organic was washed with water (3×50 mL), brine (50 mL), and then dried over MgSO$_4$. Removal of the solvent in vacuo gave a clear oil 0.402 g, 90%.

IR (film): 3344, 2931, 2858, 1689, and 1531 cm$^{-1}$. NMR (CDCl$_3$): 1.28–1.60 (19H, m, BocCH$_3$×3, CH$_2$×5), 3.10 (2H, m, CONHCH$_2$), 3.64 (2H, m, CH$_2$OH), 4.50 (1H, br s, urethane NH).

Step 2

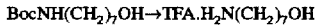

BocNH(CH$_2$)$_7$OH (0.40 g, 1.7 mmol) was dissolved in a 50:50 TFA/DCM solution (20 mL). The reaction mixture was stirred for 1 hour after which the solvent was removed in vacuo. The residue was azeotroped with toluene (5×10 mL), and the resulting oil was used without purification.

Step 3

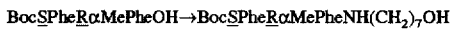

BocSPheRαMePheOH (0.64 g, 1.5 mmol), DCC (0.31 g, 1.5 mmol), and HOBt (0.20 g, 1.5 mmol) were dissolved in DMF (3 mL). The solution was stirred for 5 minutes after which TFA.H$_2$N(CH$_2$)$_7$OH (0.66 g, 1.7 mmol) and DIPEA (0.7 mL, 4 mmol) were added. The solution was stirred for 15 hours, and the precipitate then removed by filtration. The solvent was removed in vacuo and the residue was dissolved in EtOAc (100 mL). The organic was washed with 1M HCl (3×50 mL), saturated NaHCO$_3$ (3×50 mL), water (3×50 mL), and brine (50 mL). The organic was dried over MgSO$_4$ and the solvent was concentrated in vacuo. The residue was purified by reverse phase chromatography 0% to 100% MeOH/H$_2$O over 30 minutes. Removal of the solvent gave a white foam 0.54 g, 67%, mp 46°–49° C.

IR (film): 3324, 3029, 2929, 1661, and 1516 cm$^{-1}$. NMR (CDCl$_3$): δ 1.29–1.58 (22H, m, BocCH$_3$×3, αCH$_3$, CH$_2$×5), 2.75–3.45 (6H, m, βCH$_2$×2, CONHCH$_2$), 3.63 (2H, t, J=6.8 Hz, CH$_2$OH), 4.00 (1H, m, αCH), 4.96 (1H, br d, urethane NH), 5.85 (1H, br s, amide NH), 6.65 (1H, br s, amide NH), 6.96–6.98 (2H, m, aromatics), 7.19–7.35 (8H, m, aromatics). MS (CI): 540 (m$^+$), 440, 134. Analysis calculated for C$_{31}$H$_{45}$N$_3$O$_5$.1/4H$_2$O: C, 68.42; H, 8.43; N, 7.72 Found: C, 68.46; H, 8.32; N, 7.69.

Item 4

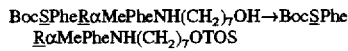

BocSPheRαMePheNH(CH$_2$)$_7$OH (267 mg, 0.5 mmol) was dissolved in DCM (3 ml). Tosyl chloride (105 mg, 0.55 mmol), triethylamine (84 μL, 0.6 mmol), and DMAP (catalytic) were added and the reaction mixture was stirred overnight. The solution was diluted with DCM (50 mL) and washed with 1M HC (3×20 mL), saturated NaHCO$_3$ (3×20 mL), H$_2$O (3×20 mL), and brine (20 mL). The organic was dried over MgSO$_4$ and the solvent was removed in vacuo. A white foam (359 mg) was obtained and was used without purification.

IR (film): 3351, 2978, 2935, 1687, 1657, 1521, 1598, 1366, and 1175 cm$^{-1}$. NMR (CDCl$_3$): δ 1.21–1.66 (22H, m, CH$_3$×3), αCH$_3$, CH$_2$×5), 2.45 (3H, s, CH$_3$), 2.75–3.45 (6H, m, βCH$_2$×2, CONHCH$_2$), 4.01 (3H, m, αCH, CH$_2$OTOS), 4.90 (1H, br d, urethane NH), 5.85 (1H, br s, amide NH), 6.70 (1H, br s, amide NH), 6.96–6.98 (2H, m, aromatics), 7.12–7.35 (10H, m, aromatics), 7.79 (2H, d, J=8.4 Hz, aromatics).

Step 5

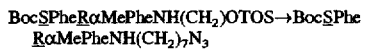

BocSPheRαMePheNH(CH$_2$)$_7$OTOS (317 mg, 0.46 mmol) was dissolved in DMF (5 mL) and NaN$_3$ (33 mg, 0.51 mmol) was added. The reaction mixture was heated to 60° C. for 3 hours, then allowed to cool to room temperature and stirred overnight. The solution was poured onto ice and the aqueous was extracted with DCM (3×100 mL). The combined extracts were washed with water (3×100 mL), brine (100 mL), and dried over MgSO$_4$. The solvent was removed in vacuo and the resulting residue was purified by column chromatography, 50% to 70% ether in hexane. A white foam was obtained 179 mg, 69%.

IR (film): 3322, 2932, 2095, 1683, 1651, and 1517 cm$^{-1}$. NMR (CDCl$_3$): δ 1.30–1.60 (22H, m, BocCH$_3$ X3, αCH$_3$, CH$_2$×5), 2.75–3.45 (8H, m, βCH$_2$×2, CONHCH$_2$, CH$_2$N$_3$) 4.00 (1H, m, αCH), 4.90 (1H, br s, urethane NH), 5.85 (1H, br s, amide NH), 6.70 (1H, br s, amide NH), 6.97–6.99 (2H, m, aromatics), 7.10–7.36 (8H, m, aromatics).

Step 6

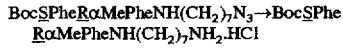

BocSPheRαMePheNH(CH$_2$)$_7$N$_3$ (275 mg, 0.49 mmol), was dissolved in ethanol (20 mL) and Lindlar catalyst (60 mg) was added. The solution was hydrogenated at 40 psi, 30° C. for 6 hours, after which the catalysts was removed by filtration through Kieselguhr. The solvent was removed in vacuo to give a white foam 266 mg. The product was dissolved in MeOH/1M HCl and purified on a reverse phase column, 50% to 100% MeOH/H$_2$O. Removal of the solvent gave a white solid 215 mg, 76%, mp 94°–102° C.

IR (film): 3322, 2933, 1689, 1652, and 1520 cm$^{-1}$. NMR (CDCl$_3$): δ 1.20–1.50 (20H, m, BocCH$_3$×3, αCH$_3$, CH$_2$×4), 2.84 (2H, br t, C<u>H</u>$_2$CH$_2$NH$_2$), 2.75–3.33 (8H, m, βCH$_2$×2, CONHC<u>H</u>$_2$, C<u>H</u>$_2$NH$_2$), 4.08 (1H, m, αCH), 5.20 (1H, br s, urethane NH), 6.24 (1H, br s, amide NH), 6.79 (1H, brt, amide NH), 7.00 (2H, m, aromatics), 7.18–7.33 (8H, m, aromatics), 8.34 (3H, br s, NH$_3^+$Cl$^-$). Analysis calculated for C$_{31}$H$_{46}$N$_4$O$_4$·1.3 HCl: C, 63.53; H, 8.13; N, 9.56. Found: C, 63.43; H, 8.10; N, 9.51.

Step 7

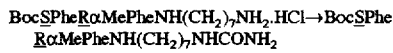

BocSPheRαMePheNH(CH$_2$)$_7$NH$_2$·HCl (130 mg, 0.24 mmol) and triethylamine (33 μL, 0.24 mmol) were dissolved in THF (3 mL). Trimethylsilylisocyanate (67 μL, 0.5 mmol) was added and the reaction mixture was stirred overnight. The solvent was removed in vacuo and the residue was redissolved in EtOAc (100 mL). The solution was washed with 1M HCl (3×50 mL), saturated NaHCO$_3$ (3×50 mL), and water (3×50 mL). The organic was dried over MgSO$_4$ and the solvent was removed in vacuo. The residue was purified by column chromatography, 5% MeOH/DCM to give a white foam 66 mg, 47%, mp 65°–72° C.

IR (film): 3344, 2931, 1693, 1651, and 1539 cm$^{-1}$. NMR (CDCl$_3$): δ 1.21–1.52 (22H, m, BocCH$_3$×3, αCH$_3$, CH$_2$×5), 2.75–3.22 (8H, m, βCH$_2$×2, CONHC<u>H</u>$_2$, C<u>H</u>$_2$NHCONH$_2$), 4.02 (1H, m, αCH), 4.55 (2H, br s, NHCON<u>H</u>$_2$), 5.05, 5.15 (2H, 2×br s, urethane NH, CH$_2$NHCON<u>H</u>$_2$), 5.95 (1H, br s, amide NH), 6.80 (1H, br s, amide NH), 6.97–6.99 (2H, m, aromatics), 7.18–7.34 (8H, m, aromatics). MS (FAB): 605 (M$^+$Na), 582 (M$^+$H), 482, 335. Analysis calculated for C$_{31}$H$_{47}$N$_5$O$_5$·0.4 H$_2$O: C, 65.26; H, 8.04; N, 11.89. Found: C, 65.32; H, 8.07; N, 11.79.

EXAMPLE 24

D-Phenylalaninamide, N-[(1,1-dimethylethoxy)carbonyl]-L-phenylalanyl-α-methyl-N-8-(methylsulfonyl)octyl]

Step 1

BocSPheRαMePheNH(CH$_2$)$_8$OH (Example 1) (0.200 g, 0.36 mmol) and triethylamine (60 μL, 0.43 mmol) were dissolved in DCM (2 mL). Tosyl chloride (0.076 g, 0.4 mmol) and DMAP (catalytic) were then added and the solution was stirred for 15 hours. The reaction mixture was diluted with CDM (50 mL), then washed with 2M HCl (3×30 mL), saturated NaHCO$_3$ (3×50 mL), and water (3×30 mL). The organic was dried over MgSO$_4$, filtered, and the solvent was removed in vacuo. The residue was purified by column chromatography, 3% MeOH in DCM to give an oil 0.179 g, 70%.

IR (film): 3353, 2932, 2862, 1690, 1656, and 1521 cm$^{-1}$. NMR (CDCl$_3$): δ 1.65–1.98 (24H, m, BocCH$_3$×3, αCH$_3$, CH$_2$×2), 2.45 (3H, s, TOSC<u>H</u>$_3$), 2.74–3.48 (6H, m, βCH$_2$×2, CONHC<u>H</u>$_2$), 4.01 (3H, m, αCH, C<u>H</u>$_2$OTOS), 4.90 (1H, br d, urethane NH), 5.82 (1H, br s, amide NH), 6.70 (1H, br, amide NH), 6.95–6.98 (2H, m, aromatics), 7.19–7.36 (10H, m, aromatics), 7.78 (2H, d, J=8.4 Hz, aromatics).

Step 2

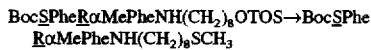

BocSPheRαMePheNH(CH$_2$)$_8$OTOS (0.17 g, 0.24 mmol) and K$_2$CO$_3$ (0.05 g, 0.36 mmol) were dissolved in DMF (3 mL). Methane thiol was bubbled through the solution for 10 minutes and stirring was continued for a further 2.5 hours. The reaction mixture was then diluted with ether (50 mL) and washed with brine (3×30 mL). The organic was dried over MgSO$_4$, filtered, and the solvent was removed in vacuo to give a clear glass 0.113 g, 81%.

IR (film): 3326, 2928, 2855, 1686, 1652, and 1517 cm$^{-1}$. NMR (CDCl$_3$): δ 1.22–1.62 (24H, m, BocC<u>H</u>$_3$×3, αCH$_3$, CH$_2$×6), 2.09 (3H, s, SC<u>H</u>$_3$), 2.48 (2H, t, C<u>H</u>$_2$SCH$_3$), 2.75–3.42 (6H, m, βCH$_2$×2, CONHC<u>H</u>$_2$), 4.00 (1H, m, αCH), 4.90 (1H, br s, urethane NH), 5.85 (1H, br s, amide NH), 6.62 (1H, br s, amide NH), 6.96–6.98 (2H, m, aromatics), 7.19–7.35 (8H, m, aromatics).

Step 3

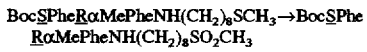

BocSPheRαMePheNH(CH$_2$)$_8$SCH$_3$ (0.113 g, 0.2 mmol), was dissolved in DCM (10 mL) and the solution was cooled to 0° C. on an ice bath. MCPBA (0.104 g, 0.6 mmol) was added and the solution was stirred at 0° C. for 1 hour. The reaction was allowed to warm to room temperature and stirring was continued for a further 6 hours. The solution was diluted with DCM (30 mL) and washed with saturated NaHCO$_3$ (3×30 mL), 10% Na$_2$SO$_5$ (3×30 mL), and water (2×30 mL). The organic was dried over MgSO$_4$, filtered, and the solvent was concentrated in vacuo. The residue was purified by column chromatography 50% to 80% EtOAc in hexane to give a white solid 0.084 g, 68%, mp 51°–56° C.

[α]$_D^{21}$+13 (C=0.8 in CH$_3$OH) IR (film): 3350, 2931, 2857, 1690, 1655, and 1520 cm$^{-1}$. NMR (CDCl$_3$): 1.21–1.46 (22H, m, BocCH$_3$×3, αCH$_3$, CH$_2$×5), 1.84 (2H, m, C<u>H</u>$_2$CH$_2$SO$_2$CH$_3$), 2.77–3.45 (8H, m, βCH$_2$×2, CONH C<u>H</u>$_2$, C<u>H</u>$_2$SO$_2$CH$_3$), 2.89 (3H, s, SO$_2$C<u>H</u>$_3$), 4.00 (1H, m, αCH), 4.90 (1H, br, urethane NH), 5.85 (1H, br s, amide NH), 6.70 (1H, br, amide NH), 6.97 (2H, m, aromatics), 7.19–7.37 (8H, m, aromatics). MS (FAB, thioglycerol): 1232.2 (M$^{2+}$), 616.3 (MH$^+$), 516.2, 369, 325, 281. Analysis calculated for C$_{33}$H$_{49}$N$_3$O$_6$S·0.3 H$_2$O: C, 63.80; H, 8.05; N, 6.76. Found: C, 63.75; H, 7.96; N, 6.68.

EXAMPLE 25

(1-(1-[2-(4-Carbamoylmethoxy-phenyl)-ethylcarbamoyl]-1-methyl-2-phenyl-ethylcarbamoyl)-2-phenyl-ethyl)-carbamic acid tert-butyl ester

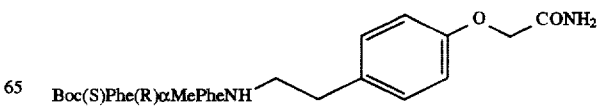

Step 1

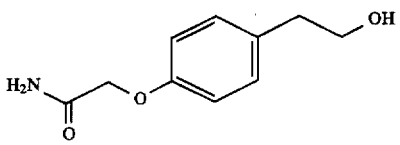

Potassium carbonate (1.20 g, 8.7 mmol) was added to a solution of 4-hydroxyphenethyl alcohol (1.32 g, 8.7 mmol) and 2-bromoacetamide (1.32 g, 8.7 mmol) in butan-2-one (25 mL). The suspension was heated at reflux for 4 hours and stirred at room temperature for 15 hours. The suspension was filtered and evaporated down to an off-white solid. Further purification by column chromatography using 5% MeOH/EtOAc gave a white solid (1.18 g, 92%).

NMR (DMSO-$d_6$): δ 2.60 (2H, t, —$CH_2$Ar), 3.49 (2H, m, —$CH_2$OH), 4.32 (2H, s, —$CH_2$—$CONH_2$), 4.54 (1H, bs, —OH), 6.79 (2H, d, Ar), 7.07 (2H, d, Ar), 7.31 (1H, bs), and 7.42 (1H, bs, —$CONH_2$). MS (CI): 178 (100%), 196 (M+1) IR (film): 3395, 3177, 2927, 1639 cm$^{-1}$.

Step 2

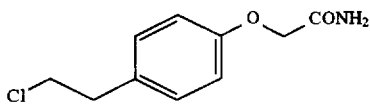

Tosyl chloride (1.29 g, 6.76 mmol) in DCM (25 mL) was added dropwise to a solution of the alcohol (1.10 g, 5.63 mmol) in pyridine. The suspension was stirred at room temperature for 16 hours. On removal of the solvents, the residue was taken up in DCM (100 mL) and extracted with 10% citric acid solution (3×100 mL) and water (2×80 mL). Drying ($MgSO_4$) and further purification by column chromatography using EtOAC:hexane (1:1) gave a white solid (400 mg, 33%).

NMR (DMSO-$d_6$): δ 2.91 (2H, t, J=6 Hz, —$CH_2$—), 3.75 (2H, t, J=6 Hz, —$CH_2$—), 4.34 (2H, s, —$CH_2$—), 6.83 (2H, d, Ar), 7.15 (2H, d, Ar), 7.32 (1H, bs), and 7.44 (1H, bs, —$CONH_2$). MS (CI): 231 (M+1→$NH_3$; 100%), 233 (M+3+$NH_2$), 214 (M+1), 216 (M+1+2).

Step 3

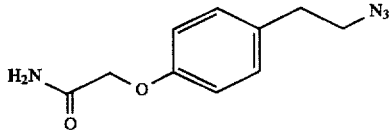

The chloro compound (0.380 g, 1.78 mmol) was dissolved in DMF (20 mL). Sodium azide (0.127 g, 1.96 mmol) and sodium iodide (0.267 g, 1.78 mmol) were added and the mixture was heated to 90° C. for 4 hours. On cooling, the mixture was poured onto 100 mL ice water and extracted with ether (3×100 mL). Drying and evaporation gave a white solid (0.35 g), 85% as the azide and 15% as chloro compound. Used crude in next step.

MS (CI): 164 (100%), 221 (M+1) IR (film):

Step 4

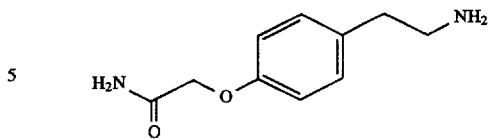

The crude azide (0.340 g, ~1.31 mmol) was dissolved in MeOH (30 mL) and Lindlar catalyst was added (0.170 g). This mixture underwent hydrogenation using the Parr apparatus at 43 psi and 25° C. for 6 hours. The catalyst was removed by filtration through celite. Evaporation gave an oil which was triturated with ethyl acetate to form a white solid (0.220 g, 86%).

NMR (DMSO-$d_6$): 2.50–2.74 (4H, m, —$CH_2$—$CH_2$—), 4.32 (2H, s, —$CH_2$—), 6.83 (2H, m, Ar), 7.05 (2H, m, Ar), 7.32 (1H, bs), and 7.43 (1H, bs, —$CONH_2$). MS (CI): 178 (100%), 195 (M+1).

Step 5

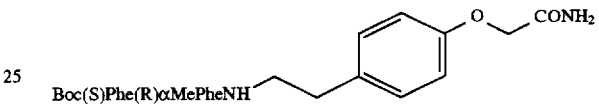

Dicyclohexylcarbodiimide (0.138 g, 0.67 mmol) in EtOAc (3 mL) was added dropwise to a solution of Boc(S) Phe(R)αMePhe-OH (0.285 g), and 1-hydroxybenzotriazole hydrate (0.090 g, 0.67 mmol) in ethyl acetate (20 mL). The resulting suspension was stirred for 1.5 hours and then cooled in the freezer. The mixture was filtered into a solution of the phenethylamine from Step 4 (0.130 g, 0.67 mmol) in DMF (5 mL) and ethyl acetate (5 mL) and allowed to stir at room temperature for 3 days. The solvents were removed under high vacuum and the residue was taken up in EtOAc (100 mL) and washed with 2M HCl (2×100 mL), 10% sodium carbonate solution (2×70 mL), and water (70 mL). Further purification by reverse phase column chromatography using 60% to 80% MeOH/$H_2O$ over 1 hour gave a white foam (0.165 g, 41%).

NMR (DMSO-$d_6$): δ 1.23 (3H, s, αCH$_3$), 1.26 (9H, s, Boc), 2.55–3.25 (8H, m, 2×$CH_2$-Ph, —$CH_2$—$CH_2$—), 4.13 (1H, m, αH), 4.31 (2H, s, —$OCH_2$—), 6.81–7.23 (15H, m, Ar, —OCONH—), 7.32 (1H, bs), and 7.42 (1H, bs, —$CONH_2$), 7.60 (1H, t, —CONH—), 7.76 (1H, s, —CONH—), mp 73°–81° C. MS: IR (film): 3321, 2932, 1694, 1669 cm$^{-1}$. [α]$_D^{23.3°}$ $^C$=+13.07 (c=1.025; MeOH) Analysis calculated for $C_{34}H_{42}N_4O_6$.0.35 $H_2O$ C, 67.05; H, 7.07; N, 9.20. Found: C, 67.08; H, 7.12; N, 8.91.

EXAMPLE 26

D-Phenylalaninamide, N-[(1,1-dimethylethoxy) carbonyl]-L-phenylalanyl-α-methyl-N-[9-(methylamino)-2-oxononyl]

Boc(S)Phe(R)αMePheNH($CH_2$)$_8$CONHMe

The acid [Boc(S)Phe(R)αMePhe] (0.200 g; 0.34 mmol), HBTU (0.130 g; 0.34 mmol) and DIPEA (0.165 mL; 0.68 mmol) in DMF (8 mL) were stirred at room temperature for 20 minutes DIPEA (0.124 mL; 0.51 mmol) and methylamine hydrochloride (0.023 g; 0.34 mmol) were added and the mixture was stirred for 16 hours.

On removal of DMF, the residue was taken up in EtoAc (60 mL) and washed with 2M HCl (2×50 mL), 10% $Na_2CO_3$ (2×50 mL) and brine (50 mL). Drying (MgSO$_4$) and further purification by column chromatography using 5% MeOH/DCM gave a white solid (0.204 g; 99%). mp 50°–58° C.;

NMR (CDCl$_3$): δ 1.22–1.64 (24H, m, Boc, αCH$_3$—(CH$_2$)$_6$—), 2.16 (2H, t,

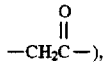
—CH$_2$C—), 2.78–2.90 (5H, m, N—Me, PhCH<u>H</u>—, PhCH<u>H</u>—), 3.05–3.25 (3H, m, —CONHC<u>H</u>$_2$—, PhC<u>H</u>H—), 3.41 (1H, d, PhC<u>H</u>H—), 3.98–4.05 (1H, m, αH), 4.93 (1H, d, —OCON<u>H</u>—), 5.62 (1H, bs, —CON<u>H</u>CH$_3$), 5.90 (1H, s, —CON<u>H</u>—), 6.70 (1H, bs, —CON<u>H</u>—), 6.96–7.00 (2H, m, Ar), 7.18–7.40 (8H, m, Ar). MS 495 (100%, m+1) IR (film): 3316, 2931, 1710, 1688, 1646 cm$^{-1}$ [α]$_D^{21.9°}$ C.=+10.14° C. (C=1.035; MeOH); Analysis calculated for C$_{34}$H$_{50}$N$_4$O$_5$·0.3H$_2$O: C, 68.04; H, 7.50; N, 9.33. Found: C, 67.93; H, 7.47; N, 9.22.

We claim:

1. A compound of the formula

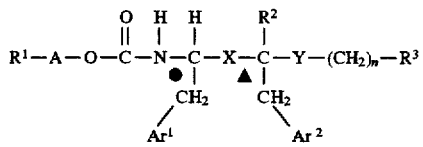

or a pharmaceutically acceptable salt thereof wherein:

R' is hydrogen,
OR$^4$,
CO$_2$R$^4$, wherein R$^4$ is hydrogen or alkyl, or phenyl unsubstituted or substituted by from 1 to 3 groups selected from:
  alkyl,
  halogen,
  nitro,
  CF$_3$,
  (CH$_2$)$_p$OR$^6$
  (CH$_2$)$_p$CO$_2$R$^6$,
  (CH$_2$)$_p$NR$^6$R$^7$ wherein p is an integer of from 0 to 6 and R$^6$ and R$^7$ are each independently hydrogen or alkyl;

A is —(CH$_2$)$_q$(C(CH$_3$)$_2$)$_r$(CH$_2$)$_s$— wherein q, r, and s are integers of from 0 to 6, 0 to 1, and 0 to 6, respectively;

Ar$^1$ and Ar$^2$ are each independently phenyl unsubstituted or substituted with from 1 to 3 substituents selected from:
  alkyl,
  halogen,
  nitro,
  CF$_3$,
  (CH$_2$)$_{1-6}$OR$^6$,
  (CH$_2$)$_t$CO$_2$R$^6$, or
  (CH$_2$)$_t$NR$^6$R$^7$ wherein t is an integer of from 0 to 6 and R$^6$ and R$^7$ are each independently hydrogen or alkyl;

X and Y are each independently
  —CONH—,
  —CONCH$_3$—,
  —COO—,
  —CH$_2$NH—,
  —NHCO—,
  —CH$_2$O—,
  —COCH$_2$—, or
  —CH$_2$CH—;

n is an integer of from 2 to 10;

R$^2$ is methyl; and
R$^3$ is hydrogen,
straight or branched alkyl of from 3 to 10 carbons with from 0 to 3 substituents selected from:
  (CH$_2$)$_n$OR$^8$,
  CO$_2$R$^8$,
  —NHCOCH$_3$,
  —NR$^8$R$^9$,
  —SO$_2$Me,
  —SOMe,
  —SO$_2$NH$_2$,
  —CONR$^8$R$^9$,
  —NHCONR$^8$R$^9$,
  —COR$^4$ wherein n is an integer of from 0 to 6, R$^4$ is as above, R$^8$ and R$^9$ are each independently hydrogen or alkyl,
  -guanidine,
  -amidine, R$^3$ is also

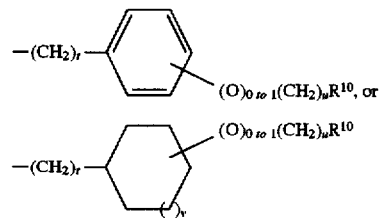

wherein t is an integer of from 0 to 5, v is an integer of from 0 to 2, u is an integer of from 0 to 4, and R$^{10}$ is hydrogen, hydroxy, alkoxy, COOH, CO$_2$alkyl, CONR$^8$R$^9$, NMCONR$^8$R$^9$ guanidine or amidine; and ● and ▲ indicate all stereoisomers.

2. A compound according to claim 1 wherein:
R$^1$ is hydrogen,
OR$^4$,
CO$_2$R$^4$ wherein R$^4$ is hydrogen, methyl, or ethyl,
cycloalkyl of from 4 to 8 carbons,
bicycloalkyl of 10 carbons,
tricycloalkyl of 10 carbons, or
phenyl;

A is —(CH$_2$)$_q$(C(CH$_3$)$_2$)$_r$(CH$_2$)$_s$— wherein q, r, and s are integers of from 0 to 2, 0 to 1, and 0 to 4, respectively;

Ar$^1$ and Ar$^2$ are each independently phenyl unsubstituted or mono- or disubstituted by:
  alkyl,
  halogen,
  CF$_3$,
  NO$_2$, or
  NH$_2$;

X and Y are each independently
  —CONH—,
  —CONCH$_3$—,
  —CO$_2$—, or
  —CH$_2$NH—;

n is an integer of from 2 to 9; and
R$^3$ is hydrogen,
straight, branched, or cyclic alkyl of from 3 to 10 carbons with from 0 to 3 substituents selected from:
  OH,
  OCH$_3$,
  CO$_2$R$^8$,
  NHCOCH$_3$,
  NR$^8$R$^9$, CONR⁸R⁹,
NHCONR⁸R⁹ wherein R⁸ and R⁹ are each independently selected from hydrogen and methyl, or COCH₃,

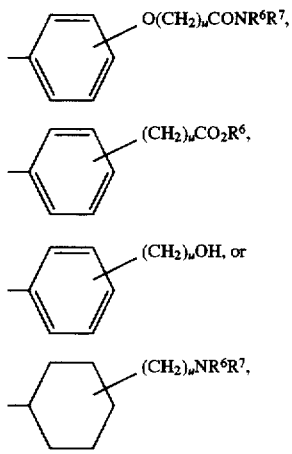

wherein u is an integer of from 0 to 4 and R⁶ and R⁷ are each independently selected from hydrogen and methyl.

3. A compound according to claim 1 wherein:

R¹ is hydrogen,
  OR⁴,
  CO₂R⁴ wherein R⁴ is hydrogen or methyl,
  cycloalkyl of from 5 to 7 carbons;
A is —(CH₂)$_q$(C(CH₃)₂)$_r$(CH₂)$_s$— wherein q, r, and s are integers of from 0 to 3, 0 to 1, and zero, respectively;
Ar¹ and Ar² are each independently phenyl unsubstituted or mono- or disubstituted by:
  alkyl,
  chloro, or
  CF₃;
X and Y are each independently
  —CONH—,
  —CONCH₃—,
  —CO₂—, or
  —CH₂NH—;
n is an integer of from 2 to 9; and
R³ is hydrogen,
  straight, branched, or cycloalkyl of from 3 to 10 carbons with from 0 to 3 substituents selected from:
  OH,
  OCH₃,
  CO₂R⁸,
  CONR⁸R⁹, or
  NHCONR⁸R⁹,

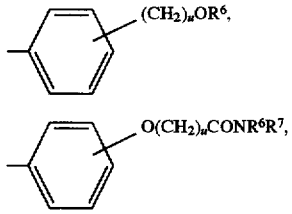

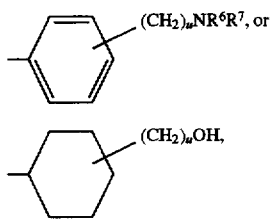

wherein u is an integer of from 0 to 3, R⁶ and R⁷ are each independently hydrogen and methyl, R⁸ and R⁹ are each independently hydrogen and methyl.

4. A compound according to claim 1 wherein:

R¹ is cyclohexane,
  cyclopentane,
  methylcyclohexane,
  methylcyclopentane,
  phenylethyl,
  t-butyl,
  2,2-dimethylpropane, or
  2,2-dimethylpentane;
A when q, r and s are 0;
Ar¹ and Ar² are each phenyl;
X and Y are each independently selected from —CONH— and —CH₂NH—;
n is an integer of from 3 to 8;
R³ is straight, branched, or cycloalkyl of from 3 to 9 carbons with 1 substituent selected from:
  OH,
  —OCH₃,
  —CONR⁸R⁹,
  —NHCONR⁸R⁹,

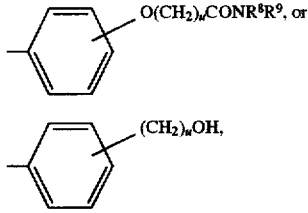

wherein u is an integer of from 0 to 3 and R⁸ and R⁹ are each independently selected from hydrogen and methyl.

5. A method for treating pain in a mammal comprising administering an effective amount of a compound according to claim 1 to said mammal.

6. A method for treating inflammation disorders in a mammal comprising administering an effective amount of a compound according to claim 1 to said mammal.

7. A method for inducing vasodilation in a mammal comprising administering an effective amount of a compound according to claim 1 to said mammal.

8. A method for inhibiting smooth muscle contraction in a mammal comprising administering an effective amount of a compound of claim 1 to said mammal.

* * * * *